US010683319B2

(12) United States Patent
de la Rosa et al.

(10) Patent No.: US 10,683,319 B2
(45) Date of Patent: Jun. 16, 2020

(54) PHOSPHORAMIDATES FOR THE TREATMENT OF HEPATITIS B VIRUS

(71) Applicant: Emory University, Atlanta, GA (US)

(72) Inventors: Abel de la Rosa, Alpharetta, GA (US); Gregory R. Bluemling, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/536,237

(22) PCT Filed: Dec. 7, 2015

(86) PCT No.: PCT/US2015/064338
§ 371 (c)(1),
(2) Date: Jun. 15, 2017

(87) PCT Pub. No.: WO2016/099982
PCT Pub. Date: Jun. 23, 2016

(65) Prior Publication Data
US 2019/0062364 A1    Feb. 28, 2019

Related U.S. Application Data

(60) Provisional application No. 62/091,686, filed on Dec. 15, 2014, provisional application No. 62/094,117, filed on Dec. 19, 2014, provisional application No. 62/201,974, filed on Aug. 6, 2015.

(51) Int. Cl.
| | | |
|---|---|---|
| C07H 19/10 | (2006.01) | |
| A61K 45/06 | (2006.01) | |
| A61K 31/7072 | (2006.01) | |
| A61K 9/127 | (2006.01) | |
| C07B 59/00 | (2006.01) | |
| C07H 19/09 | (2006.01) | |
| A61P 31/20 | (2006.01) | |
| C07D 405/04 | (2006.01) | |

(52) U.S. Cl.
CPC ............ C07H 19/10 (2013.01); A61K 9/127 (2013.01); A61K 31/7072 (2013.01); A61K 45/06 (2013.01); A61P 31/20 (2018.01); C07B 59/005 (2013.01); C07D 405/04 (2013.01); C07H 19/09 (2013.01)

(58) Field of Classification Search
CPC ...................................................... C07H 19/10
See application file for complete search history.

(56) References Cited

U.S. PATENT DOCUMENTS

| 3,687,931 A | 8/1972 | Verheyden et al. |
| 5,587,362 A | 12/1996 | Chu et al. |
| 7,888,330 B2 | 2/2011 | Shields et al. |
| 2003/0109697 A1 | 6/2003 | Shepard et al. |
| 2004/0229839 A1 | 11/2004 | Babu et al. |
| 2012/0071434 A1 | 3/2012 | Smith et al. |
| 2014/0271547 A1 | 9/2014 | Kukhan et al. |

FOREIGN PATENT DOCUMENTS

| WO | 1995020595 | 8/1995 |
| WO | 2005012327 | 2/2005 |
| WO | 2006063149 | 6/2006 |
| WO | 2006133092 A1 | 12/2006 |
| WO | 2007056596 | 5/2007 |
| WO | 2009132123 | 10/2009 |
| WO | 2014169280 | 10/2014 |

OTHER PUBLICATIONS

Meneghesso et al., Antiviral Research (2012), 94(1), pp. 35-43.*
International Preliminary Report on Patentability issued in Application No. PCT/US2015/064338 dated Jun. 29, 2017.
International Search Report and Written Opinion issued in Application No. PCT/US2015/064338 dated Jun. 27, 2016.
Office Action issued in Eurasian Patent Application No. 201791356/28 dated Feb. 15, 2018.
Germon S. A. et al., Inhibitory Effect of 2'-Fluoro-5-Methyl-b-LArabinofuranosyl-Uracil on Duck Hepatitis B Virus Replication. Antimicrob. Agents Chemother., Feb. 28, 1998, vol. 42, No. 2, pp. 369-376.
Office Action issued in Eurasian Patent Application No. 201791356/28, dated Aug. 23, 2018.
Search Report issued in Singaporean Application No. 11201704785R, dated Jul. 5, 2018.
Written Opinion issued in Singaporean Application No. 11201704785R, dated Jul. 5, 2018.
Ashoke et al., Clevudone (L-FMAU): a unique antiviral agent for the treatment of chronic hepatitis B virus infection, Collection Symposium Series, 2008 pp. 239-243.
Pradere et al., Synthesis of Nucleoside Phosphate and Phosphonate Prodrugs, Chemical Reviews, vol. 114, pp. 9154-9218. 2014.
Gudmundsson et al., Phosphoramidate Protides of Carbocyclic 2',3'-Dideoxy-2',3'-Didehydro-7-Deazaadenosine with Potent Activity Against HIV and HBV, Nucleosides, Nucleotides and Nucleic Acids, vol. 23, No. 12, pp. 1929-1938, 2004.
Gudmundsson et al., Phosphoramidate Protides of 2',3'-Dideoxy-3'-fluoroadenosine and Related Nucleosides with Potent Activity Against HIV and HBV, Nucleosides, Nucleotides and Nucleic Acids, vol. 22, No. 10, pp. 1953-1961, 2003.
Partial Supplementary European Search Report issued for European Application No. 15870694.5, dated Oct. 15, 2018.
English Translation of the Office Action issued for Eurasian Application No. 201791356/28, dated Jan. 30, 2019.
McGuigan C., et al., "Synthesis and Evaluation of Some Masked Phosphate Esters of the Anti-Herpesvirus Drug 882C (Netivudine) as Potential Antiviral Agents. Antiviral Chemistry and Chemotherapy," Jun. 1, 1998, vol. 9, No. 3, pp. 233-243.
Written Opinion issue by the Intellectual Property Office of Singapore dated Aug. 8, 2019 for Patent Application No. 11201704785R.

(Continued)

*Primary Examiner* — Brian J Davis
(74) *Attorney, Agent, or Firm* — Meunier Carlin & Curfman LLC

(57) ABSTRACT

Disclosed are compounds to the treatment of infectious diseases and methods of treating such diseases. The compounds are derivatives of clevudine.

8 Claims, 2 Drawing Sheets

Specification includes a Sequence Listing.

(56) References Cited

OTHER PUBLICATIONS

Sharon, Ashoke, "Clevudine (L-FMAU): A unique antiviral agent for the treatment of chronic hepatitis B virus infection," Collection Symposium Series, 2008, vol. 10, pp. 239-243.
Pradere, U., et. al., "Synthesis of nucleoside phosphate and phosphonate prodrug," Chemical Reviews, 2014, vol. 114, No. 18, pp. 9154-9218.
Gudmundsson, K. et. al., "Phosphoramidate protides of carboxylic 2',3'-dideoxy-2',3'-didehydro-7-deazaadenosine with potent activity against HIV and HBV," Nucleosides, Nucleotides & Nucleic Acids, 2004, vol. 23, No. 12, pp. 1929-1937.
Gudmundsson, K. et. al., "Phosphoramidate protides of 2',3'-dideoxy-3'-fluroadenosine and related nucleosides with potent activity against HIV and HBV," Nucleosides, Nucleotides & Nucleic Acids, 2003, vol. 22, No. 10, pp. 1953-1961.
Office Action issued in Japanese Application No. 2017-532167, dated Nov. 5, 2019 and English Language Translation.
English Summary of Office Action issued in Israeli Application No. 252842, dated Dec. 3, 2019.
First Examination Report for Australian Application No. 2015363042 dated Mar. 25, 2020.
Extended European Search Report for European Application No. 17816278.0 dated Feb. 21, 2020.
Search Report and Written Opinion for Singaporean Application No. 11201811316Y dated Mar. 6, 2020.
English translation of Office Action for Eurasian Application No. 201990059/28 dated Mar. 27, 2020.
English translation of Notice of Reasons for Rejection for Japanese Application No. 2017-532167 dated Feb. 4, 2020.

* cited by examiner

```
                        SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: synthetic construct

<400> SEQUENCE: 1
ccgtctgtgc cttctcatct g                                        21

<210> SEQ ID NO 2
<211> LENGTH: 29
<212> TYPE: DNA
<213> ORGANISM: Artificial Sequence
<220> FEATURE:
<223> OTHER INFORMATION: synthetic construct

<400> SEQUENCE: 2
agtccaagag tyctcttatr yaagacctt                                29

<210> SEQ ID NO 3
<211> LENGTH: 17
<212> TYPE: DNA
<213> ORGANISM: Artificial Sequence
<220> FEATURE:
<223> OTHER INFORMATION: synthetic construct

<400> SEQUENCE: 3
cttcgcttca cctctgc                                             17
```

PHOSPHORAMIDATES FOR THE TREATMENT OF HEPATITIS B VIRUS

BACKGROUND

Hepatitis B virus (HBV) is an infectious disease that targets the liver resulting in either an acute infection, with symptoms arising in 45 to 160 days, or a chronic infection, which 350 million people worldwide are affected by. Estimates indicate that 600,000 deaths occur each year as a result of consequences related to HBV infection. HBV possesses a 3.2-kb relaxed circular DNA (rcDNA) genome that is used to form covalently closed circular DNA (cccDNA) in a host cell. The cccDNA is then transcribed by RNA polymerase II, a host DNA-dependent RNA polymerase, to produce pregenomic RNA (pgRNA). The pgRNA is then used by the virally encoded reverse transcriptase to form rcDNA. The goals of current treatments for chronic HBV infections are to reduce HBV replication and reduce liver damage.

Current treatments for chronic HBV infections include pegylated alpha interferon and nucleoside/nucleotide reverse transcriptase inhibitors (NRTIs). NRTIs are converted to their corresponding 5'-triphosphate, or diphosphate in the case of phosphonate containing NRTIs, and reduce viral replication by inhibiting the HBV encoded polymerase. Clevudine is an NRTI that is no longer being developed for the treatment of chronic HBV because of drug-related skeletal myopathy that was a result of mitochondrial dysfunction in patients. Interestingly, clevudine triphosphate has been shown to be a competitive non-substrate inhibitor of the HBV encoded polymerase, and due to its long intracellular half-life, is able to suppress HBV replication for an extended period of time after drug withdrawal.

What are thus needed are new compounds for the treatment of HBV. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to derivatives of clevudine and methods of making and using such derivatives. Also disclosed are methods of treating HBV infections with the disclosed compounds. Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
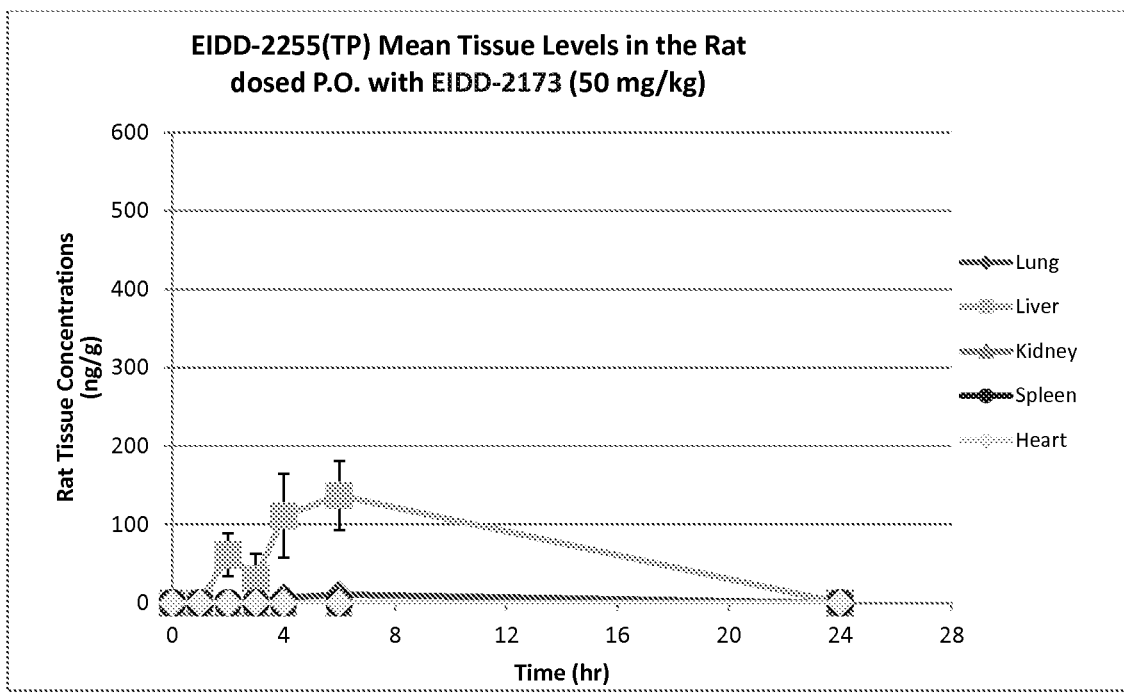
FIG. 1 is a graph showing clevudine 5'-triphosphate mean tissue levels from rats dosed P.O. with EIDD-2173.
Figure 2:
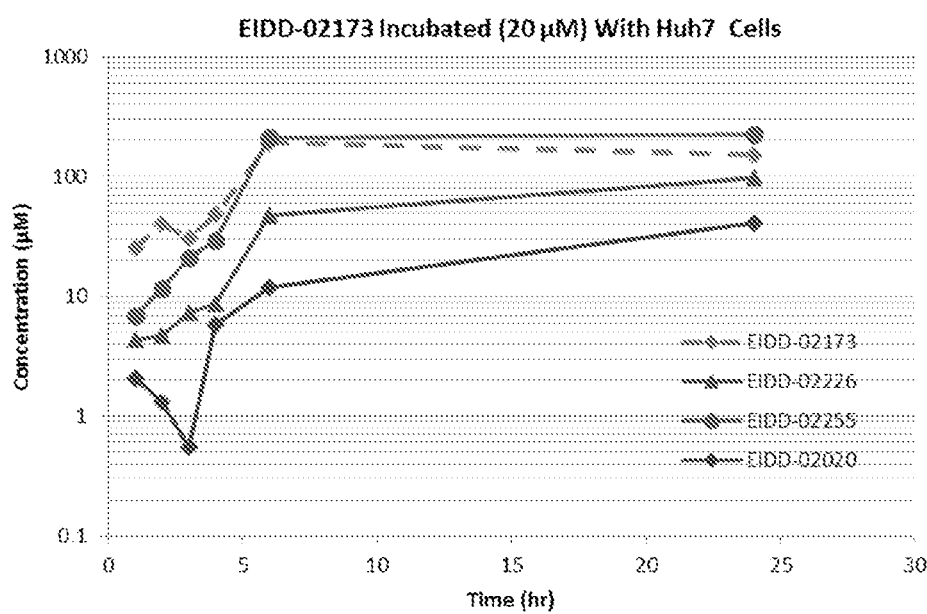
FIG. 2 is a graph showing Huh-7 Cell Uptake and Metabolism of EIDD-02173 (20 μM).
Figure 3:
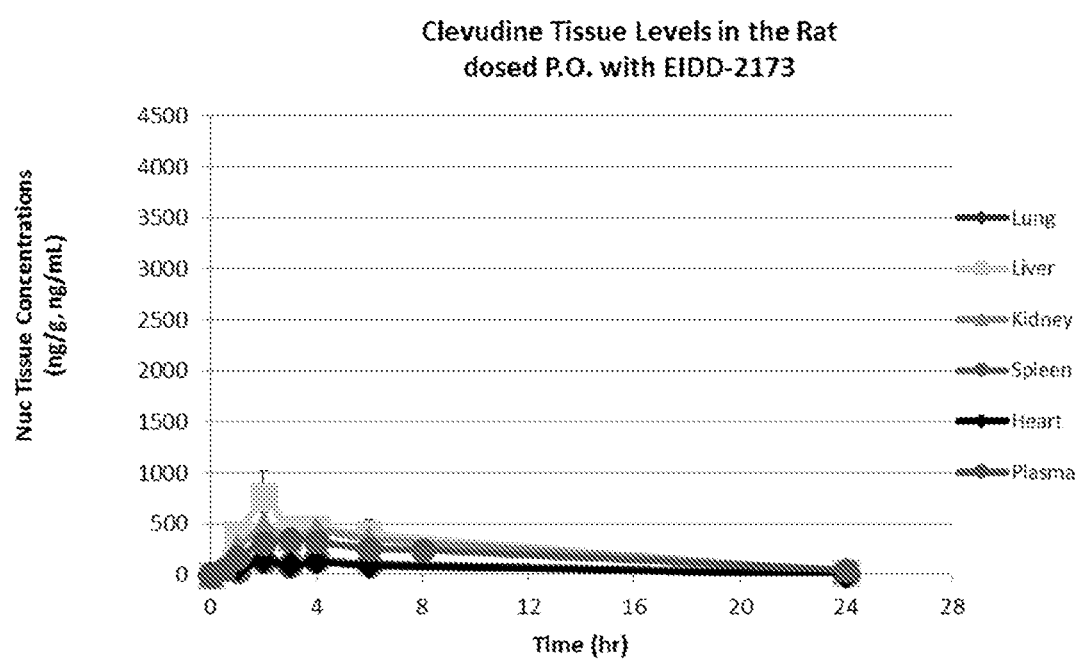
FIG. 3 is a graph showing clevudine nucleoside tissue levels from rats dosed P.O. with EIDD-2173 (5'-Phosphoramidate).

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an antibiotic" includes mixtures of two or more such antibiotics, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., viral infection). It is understood that this is typically in relation to some standard or expected value, in other words it is relative, but that it is not always necessary for the standard or relative value to be referred to. For example, "reduces viral infection" means decreasing the amount of bacteria relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as infection), diminishment of extent of infection, stabilized (i.e., not worsening) state of infection, preventing or delaying spread of the infection, preventing or delaying occurrence or recurrence of infection, and delay or slowing of infection progression.

The term "patient" preferably refers to a human in need of treatment with an antibiotic or treatment for any purpose, and more preferably a human in need of such a treatment to treat viral infection. However, the term "patient" can also refer to non-human animals, preferably mammals such as dogs, cats, horses, cows, pigs, sheep and non-human primates, among others, that are in need of treatment with an antibiotics.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A^n$ is used herein as merely a generic substituent in the definitions below.

The term "alkoxy" as used herein is an alkyl group bound through a single, terminal ether linkage; that is, an "alkoxy" group can be defined as —$OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O$^-$.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —NO$_2$.

The term "cyano" as used herein is represented by the formula —CN

The term "azido" as used herein is represented by the formula —N$_3$.

The term "sulfonyl" is used herein to refer to the sulfo-oxo group represented by the formula —S(O)$_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH$_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples and Figures.

Compositions

To address the myopathy concerns associated with clevudine, the synthesis of the (S,S) and (S,R) diastereomers of clevudine phosphoramidate was performed. The phosphoramidate moiety was utilized to deliver clevudine, as its 5'-monophosphate, to the liver reducing 1) systemic exposure to clevudine and 2) the possibility of skeletal myopathy. Both phosphoramidates showed anti-HBV activity similar to clevudine with the (S,S) diastereomer being slightly more potent.

In a specific example, disclosed is a compound having the formula:

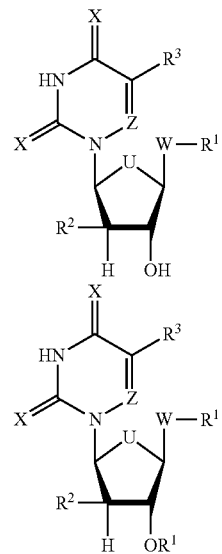

or a pharmaceutically acceptable salt thereof, wherein each $R^1$ is, independently, hydrogen or selected from one of the formula:

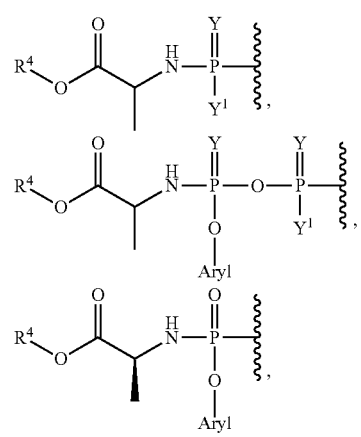

-continued

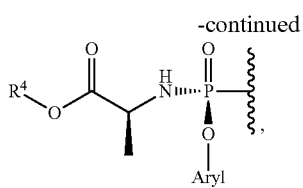

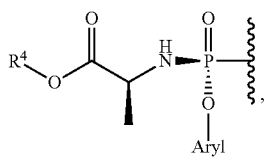

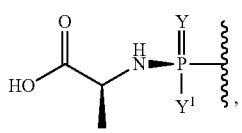

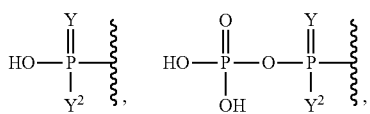

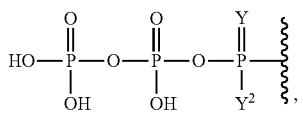

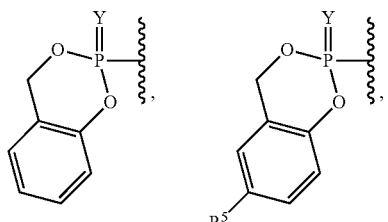

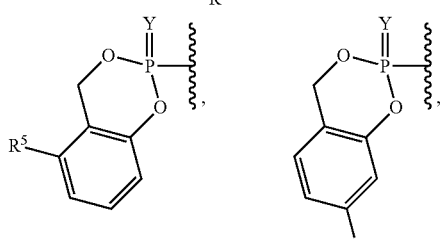

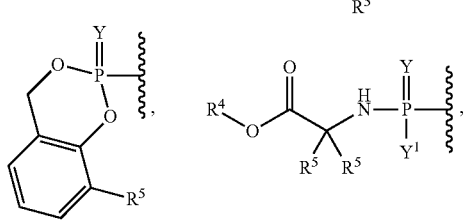

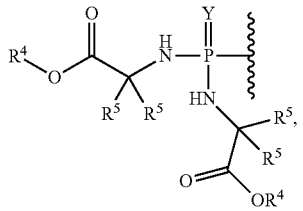

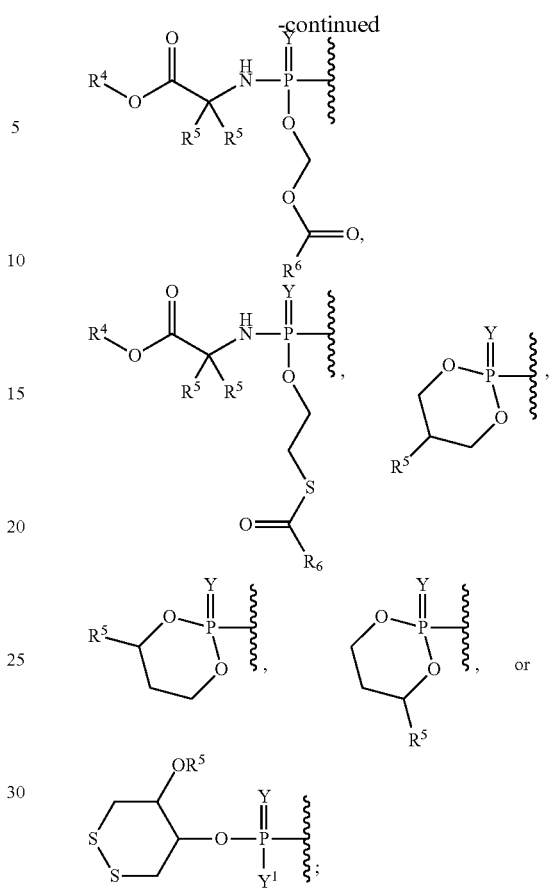

each X is, independently, O or S;
Z is N or $CR^7$;
U is O or S;
W is $CH_2O$, $CD_2O$, $CF_2O$, $CH_2CH_2$;
Y is O or S;
$Y^1$ is OH, OAryl, OAlkyl, or $BH_3^-M^+$;
$Y^2$ is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^2$ is Cl, Br, I, methyl, triflouromethyl, cyano, alkyl, alkenyl, propargyl, substituted alkyl, substituted alkenyl, substituted alkynyl, alkoxy, substituted ethnyl, hydroxymethyl, fluoromethyl, difluoromethyl, formyl, acyl, amino, substituted amino, azido, thiol, hydroxyamino, or substituted thio; and
$R^3$ is hydrogen, deuterium, methyl, fluoromethyl, difluoromethyl, trifluoromethyl, alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy; and R[7] is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In a specific example, disclosed is a compound having the formula:

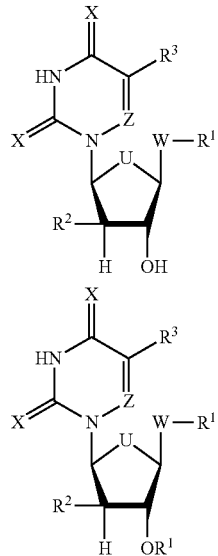

or a pharmaceutically acceptable salt thereof, wherein each R[1] is, independently, hydrogen or selected from one of the formula:

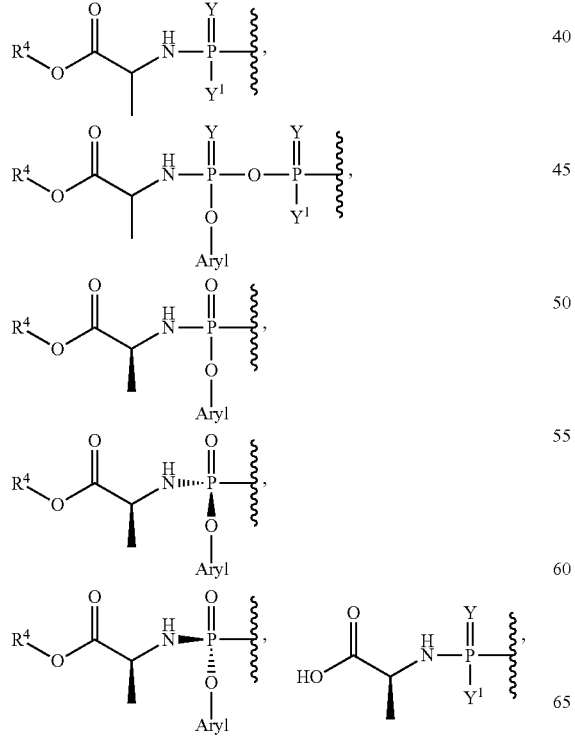

-continued

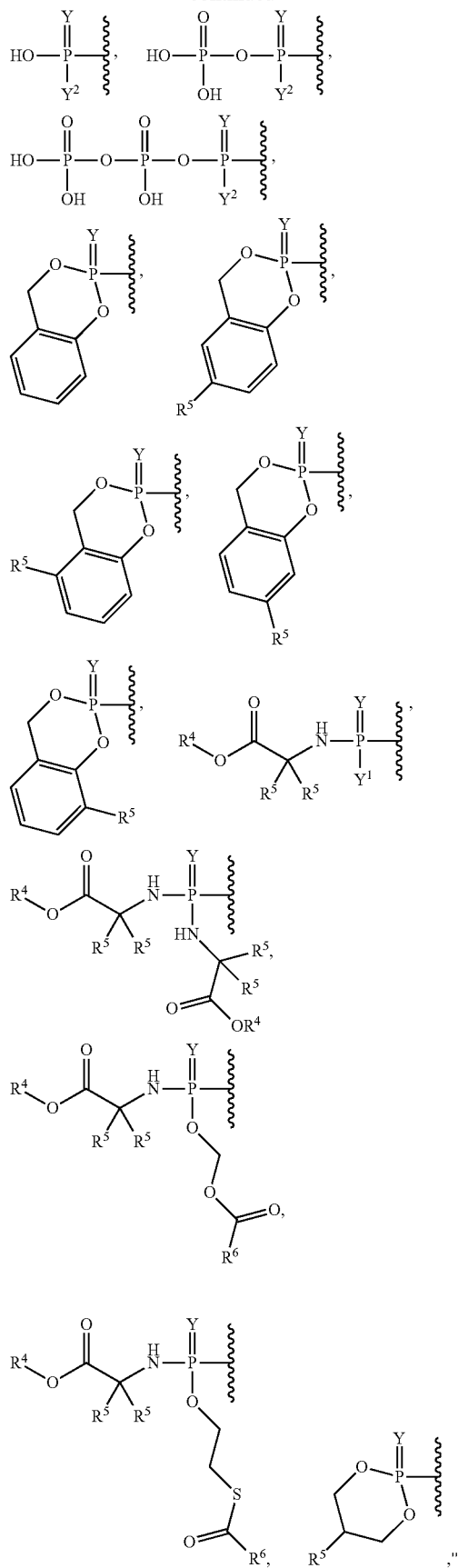

-continued

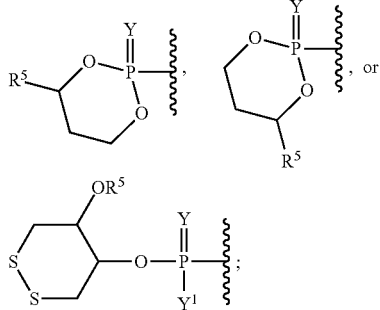

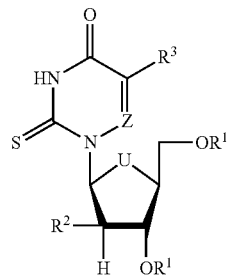

each X is, independently, O or S;
Z is N or CR$^7$;
U is O or S;
W is CD$_2$O, CF$_2$O, CH$_2$CH$_2$;
Y is O or S;
Y$^1$ is OH, OAryl, OAlkyl, or BH$_3^-$M$^+$;
Y$^2$ is OH or BH$_3^-$M$^+$;
Aryl is phenyl, 1-naphthyl, 2-naphthyl, aromatic, heteroaromatic, 4-substituted phenyl, 4-chlorophenyl, or 4-bromophenyl;
R$^2$ is F, OH, alkynyl, ethynyl;
R$^3$ is hydrogen, deuterium, methyl, fluoromethyl, difluoromethyl, trifluoromethyl, alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl;
R$^4$ is hydrogen, methyl, ethyl, isopropyl, cyclopentyl, cyclohexyl, neopentyl, benzyl, alkyl, branched alkyl, cycloalkyl, or lipid;
R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl;
R$^6$ is methyl, ethyl, tert-butyl, C$_{1-22}$ alkoxy, C$_{1-22}$ alkyl, branched alkyl, cycloalkyl, aryl, substituted aryl, or alkyoxy; and
R$^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In a specific example, disclosed is a compound having the formula:

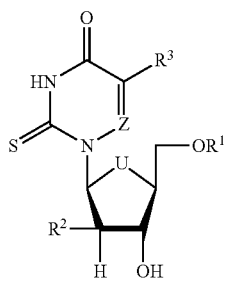

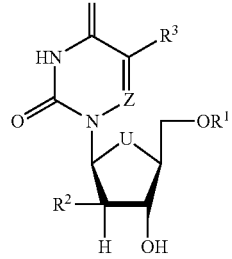

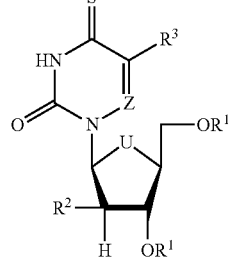

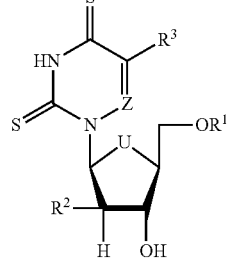

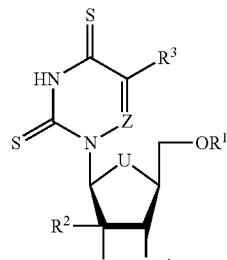

or a pharmaceutically acceptable salt thereof, wherein
each R$^1$ is, independently, hydrogen or selected from one of the formula:

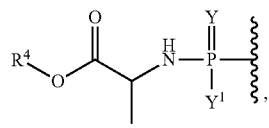

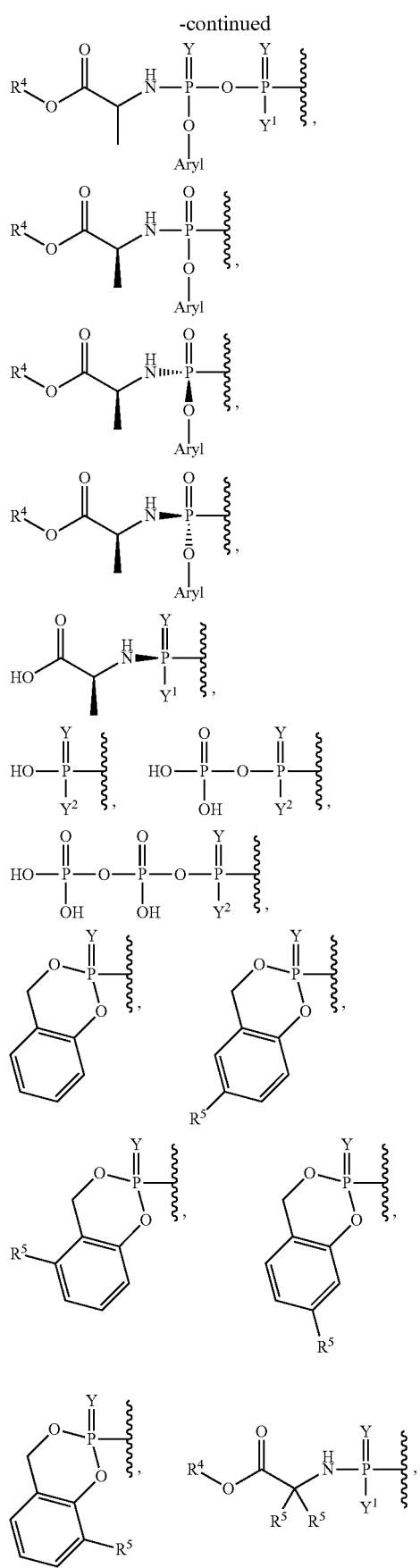
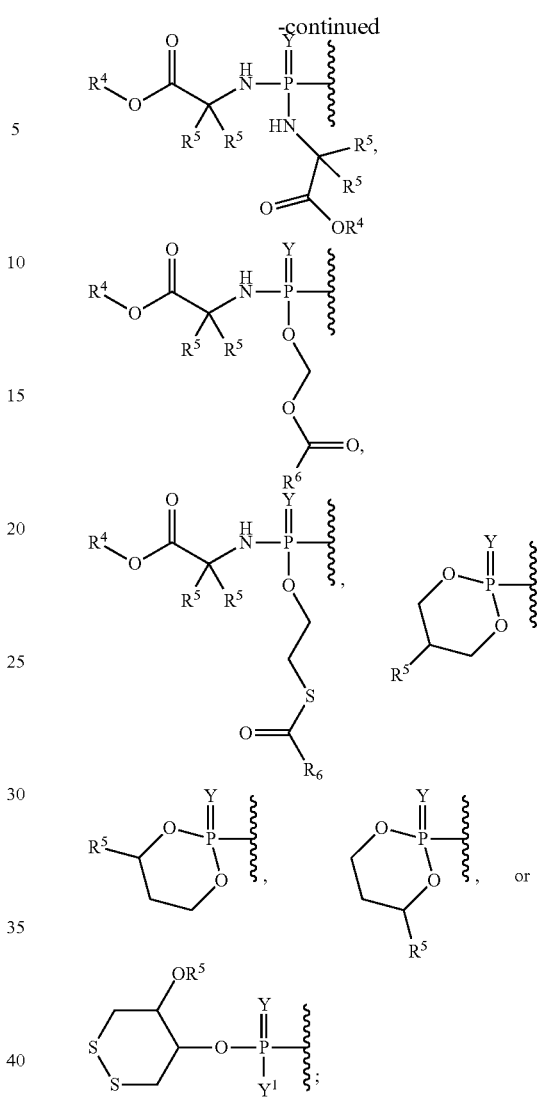

Z is N or CR⁷;
U is O or S;
Y is O or S;
Y¹ is OH, OAryl, OAlkyl, or $BH_3^-M^+$;
Y² is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
R² is F, OH, alkynyl, ethynyl;
R³ is hydrogen, deuterium, methyl, fluoromethyl, difluoromethyl, trifluoromethyl, alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl;
R⁴ is hydrogen, methyl, ethyl, isopropyl, cyclopentyl, cyclohexyl, neopentyl, benzyl, alkyl, branched alkyl, cycloalkyl, or lipid;
R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
R⁶ is methyl, ethyl, tert-butyl, $C_{1-22}$ alkoxy, $C_{1-22}$ alkyl, branched alkyl, cycloalkyl, aryl, substituted aryl, or alkyoxy; and $R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In a specific example, disclosed is a compound having the formula:

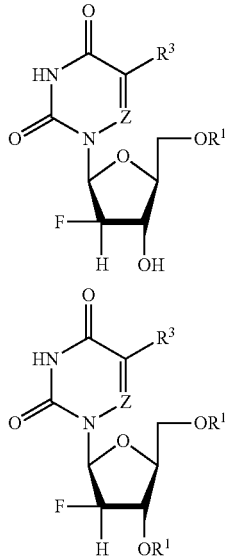

or a pharmaceutically acceptable salt thereof, wherein each $R^1$ is, independently, hydrogen or selected from one of the formula:

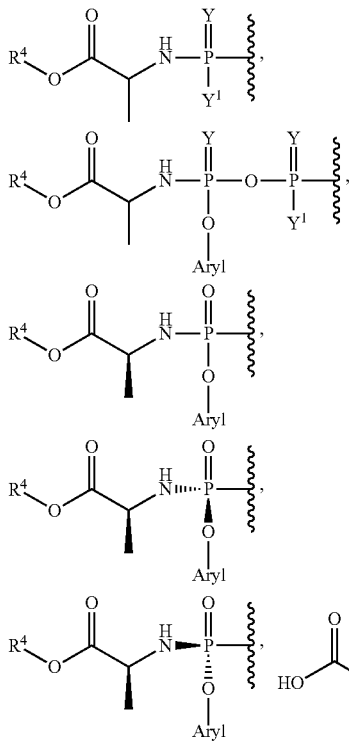

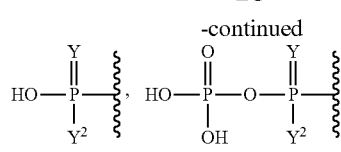

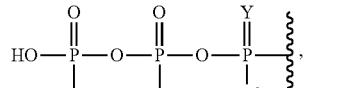

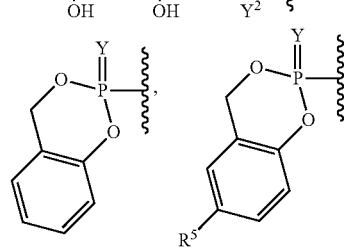

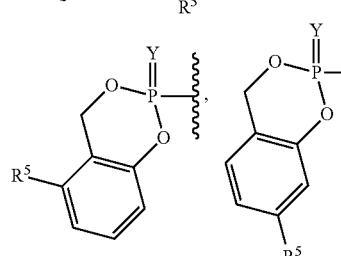

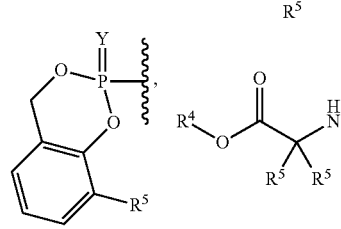

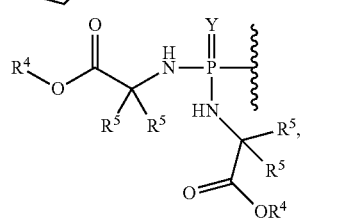

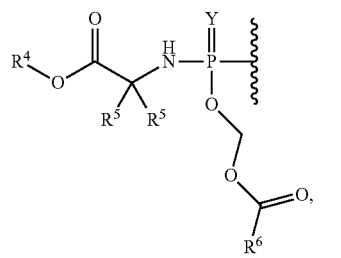

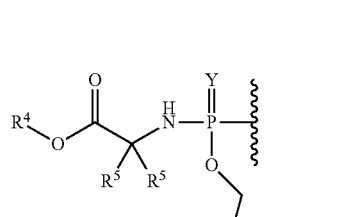

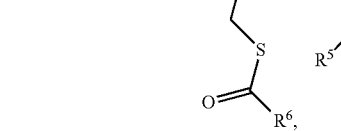

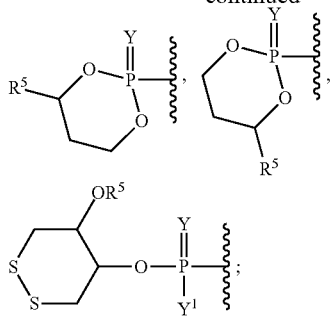

Z is N or CR⁷;
Y is O or S;
$Y^1$ is OH, OAryl, OAlkyl, or $BH_3^-M^+$;
$Y^2$ is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^3$ is hydrogen, deuterium, methyl, fluoromethyl, difluoromethyl, trifluoromethyl, alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy; and
$R^7$ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.
In a specific example, disclosed is a compound having the formula:

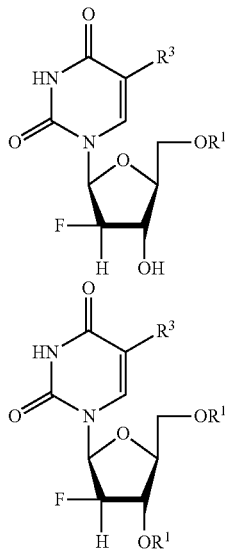

or a pharmaceutically acceptable salt thereof, wherein each $R^1$ is, independently, selected from one of the formula:

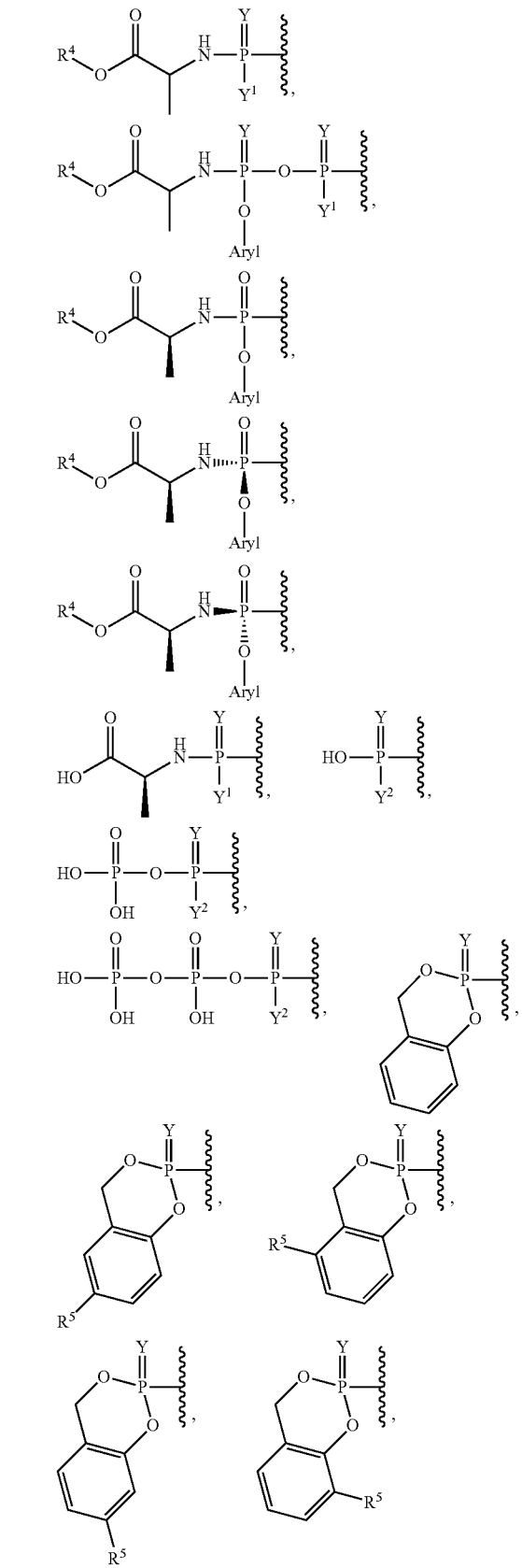

-continued

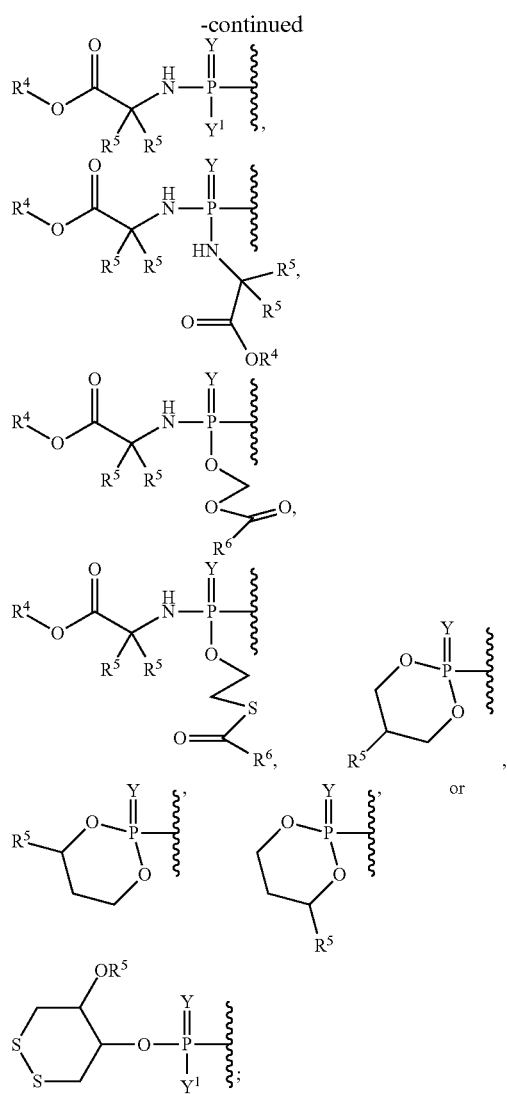

Y is O or S;

Y$^1$ is OH, OAryl, OAlkyl, or BH$_3^-$M$^+$;

Y$^2$ is OH or BH$_3^-$M$^+$;

Aryl is phenyl, 1-naphthyl, 2-naphthyl, aromatic, heteroaromatic, 4-substituted phenyl, 4-chlorophenyl, or 4-bromophenyl;

R$^3$ is hydrogen, deuterium, fluoromethyl, difluoromethyl, trifluoromethyl, alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl;

R$^4$ is hydrogen, methyl, ethyl, isopropyl, cyclopentyl, cyclohexyl, neopentyl, benzyl, alkyl, branched alkyl, cycloalkyl, or lipid;

R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl; and R$^6$ is methyl, ethyl, tert-butyl, C$_{1-22}$ alkoxy, C$_{1-22}$ alkyl, branched alkyl, cycloalkyl, aryl, substituted aryl, or alkyoxy.

In a specific example, disclosed is a compound having the formula:

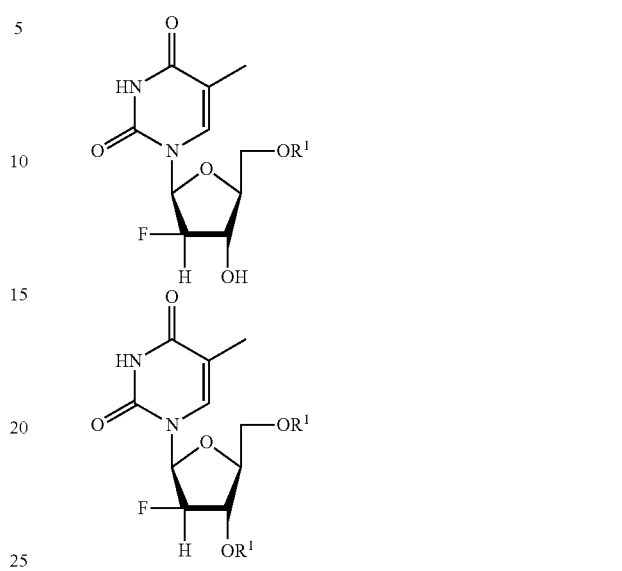

or a pharmaceutically acceptable salt thereof, wherein each R$^1$ is, independently, selected from one of the formula:

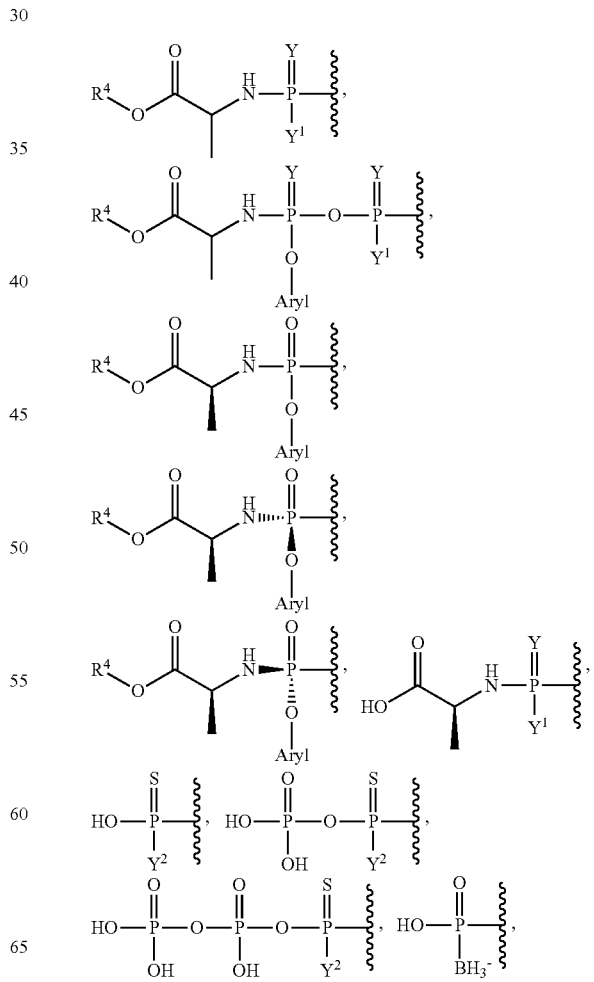

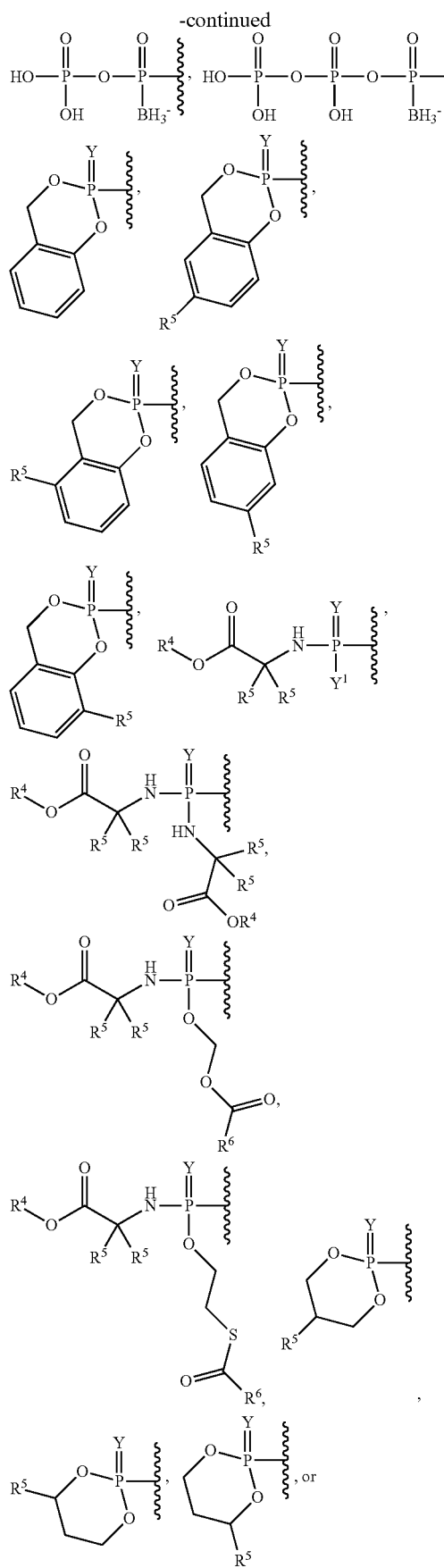

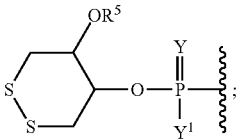

Y is O or S;

Y$^1$ is OH, OAryl, OAlkyl, or BH$_3^-$M$^+$;

Y$^2$ is OH or BH$_3^-$M$^+$;

Aryl is phenyl, 1-naphthyl, 2-naphthyl, aromatic, heteroaromatic, 4-substituted phenyl, 4-chlorophenyl, or 4-bromophenyl;

R$^4$ is hydrogen, methyl, ethyl, isopropyl, cyclopentyl, cyclohexyl, neopentyl, benzyl, alkyl, branched alkyl, cycloalkyl, or lipid;

R$^5$ is hydrogen, deuterium, hydroxyl, cyano, azido, amino, substituted amino, aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl; and R$^6$ is methyl, ethyl, tert-butyl, C$_{1-22}$ alkoxy, C$_{1-22}$ alkyl, branched alkyl, cycloalkyl, aryl, substituted aryl, or alkyoxy.

In a specific example, disclosed is a compound having the formula:

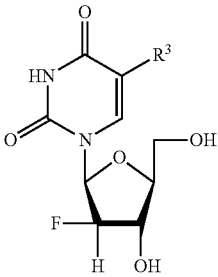

or a pharmaceutically acceptable salt thereof, wherein

R$^3$ is deuterium, fluoromethyl, difluoromethyl, C$_3$-C$_6$ alkyl, propargyl, amino, hydroxyl, cyano, formyl, acyl, substituted alkyl, substituted alkynyl, substituted amino, substituted ethynyl or hydroxymethyl;

In a specific example, disclosed is a compound having the formula:

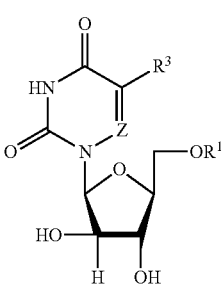

-continued
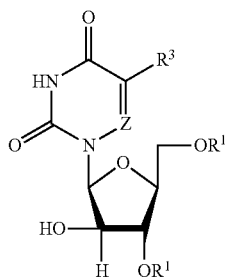
or a pharmaceutically acceptable salt thereof, wherein each $R^1$ is, independently, selected from one of the formula:
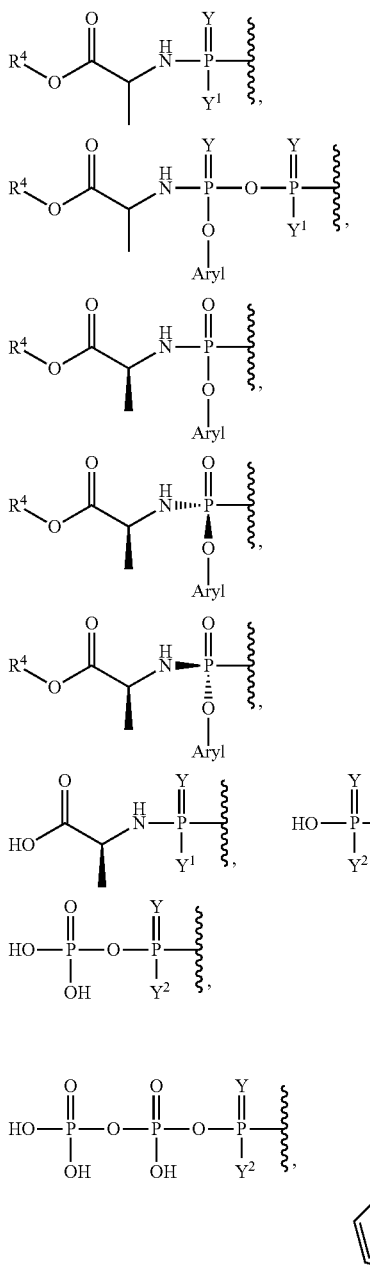
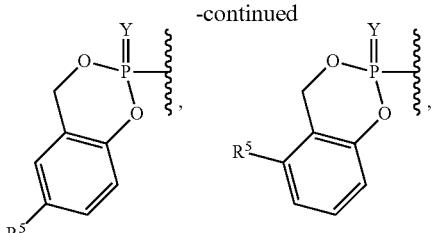
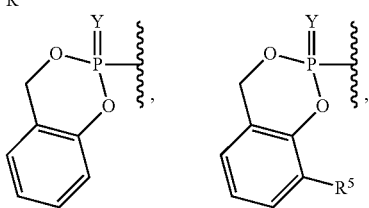
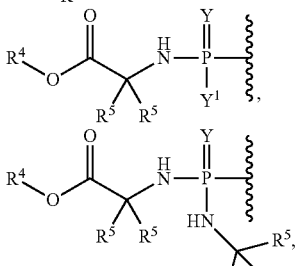
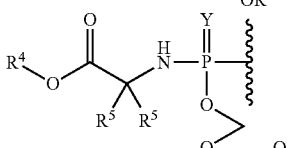
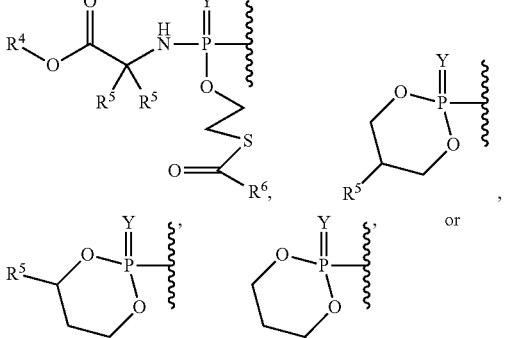
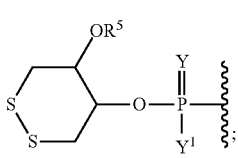
Z is N or $CR^2$;
Y is O or S;
$Y^1$ is OH, OAryl, OAlkyl, or $BH_3^-M^+$;
$Y^2$ is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;

R³ is hydrogen, deuterium, methyl, fluoromethyl, difluoromethyl, trifluoromethyl, substituted methyl, $C_2$-$C_6$ alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl;

R⁴ is hydrogen, methyl, ethyl, isopropyl, cyclopentyl, cyclohexyl, neopentyl, benzyl, alkyl, branched alkyl, cycloalkyl, or lipid;

R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R⁶ is methyl, ethyl, tert-butyl, $C_{1-22}$ alkoxy, $C_{1-22}$ alkyl, branched alkyl, cycloalkyl, aryl, substituted aryl, or alkyoxy;

R⁷ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In a specific example, disclosed is a compound having the formula:

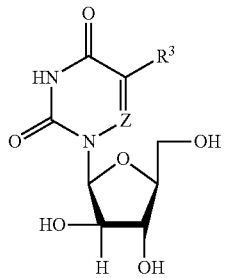

or a pharmaceutically acceptable salt thereof, wherein
Z is N or CR²;
R³ is hydrogen, deuterium, methyl, fluoromethyl, difluoromethyl, trifluoromethyl, substituted methyl, $C_2$-$C_6$ alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl; and R⁷ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;
wherein R³ is methyl R⁷ cannot be methyl; and
wherein R³ is H R⁷ cannot be methyl.

In a specific example, disclosed is a compound having the formula:

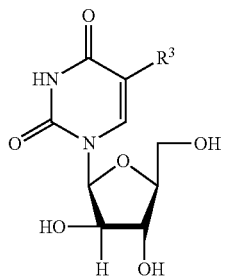

or a pharmaceutically acceptable salt thereof, wherein

R³ is deuterium, fluoromethyl, difluoromethyl, trifluoromethyl, substituted methyl, $C_2$-$C_6$ alkyl, allyl, substituted allyl, propargyl, cyano, formyl, acyl, substituted alkyl, substituted alkynyl, substituted ethynyl, substituted amino, or hydroxymethyl.

In a specific example, disclosed is a compound having the formula:

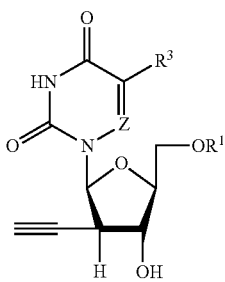

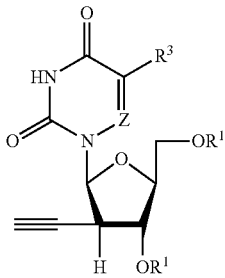

or a pharmaceutically acceptable salt thereof, wherein each R¹ is, independently, selected from one of the formula:

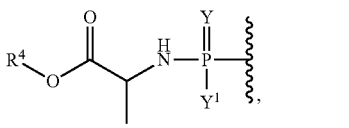

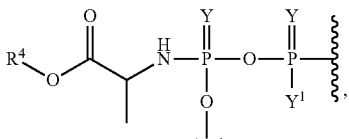

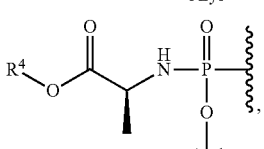

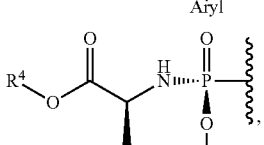

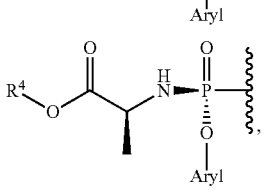

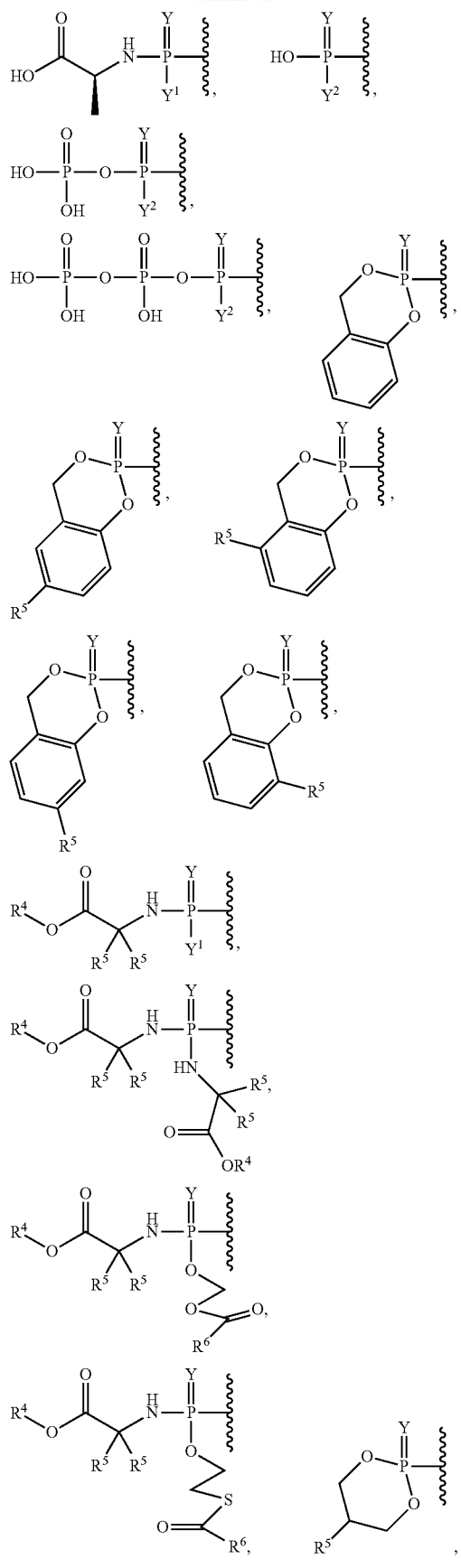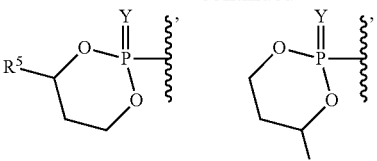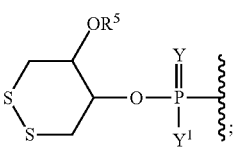

Z is N or $CR^7$;
Y is O or S;
$Y^1$ is OH, OAryl, OAlkyl, or $BH_3^-M^+$;
$Y^2$ is OH or $BH_3^-M^+$;
Aryl is phenyl, 1-naphthyl, 2-naphthyl, aromatic, heteroaromatic, 4-substituted phenyl, 4-chlorophenyl, or 4-bromophenyl;
$R^3$ is hydrogen, deuterium, methyl, fluoromethyl, difluoromethyl, trifluoromethyl, substituted methyl, $C_2$-$C_6$ alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl;
$R^4$ is hydrogen, methyl, ethyl, isopropyl, cyclopentyl, cyclohexyl, neopentyl, benzyl, alkyl, branched alkyl, cycloalkyl, or lipid;
$R^5$ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
$R^6$ is methyl, ethyl, tert-butyl, $C_{1-22}$ alkoxy, $C_{1-22}$ alkyl, branched alkyl, cycloalkyl, aryl, substituted aryl, or alkyoxy;
$R^7$ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In a specific example, disclosed is a compound having the formula:

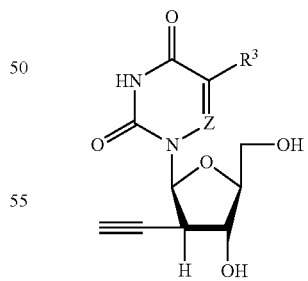

or a pharmaceutically acceptable salt thereof, wherein
Z is N or $CR^7$;
$R^3$ is hydrogen, deuterium, methyl, fluoromethyl, difluoromethyl, trifluoromethyl, substituted methyl, $C_2$-$C_6$ alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl; and R⁷ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano;

wherein R⁷ is H then R³ cannot be H; and wherein R⁷ is H then R³ cannot be hydroxymethyl.

In a specific example, disclosed is a compound having the formula:

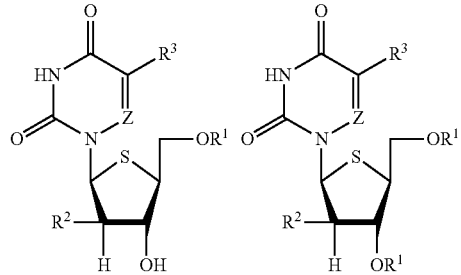

or a pharmaceutically acceptable salt thereof, wherein each R¹ is, independently, selected from one of the formula:

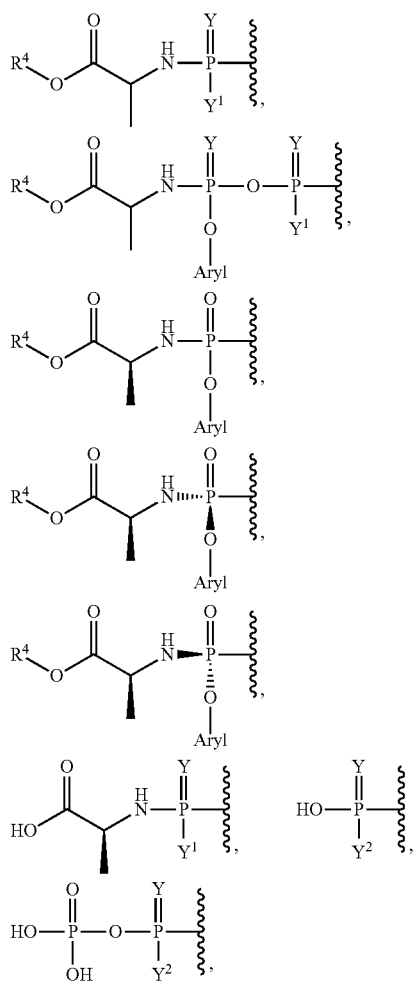

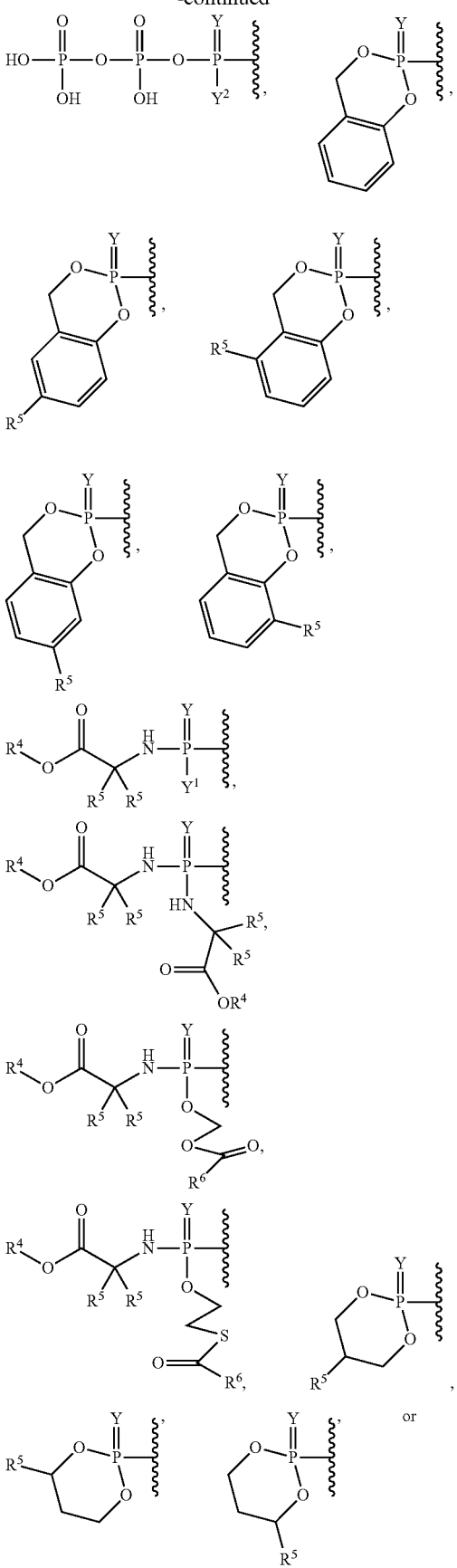

-continued

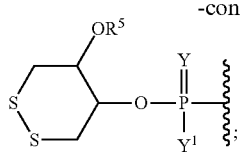

Z is N or CR²;
Y is O or S;
Y¹ is OH, OAryl, OAlkyl, or $BH_3^-M^+$;
Y² is OH or $BH_3^-M^+$
Aryl is phenyl, 1-naphthyl, 2-naphthyl, aromatic, heteroaromatic, 4-substituted phenyl, 4-chlorophenyl, or 4-bromophenyl;
R² is F, OH, alkynyl, ethynyl;
R³ is hydrogen, deuterium, methyl, fluoromethyl, difluoromethyl, trifluoromethyl, alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl;
R⁴ is hydrogen, methyl, ethyl, isopropyl, cyclopentyl, cyclohexyl, neopentyl, benzyl, alkyl, branched alkyl, cycloalkyl, or lipid;
R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;
R⁶ is methyl, ethyl, tert-butyl, $C_{1-22}$ alkoxy, $C_{1-22}$ alkyl, branched alkyl, cycloalkyl, aryl, substituted aryl, or alkyoxy; and
R⁷ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In a specific example, disclosed is a compound having the formula:

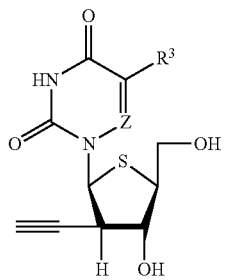

or a pharmaceutically acceptable salt thereof, wherein
Z is N or CR⁷;
R³ is hydrogen, deuterium, methyl, fluoromethyl, difluoromethyl, trifluoromethyl, alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl; and
R⁷ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano,
wherein R³ is H then R⁷ cannot be H.

In a specific example, disclosed is a compound having the formula:

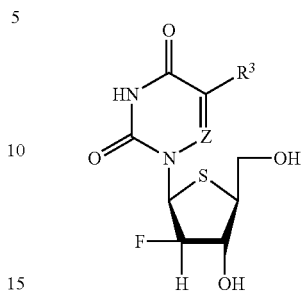

or a pharmaceutically acceptable salt thereof, wherein
Z is N or CR⁷;
R³ is hydrogen, deuterium, methyl, fluoromethyl, difluoromethyl, trifluoromethyl, alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl; and
R⁷ is H, D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano,
wherein R³ is methyl then R⁷ cannot be H.

In a specific example, disclosed is a compound having the formula:

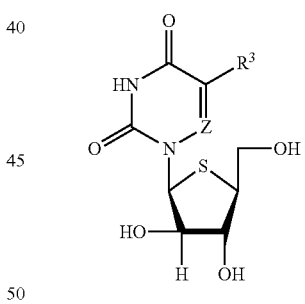

or a pharmaceutically acceptable salt thereof, wherein
Z is N or CR⁷;
R³ is hydrogen, deuterium, methyl, fluoromethyl, difluoromethyl, trifluoromethyl, alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl; and
R⁷ is D, hydroxyl, thiol, amino, alkyl, methyl, fluoromethyl, difluoromethyl, trifluoromethyl, hydroxymethyl, alkenyl, alkynyl, ethynyl, azido, halo, fluoro, chloro, bromo, iodo, acyl, esteryl, formyl, alkoxy, substituted amino, or cyano.

In a specific example, disclosed is a compound having the formula:

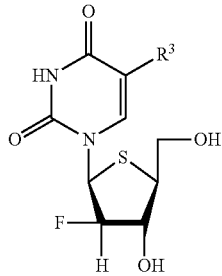

or a pharmaceutically acceptable salt thereof, wherein

R³ is deuterium, fluoromethyl, difluoromethyl, trifluoromethyl, alkyl, alkenyl, alkynyl, amino, bromo, iodo, hydroxyl, cyano, formyl, acyl, substituted alkyl, substituted alkenyl, substituted alkynyl, substituted amino, or hydroxymethyl.

Compounds Being Disclosed:

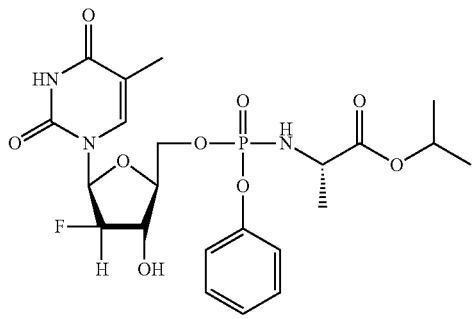

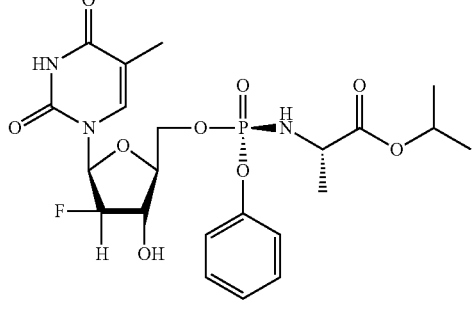

(S,S)

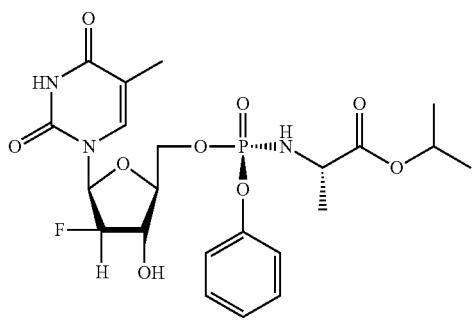

(S,R)

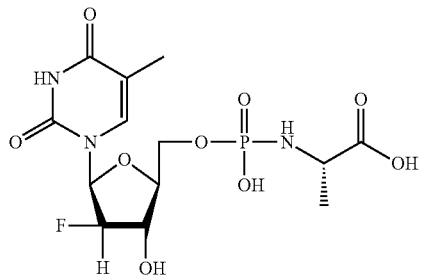

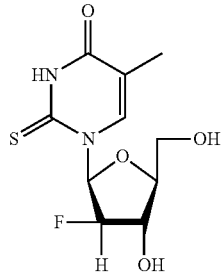

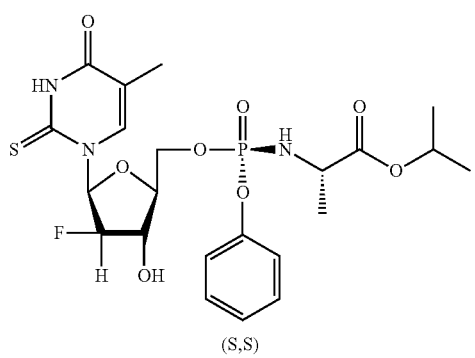

(S,S)

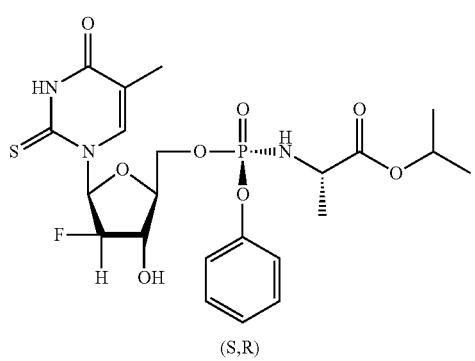

(S,R)

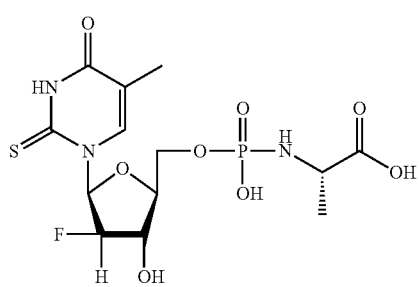

-continued

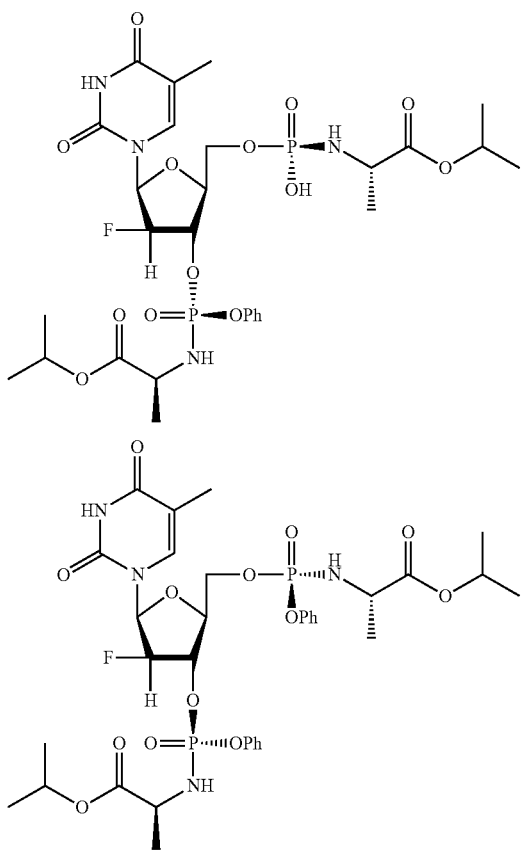

or a pharmaceutically acceptable salt thereof.

In a specific example, disclosed is a compound having the formula:

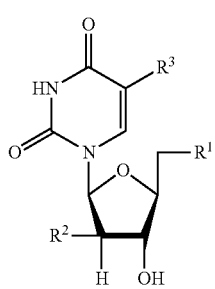

or a pharmaceutically acceptable salt thereof, wherein R¹ is one of the formula:

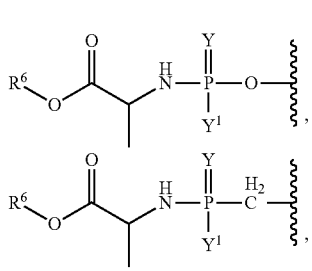

-continued

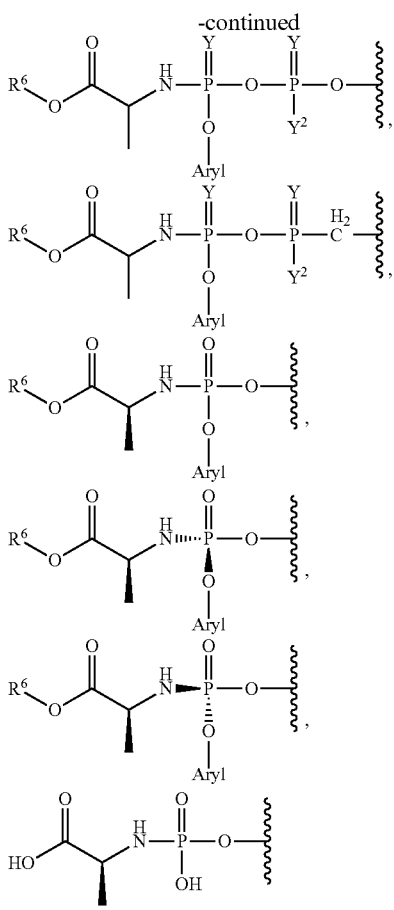

Y is O or S;
Y¹ is OAryl, OAlkyl, or $BH_3^-M^+$;
Y² is OH, OAryl, OAlkyl, or $BH_3^-M^+$;
Aryl is phenyl, 1-naphthyl, 2-naphthyl, aromatic, heteroaromatic, 4-substituted phenyl, 4-chlorophenyl, or 4-bromophenyl;
R⁶ is alkyl, alkenyl, alkynyl, branched alkyl, phenyl, benzyl, carbocyclyl, aryl, or heterocyclyl;
R² is F or OH; and
R³ is hydrogen, deuterium, methyl, trifluoromethyl, alkyl, alkenyl, alkynyl, halogen, hydroxyl, cyano, formyl, acyl, substituted alkyl, substituted alkenyl, substituted alkynyl, or hydroxymethyl.

In another specific example, disclosed is a compound having the formula:

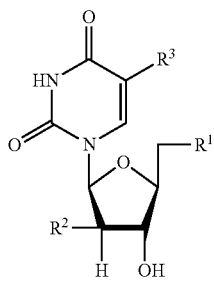

or a pharmaceutically acceptable salt thereof, wherein $R^1$ is hydroxyl or is selected from one of the formula:

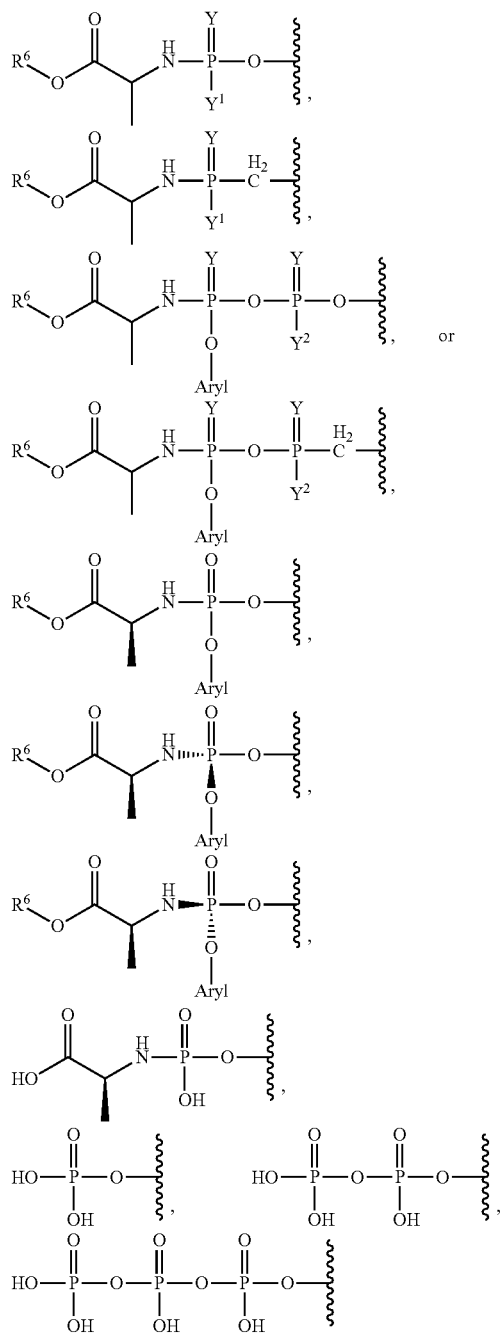

Y is O or S;
Y$^1$ is OAryl, OAlkyl or BH$_3$$^-$M$^+$;
Y$^2$ is OH, OAryl, OAlkyl or BH$_3$$^-$M$^+$;
Aryl is phenyl, 1-naphthyl, 2-naphthyl, aromatic, heteroaromatic, 4-substituted phenyl, 4-chlorophenyl, or 4-bromophenyl;
R$^6$ is alkyl, alkenyl, alkynyl, branched alkyl, phenyl, benzyl, carbocyclyl, aryl, or heterocyclyl;
R$^2$ is D, Cl, Br, I, methyl, triflouromethyl, cyano, alkyl, alkenyl, alkynyl, substituted alkyl, substituted alkenyl, substituted alkynyl, alkoxy, ethnyl, hydroxymethyl, fluoromethyl, difluoromethyl, formyl, acyl, amino, azido, thiol, hydroxyamino, or substituted thio; and R$^3$ is hydrogen, deuterium, methyl, trifluoromethyl, alkyl, alkenyl, alkynyl, halogen, hydroxyl, cyano, formyl, acyl, substituted alkyl, substituted alkenyl, substituted alkynyl, or hydroxymethyl.

In further specific examples, disclosed are a compound having the formula:

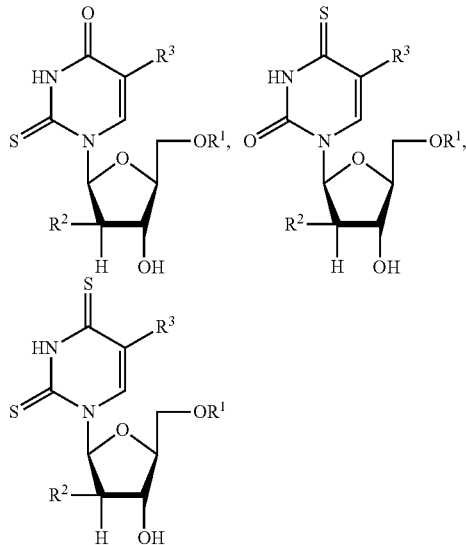

or a pharmaceutically acceptable salt thereof, wherein R$^1$ is hydrogen or selected from one of the formula:

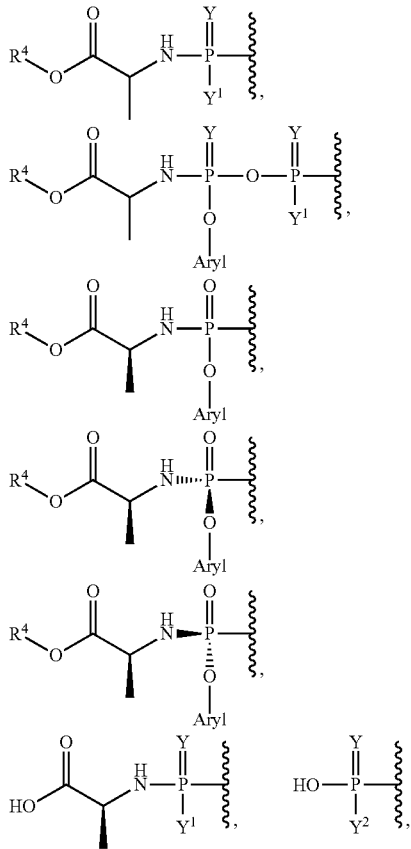

-continued

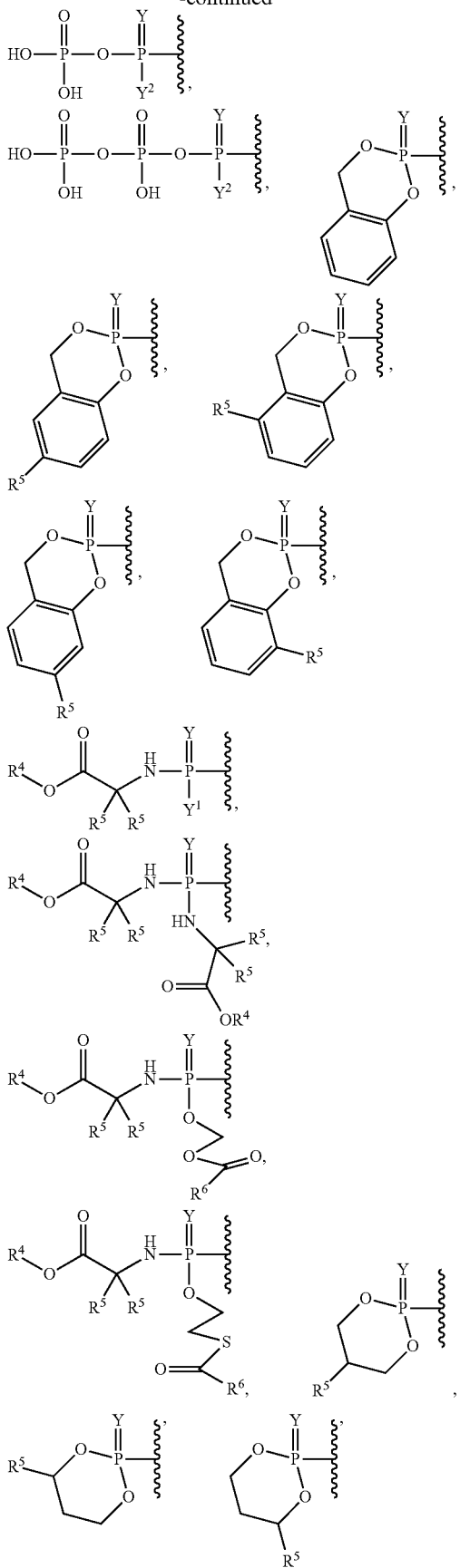

-continued

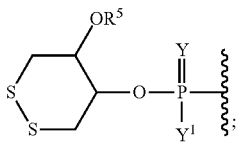

Y is O or S;

Y¹ is OH, OAryl, OAlkyl, or $BH_3^-M^+$;

Y² is OH or $BH_3^-M^+$

Aryl is phenyl, 1-naphthyl, 2-naphthyl, aromatic, heteroaromatic, 4-substituted phenyl, 4-chlorophenyl, or 4-bromophenyl;

R² is D, F, Cl, Br, I, hydroxyl, methyl, triflouromethyl, cyano, alkyl, alkenyl, alkynyl, substituted alkyl, substituted alkenyl, substituted alkynyl, alkoxy, ethnyl, hydroxymethyl, fluoromethyl, difluoromethyl, formyl, acyl, amino, substituted amino, azido, thiol, hydroxyamino, or substituted thio; and R³ is hydrogen, deuterium, methyl, fluoromethyl, difluoromethyl, trifluoromethyl, alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl;

R⁴ is hydrogen, methyl, ethyl, isopropyl, cyclopentyl, cyclohexyl, neopentyl, benzyl, alkyl, branched alkyl, cycloalkyl, or lipid;

R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

R⁶ is methyl, ethyl, tert-butyl, $C_{1-22}$ alkoxy, $C_{1-22}$ alkyl, branched alkyl, cycloalkyl, aryl, substituted aryl, or alkyoxy.

In further specific examples, disclosed are a compound having the formula:

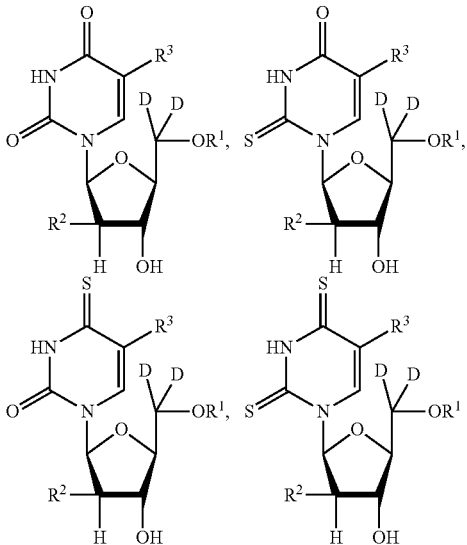

or a pharmaceutically acceptable salt thereof, wherein

R¹ is hydrogen or selected from one of the formula:

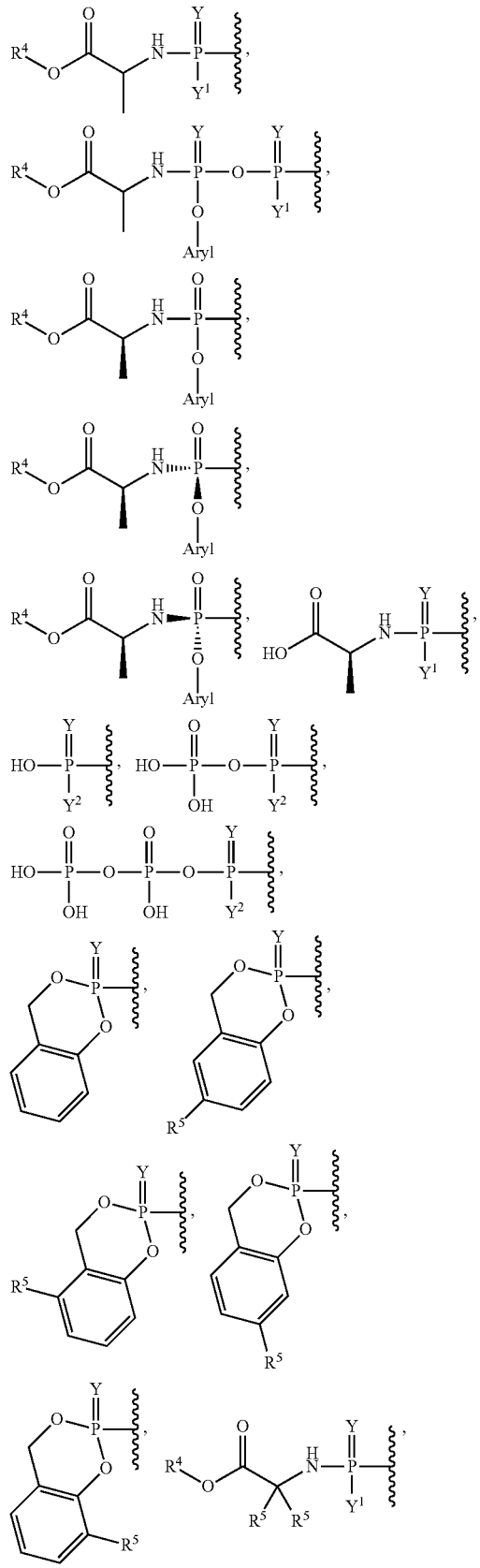

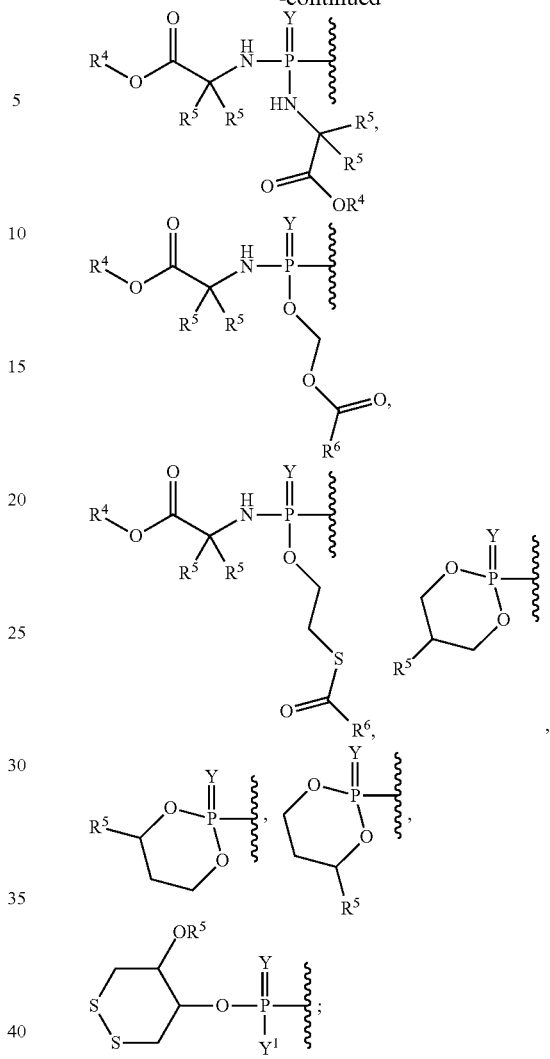

Y is O or S;
Y¹ is OH, OAryl, OAlkyl, or $BH_3^- M^+$;
Y² is OH or $BH_3^- M^{30}$
Aryl is phenyl, 1-naphthyl, 2-naphthyl, aromatic, heteroaromatic, 4-substituted phenyl, 4-chlorophenyl, or 4-bromophenyl;
R² is D, F, Cl, Br, I, hydroxyl, methyl, triflouromethyl, cyano, alkyl, alkenyl, alkynyl, substituted alkyl, substituted alkenyl, substituted alkynyl, alkoxy, ethnyl, hydroxymethyl, fluoromethyl, difluoromethyl, formyl, acyl, amino, substituted amino, azido, thiol, hydroxyamino, or substituted thio; and
R³ is hydrogen, deuterium, methyl, fluoromethyl, difluoromethyl, trifluoromethyl, alkyl, alkenyl, alkynyl, amino, fluoro, chloro, bromo, iodo, hydroxyl, cyano, formyl, acyl, substituted alkyl, substituted alkenyl, substituted alkynyl, substituted amino, or hydroxymethyl;
R⁴ is hydrogen, methyl, ethyl, isopropyl, cyclopentyl, cyclohexyl, neopentyl, benzyl, alkyl, branched alkyl, cycloalkyl, or lipid;
R⁵ is hydrogen, deuterium, hydroxyl, cyano, azido, amino, substituted amino, aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl;

$R^6$ is methyl, ethyl, tert-butyl, $C_{1-22}$ alkoxy, $C_{1-22}$ alkyl, branched alkyl, cycloalkyl, aryl, substituted aryl, or alkyoxy.
In exemplary embodiments, the compound is selected from:
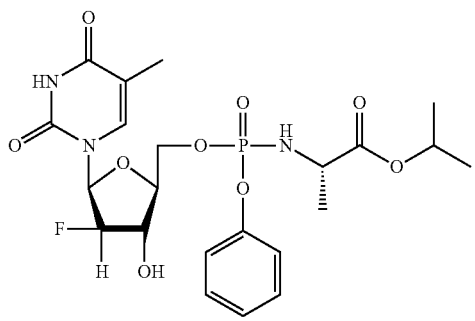
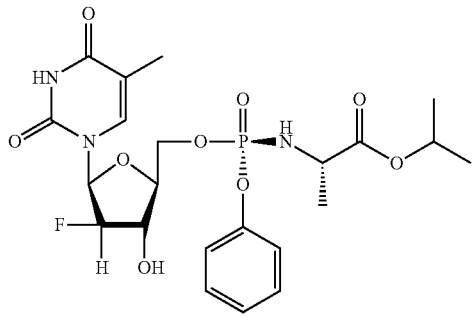
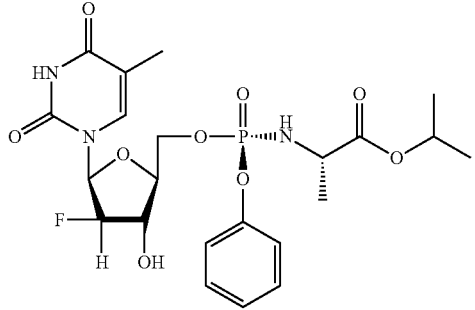
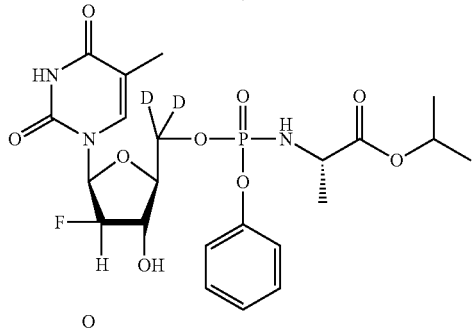
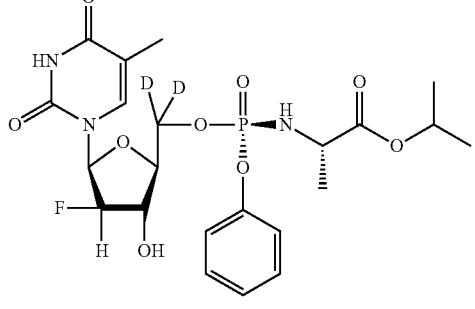
-continued
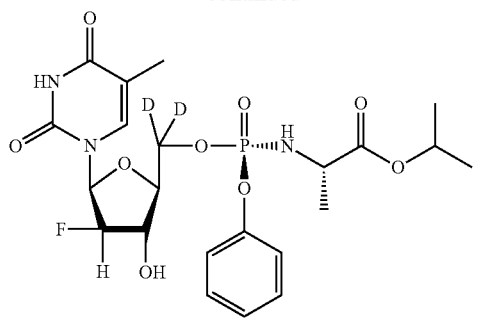
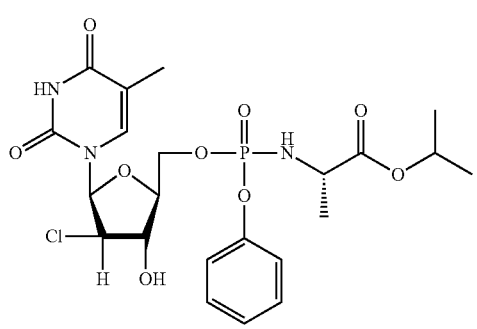
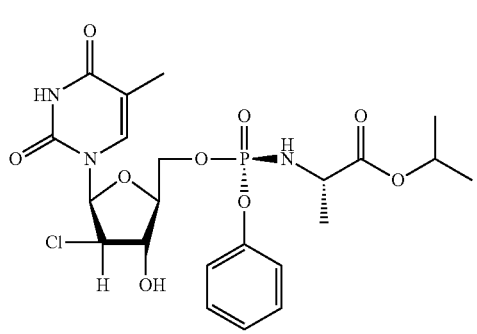
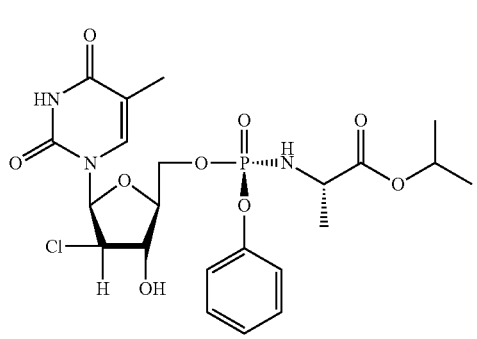
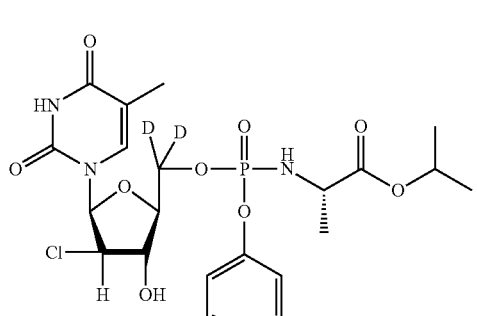

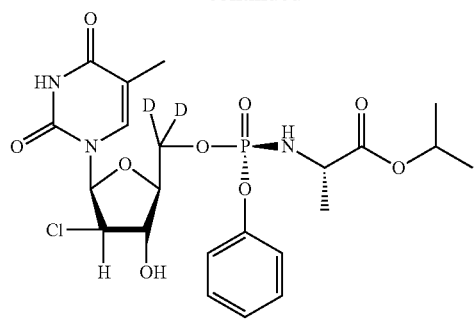
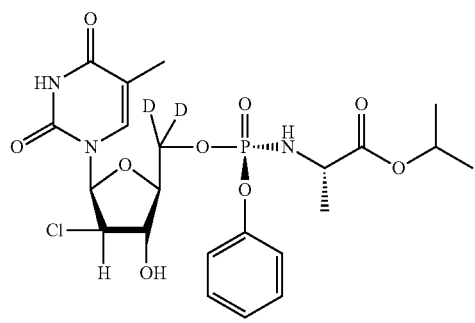
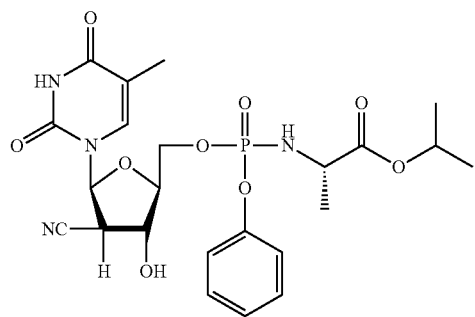
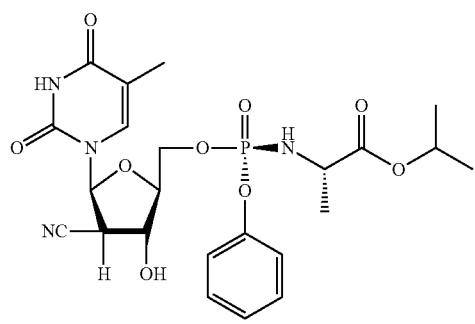
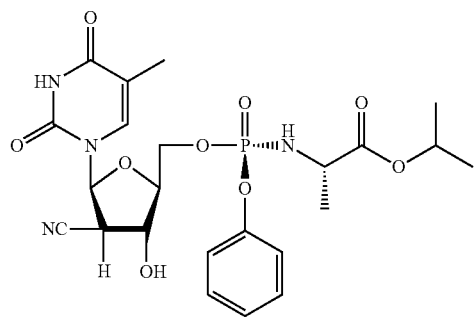
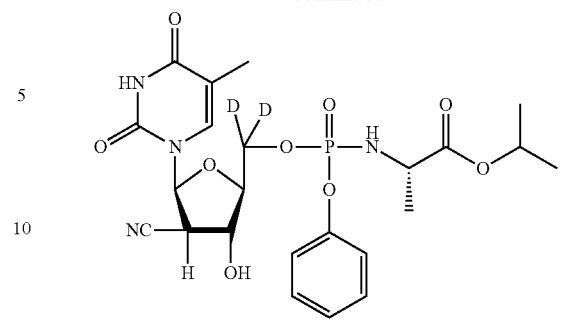
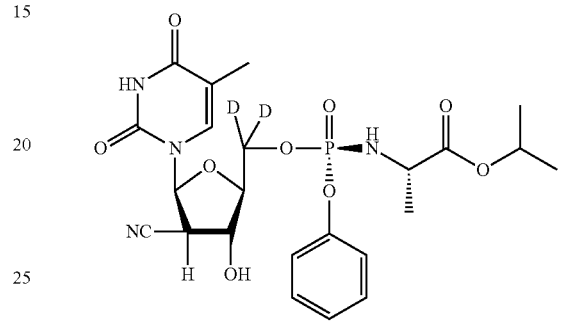
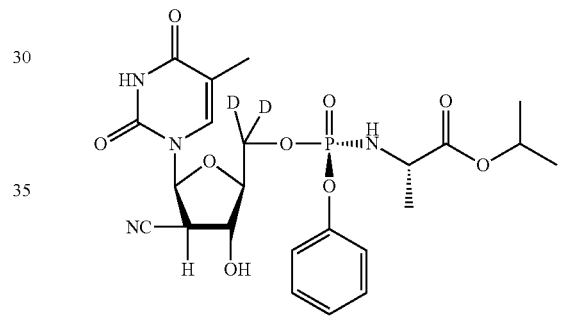
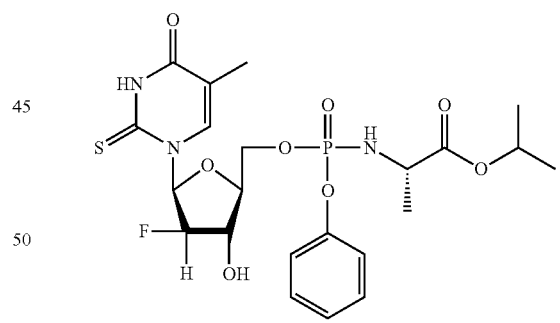

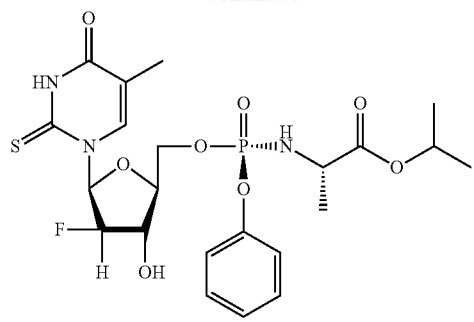
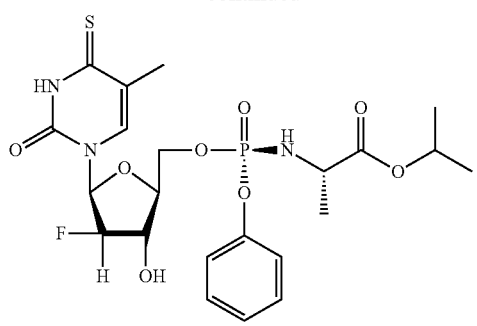
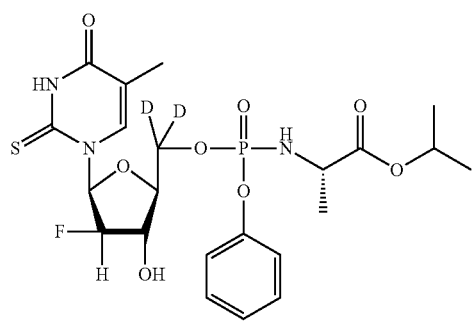
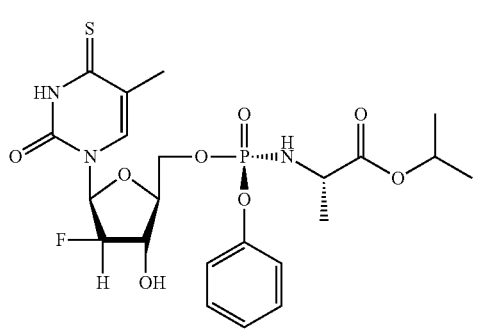
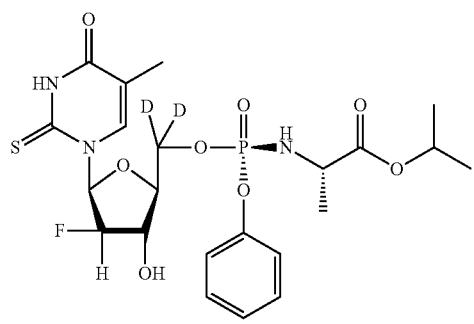
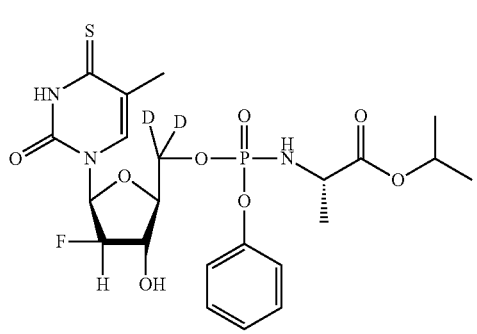
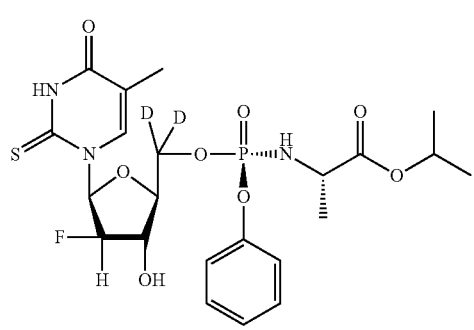
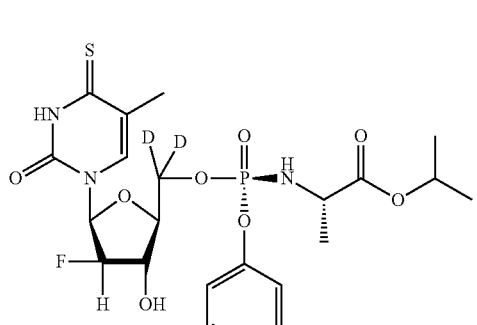
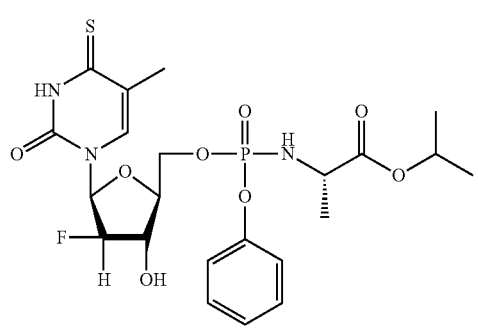
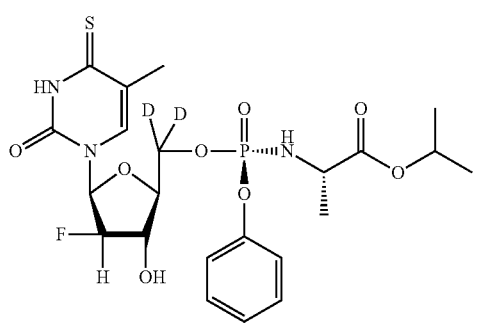

51
-continued
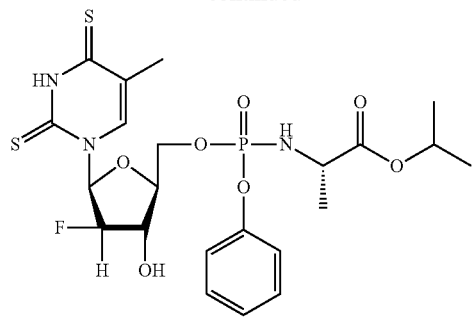
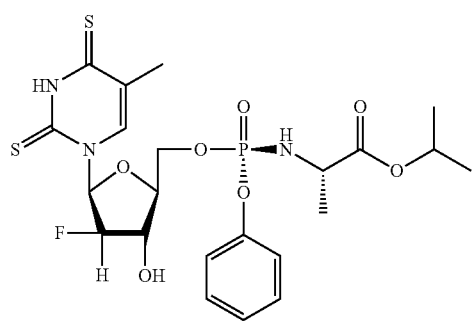
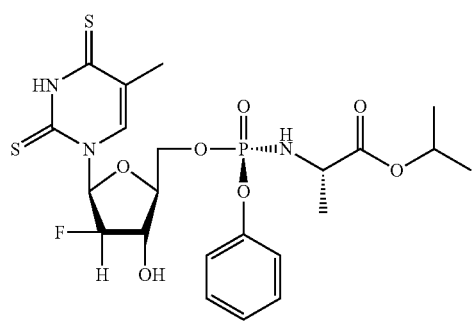
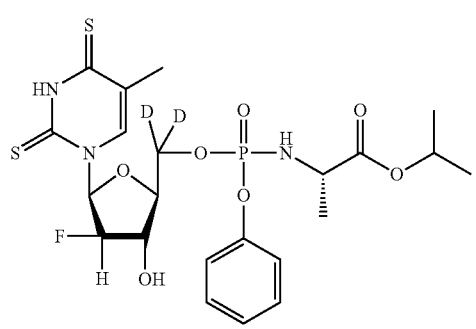
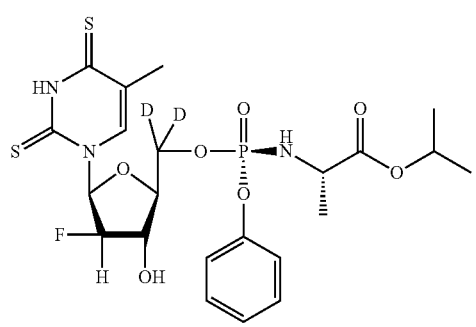
52
-continued
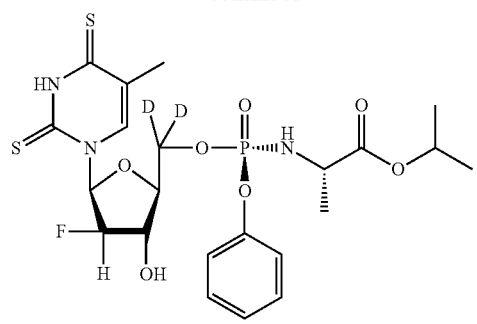
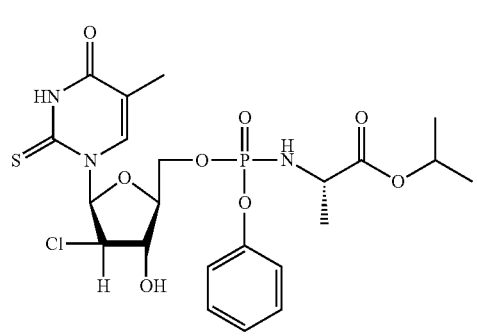
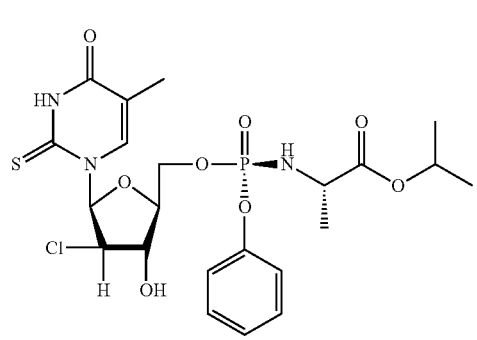
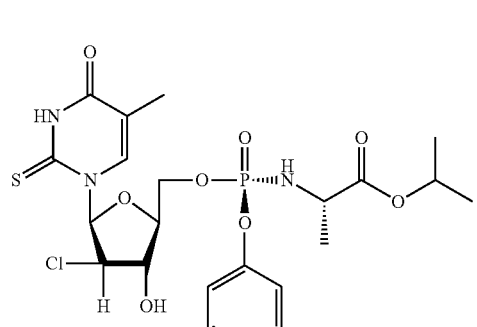
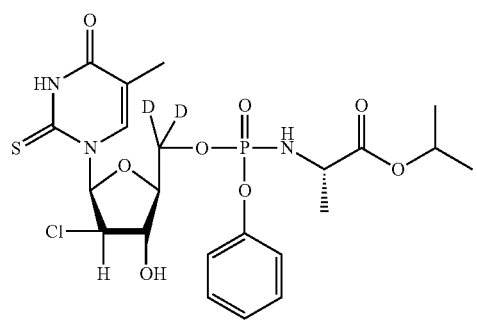

53
-continued
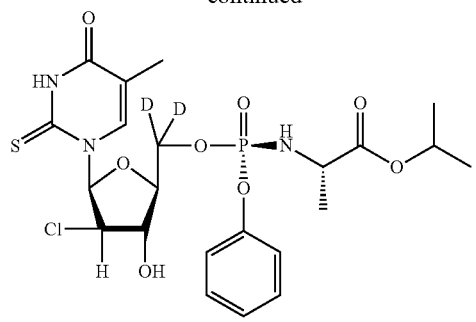
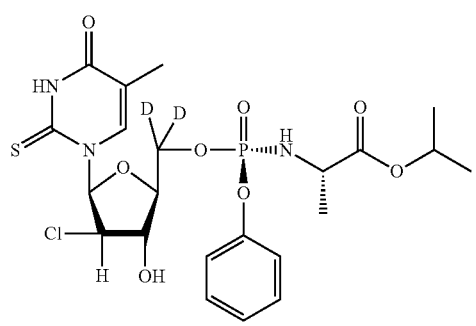
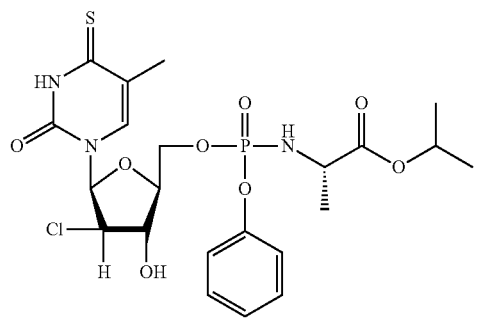
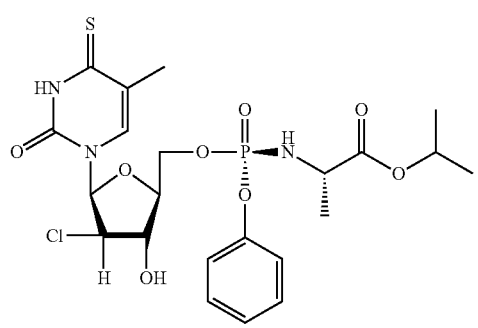
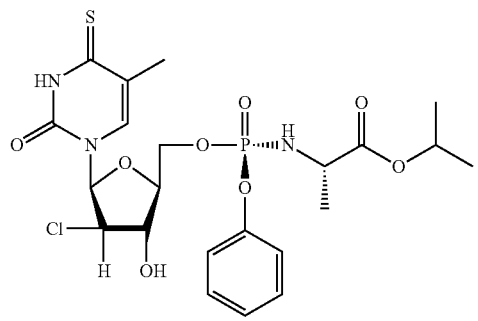
54
-continued
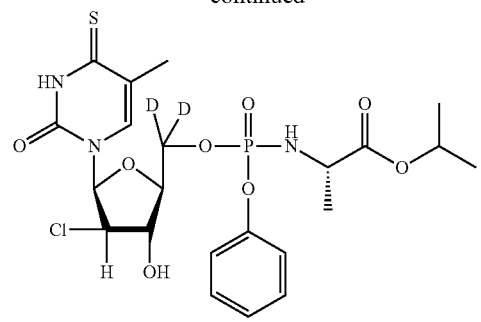
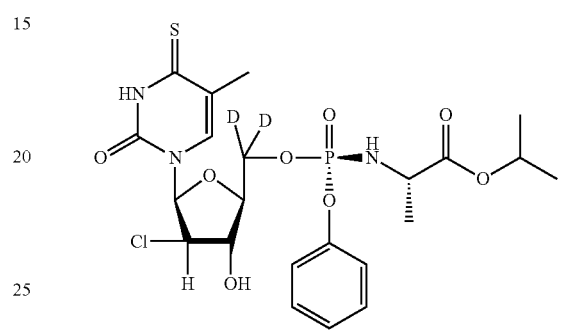
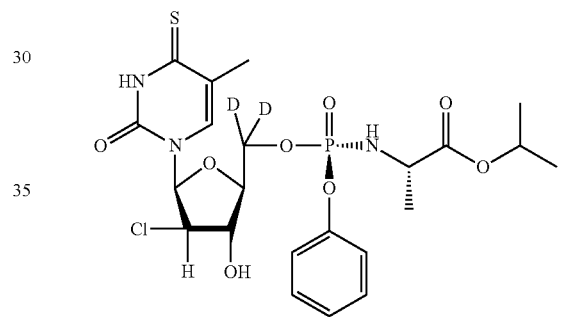
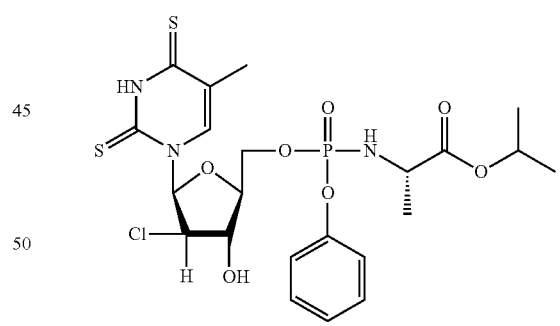
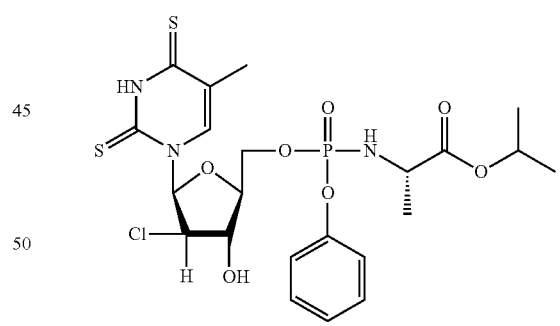

55
-continued
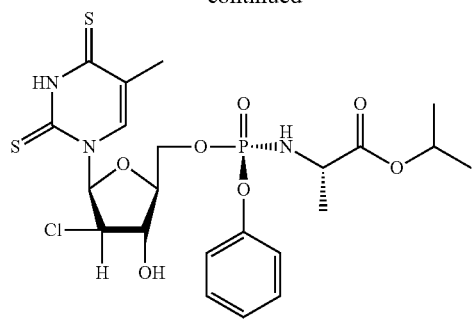
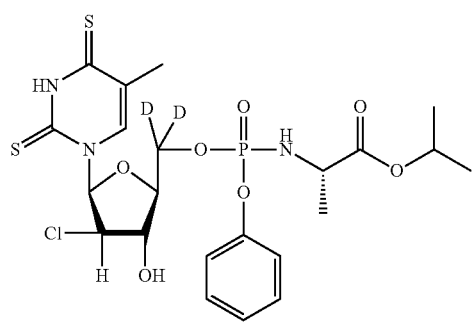
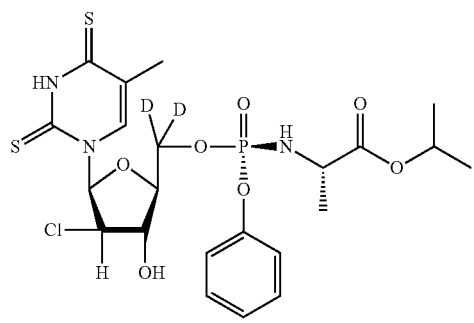
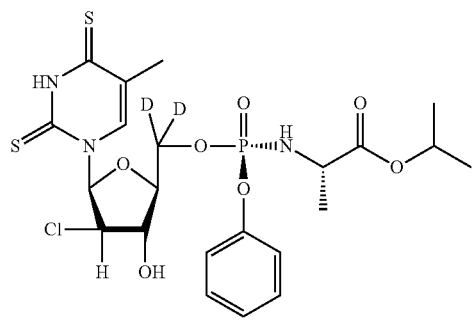
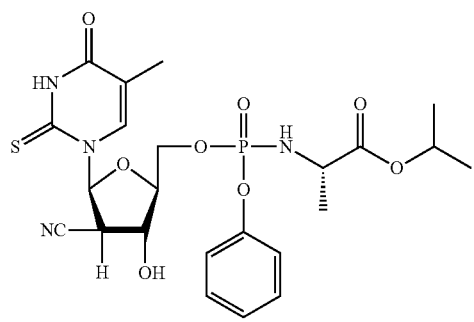
56
-continued
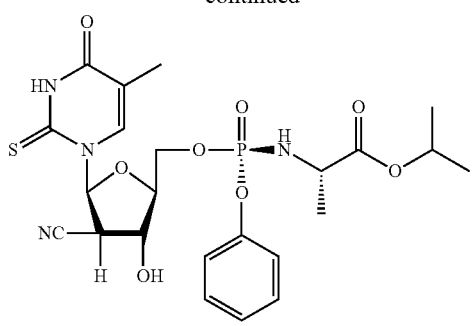
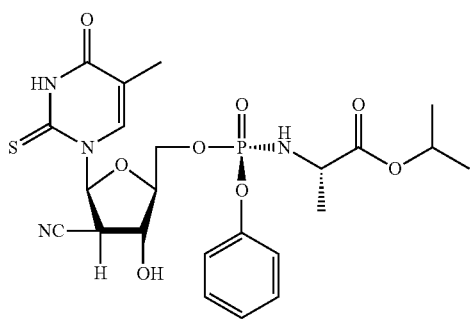
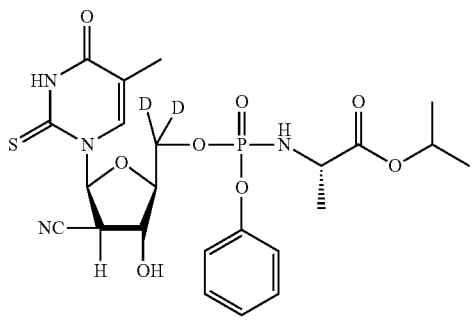
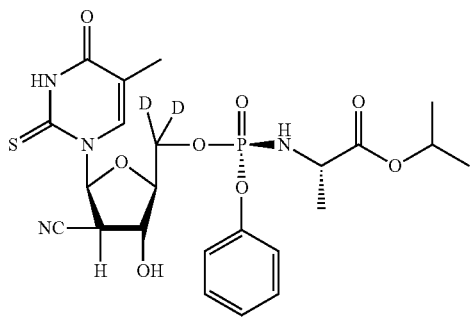
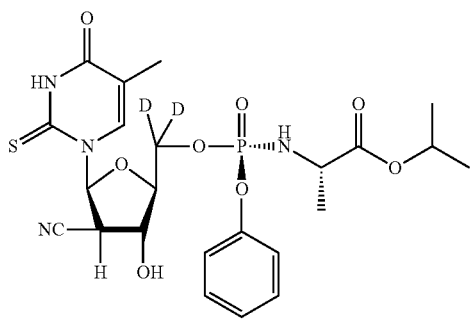

57
-continued
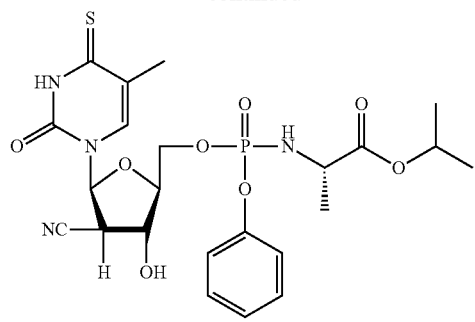
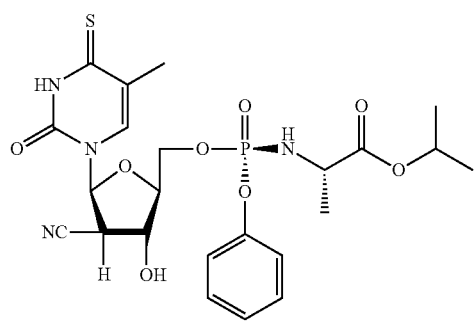
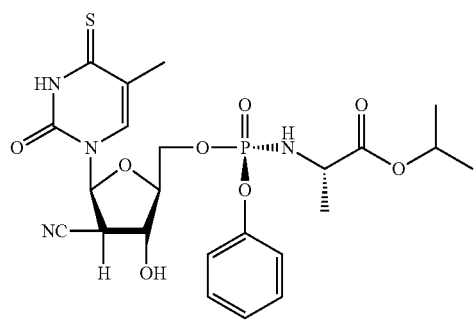
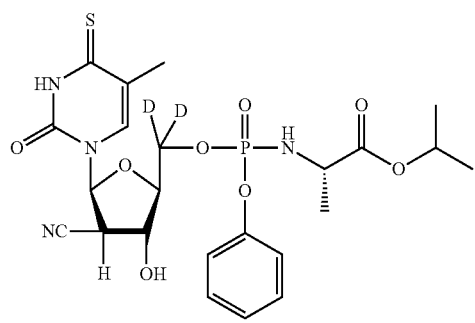
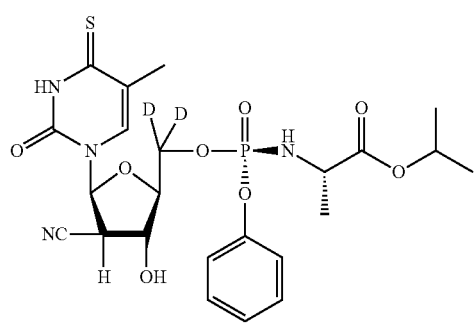
58
-continued
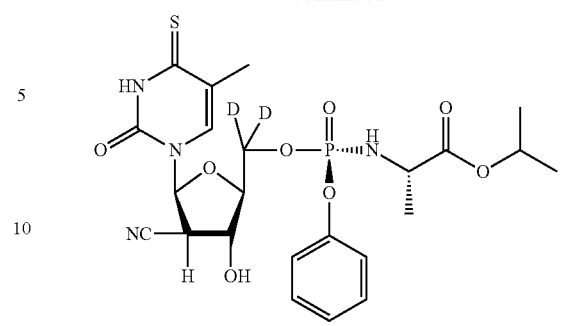
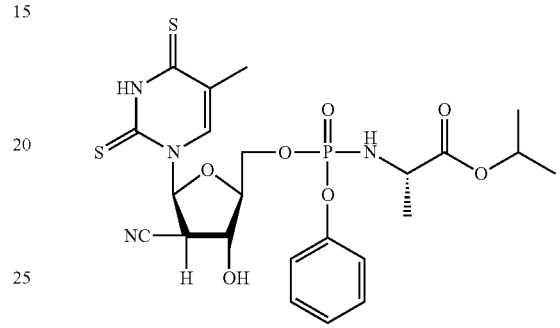
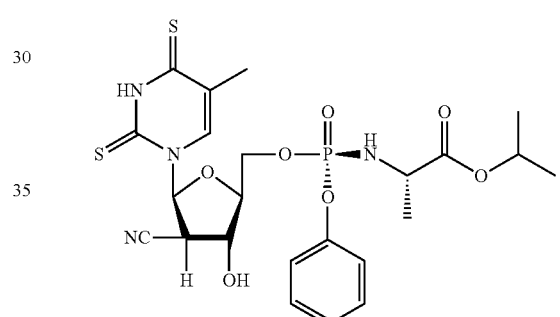
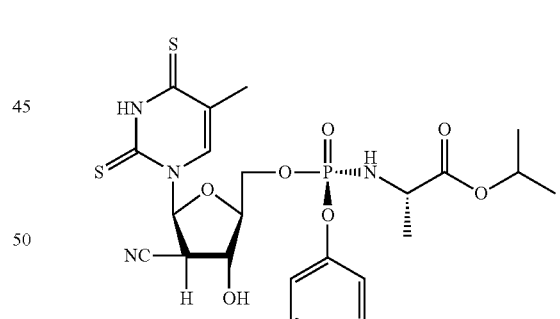
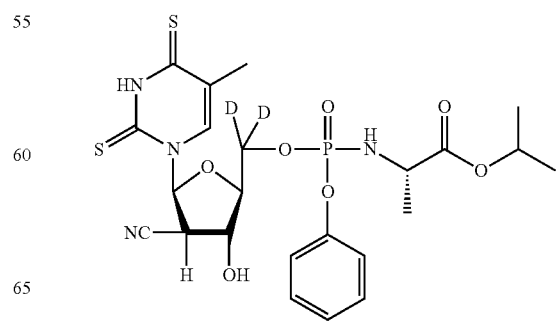

59
-continued
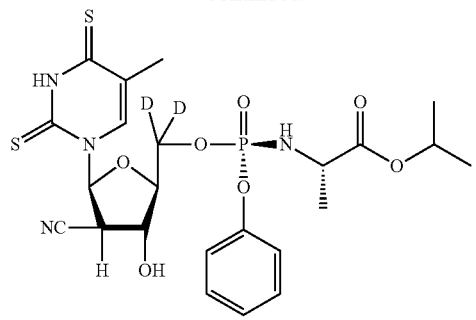
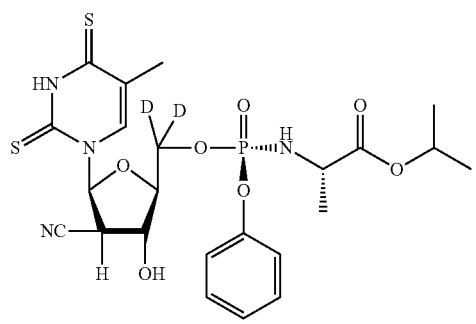
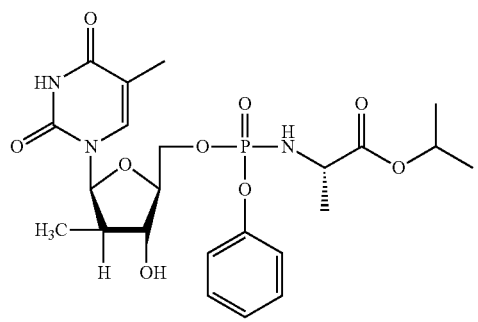
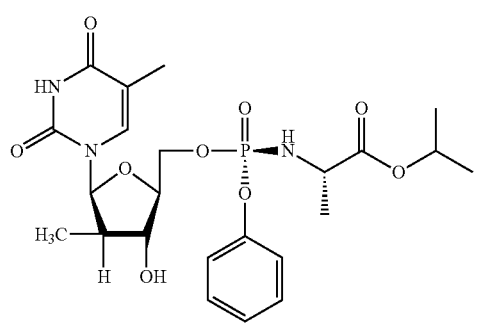
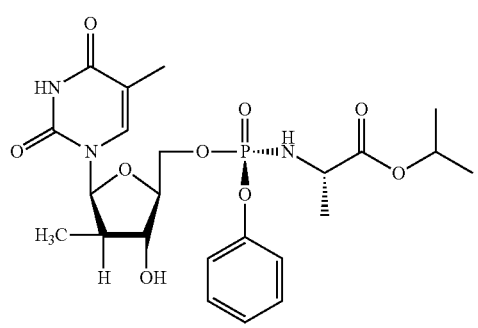
60
-continued
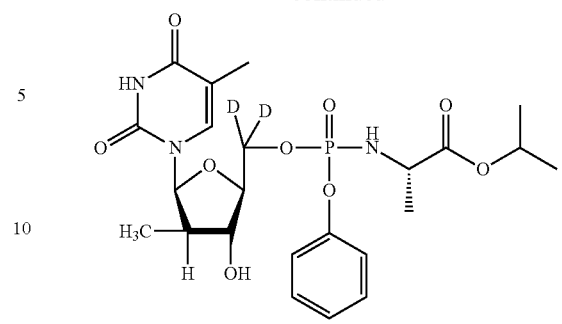
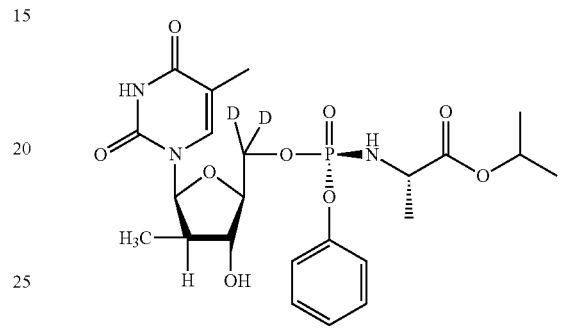
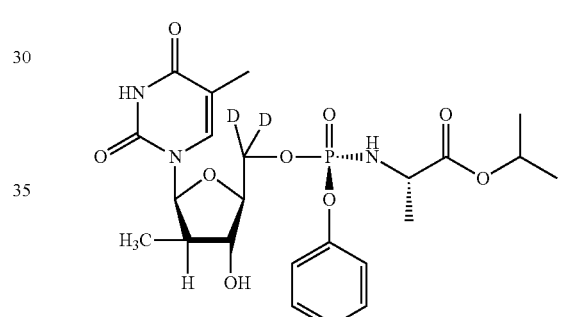
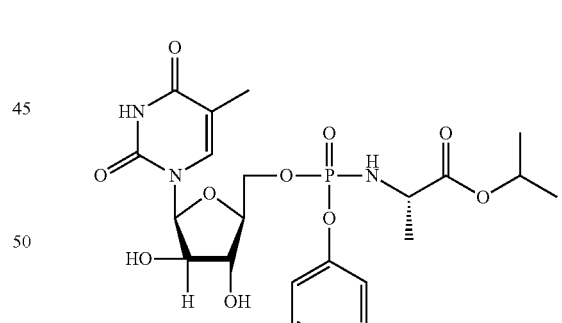
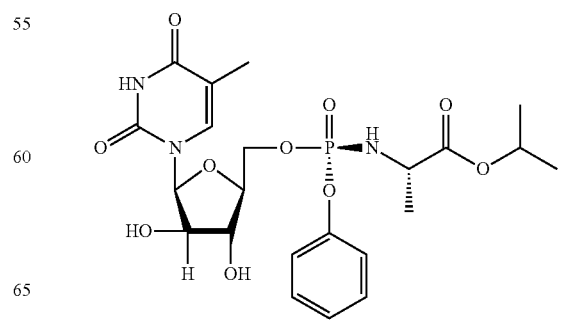

61
-continued
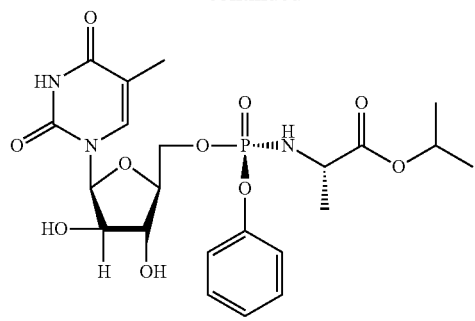
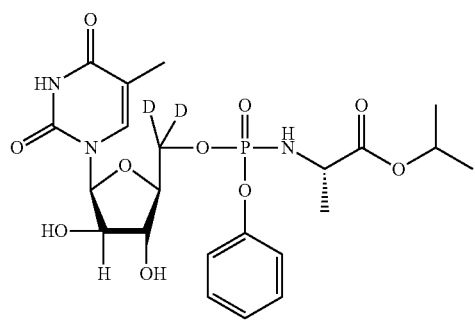
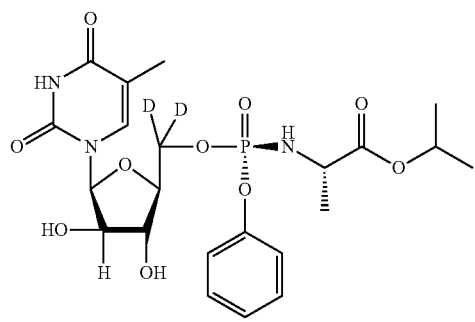
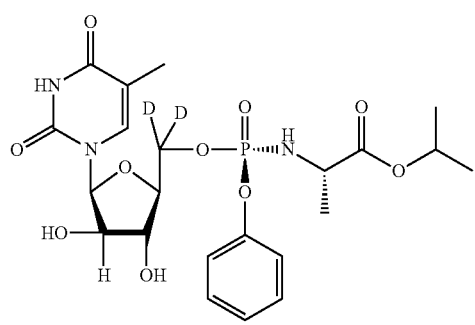
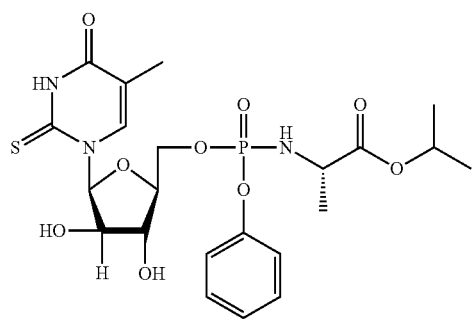
62
-continued
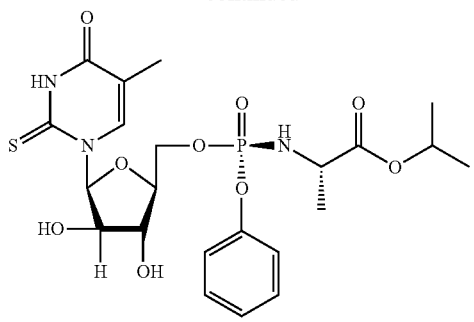
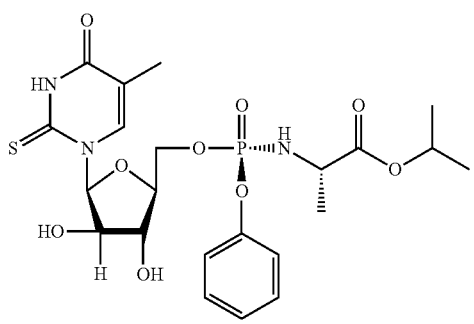
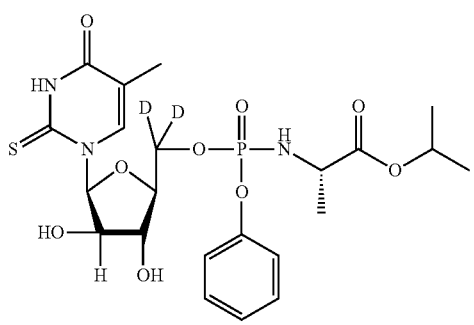
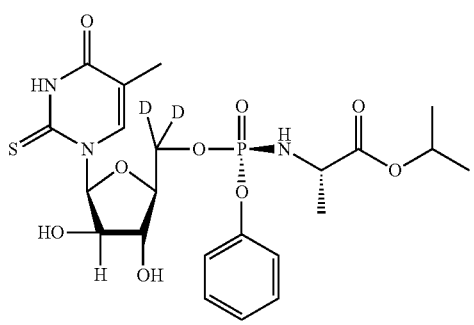
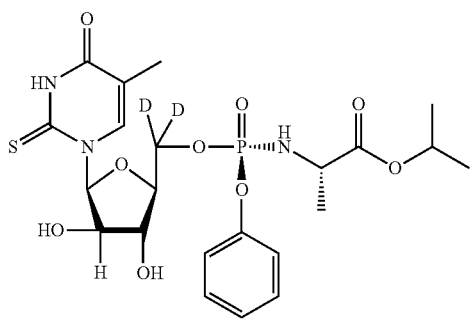

63
-continued
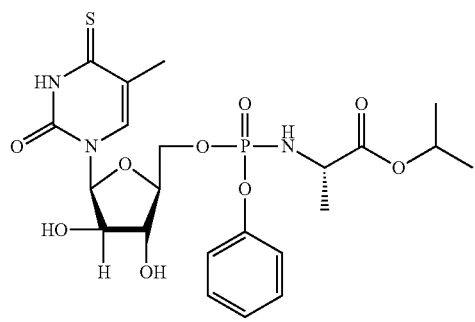
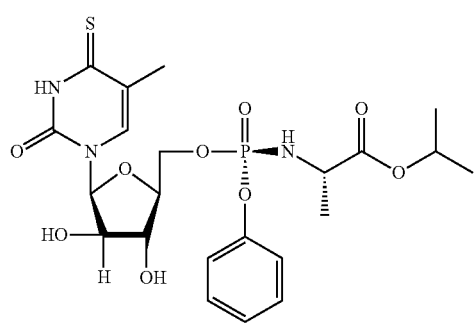
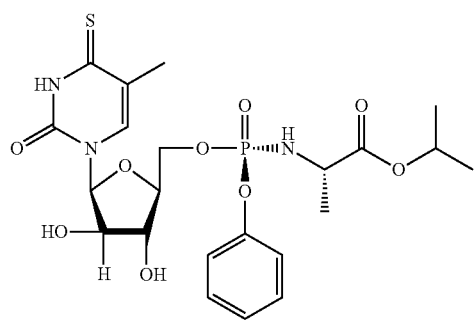
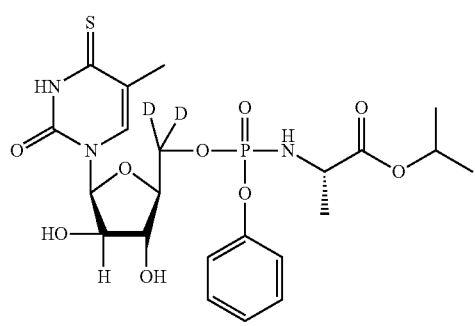
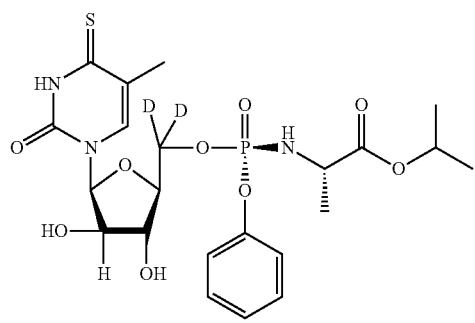
64
-continued
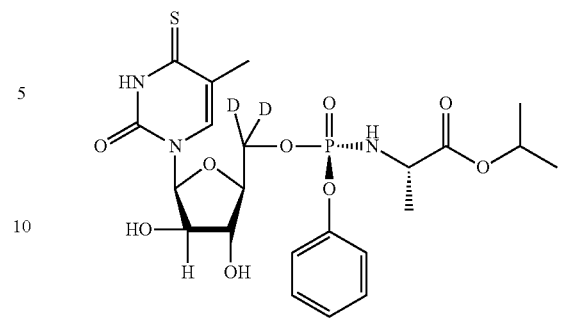
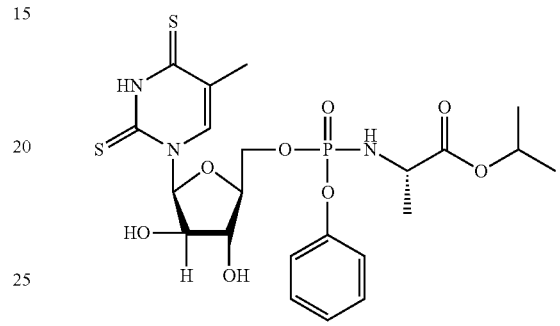
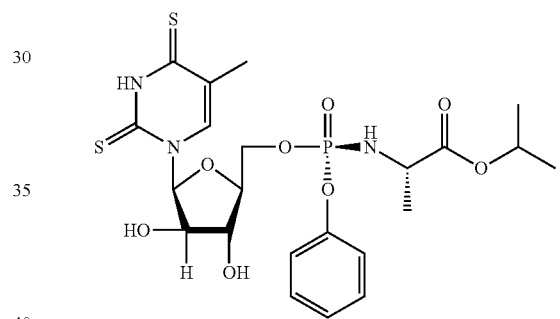
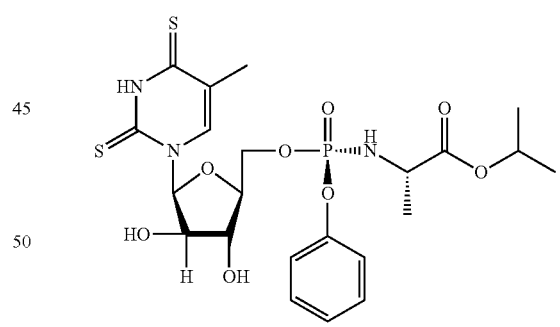
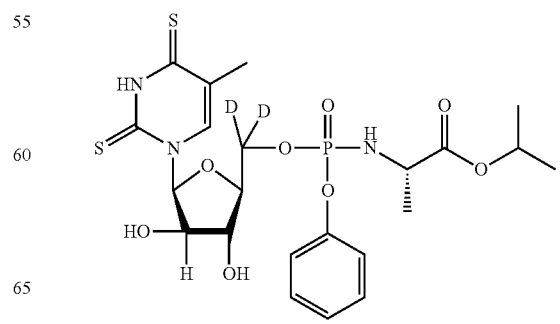

65
-continued
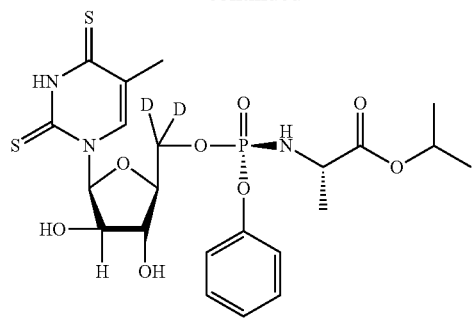
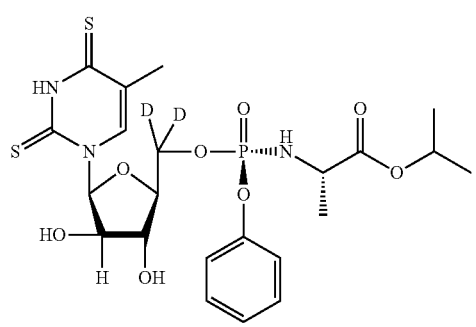
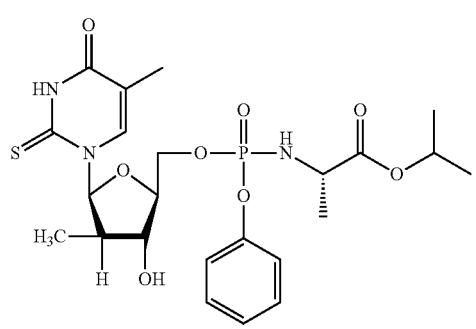
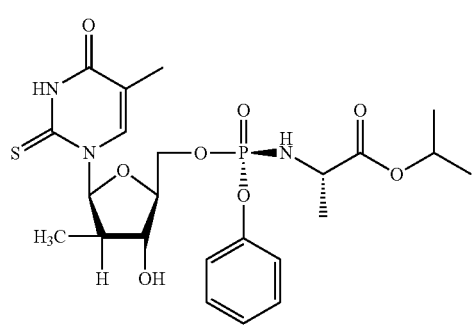
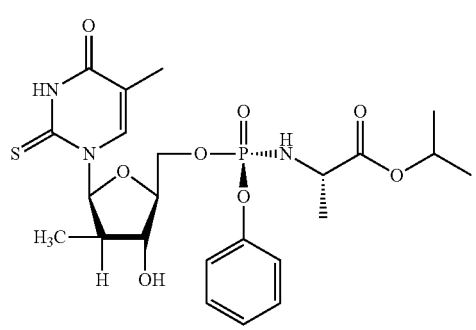
66
-continued
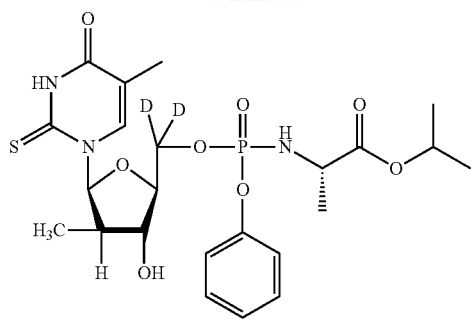
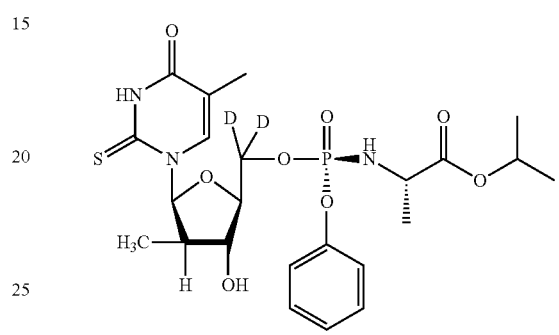
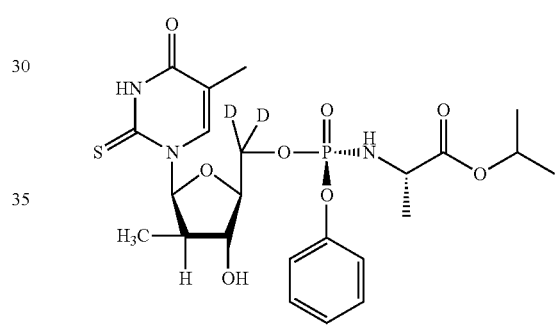
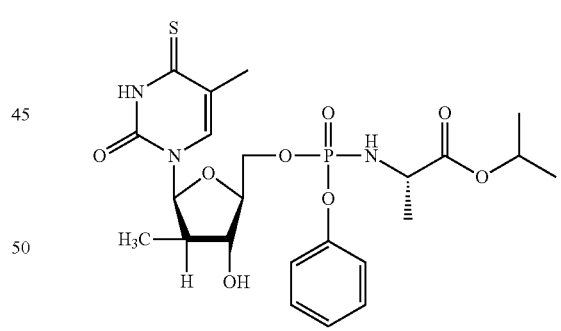
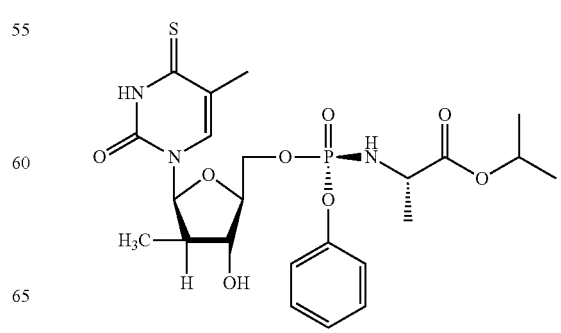

67
-continued
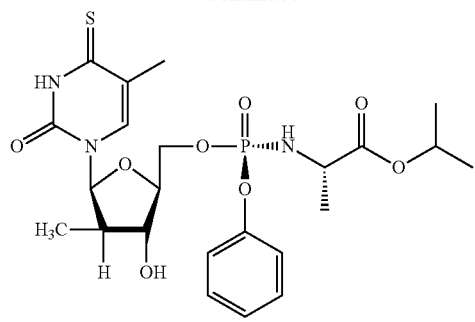
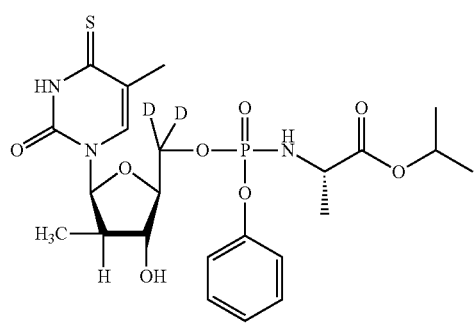
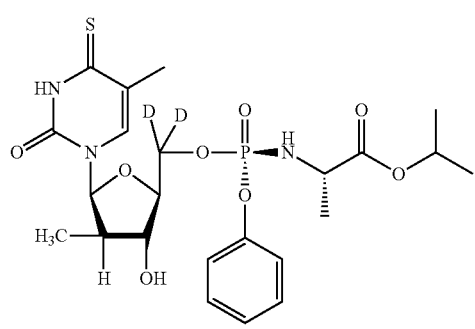
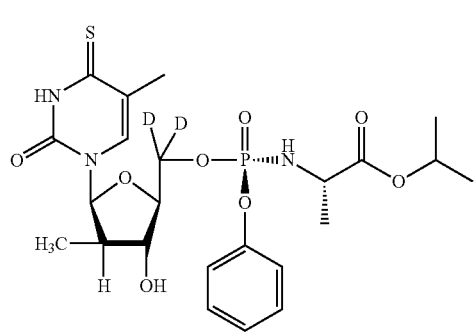
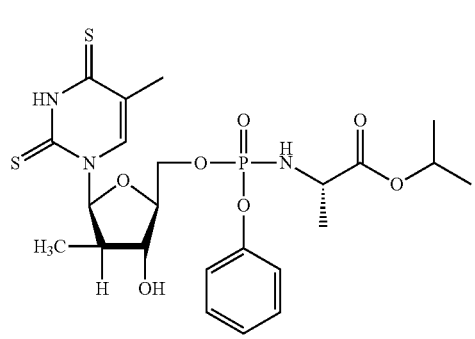
68
-continued
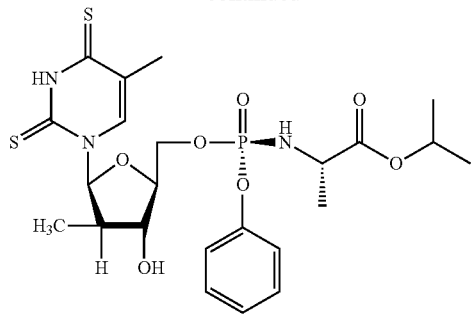
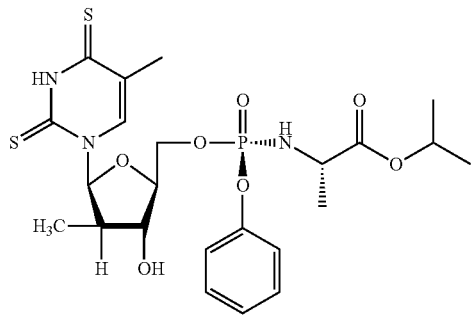
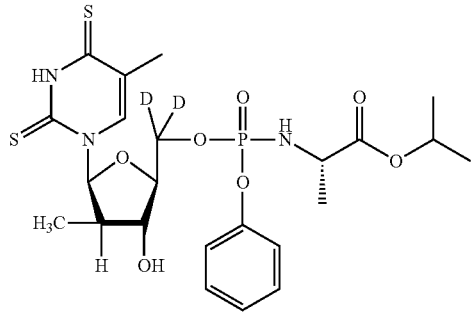
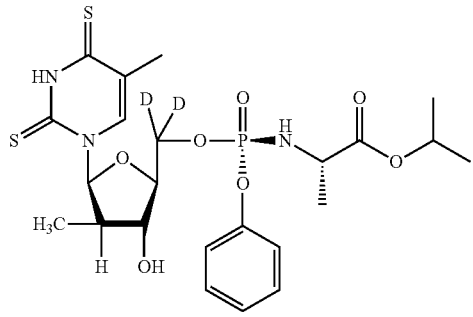
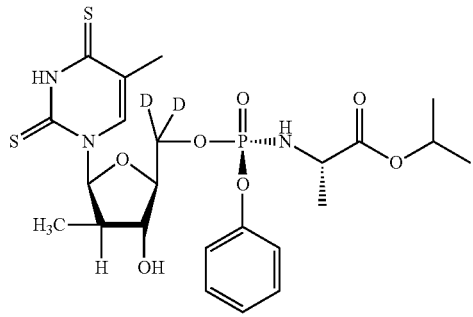

In exemplary embodiments, the compound is selected from:
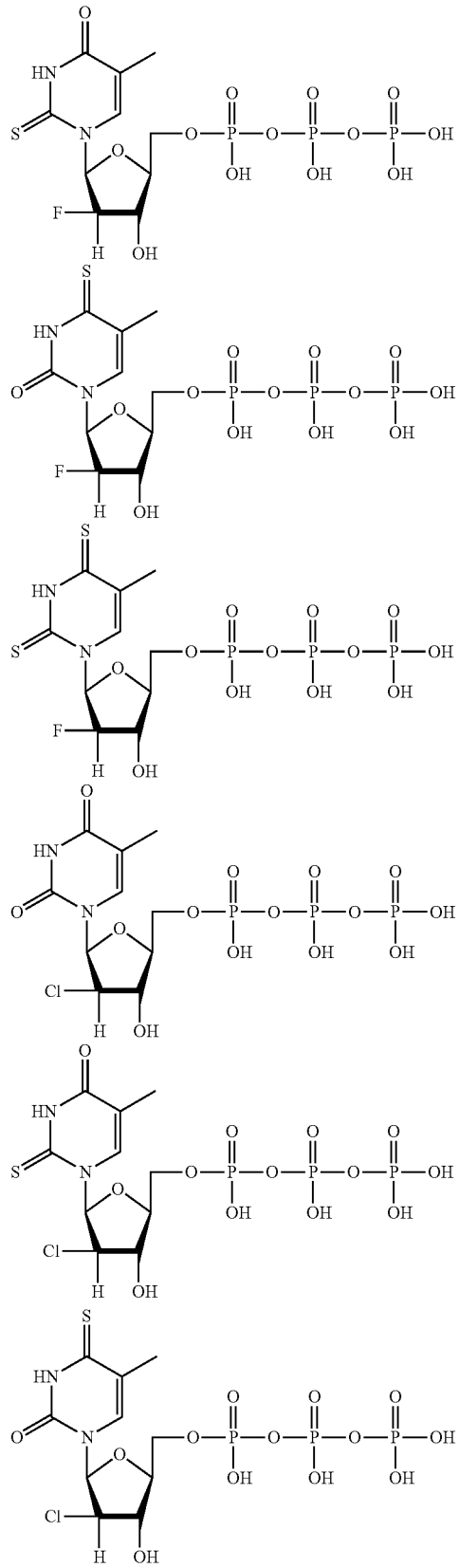
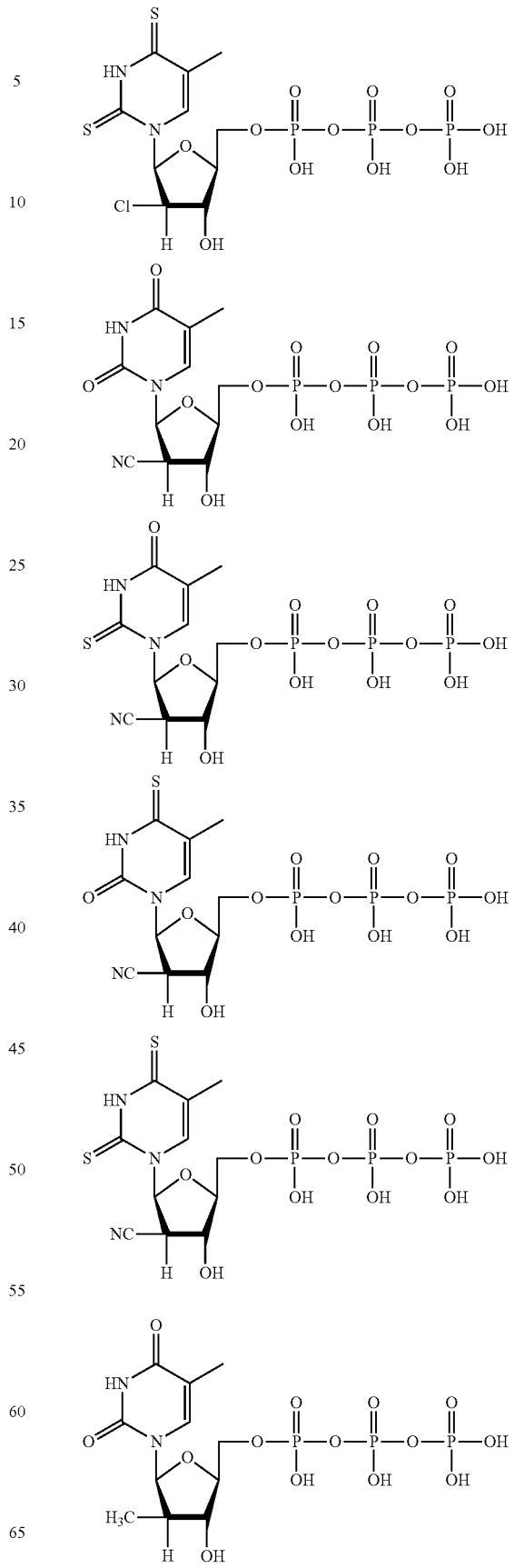

-continued
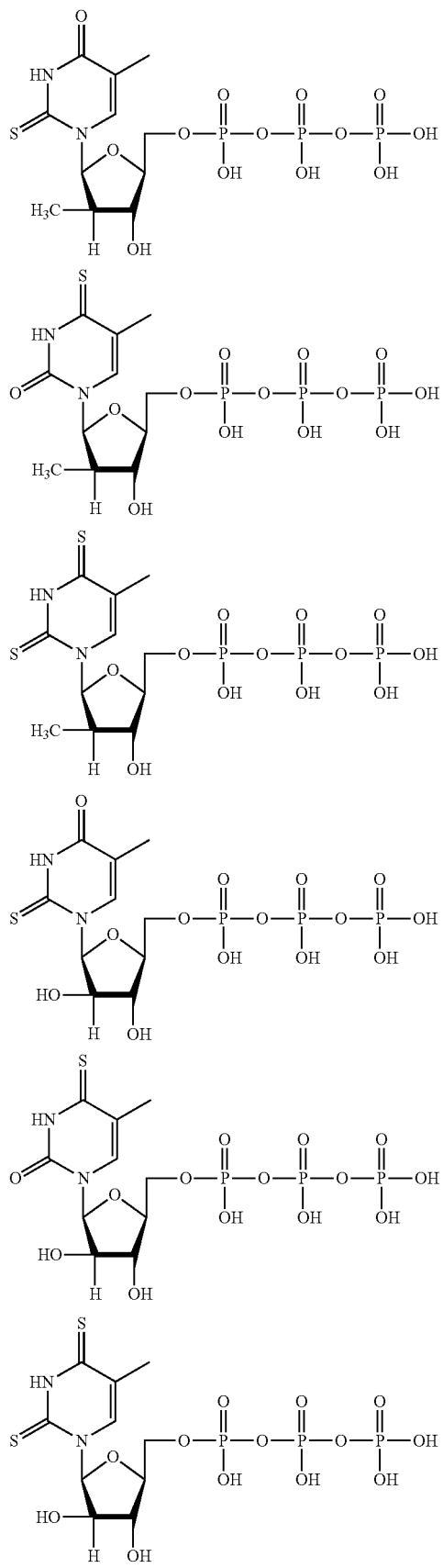
In exemplary embodiments, the compound is selected from:
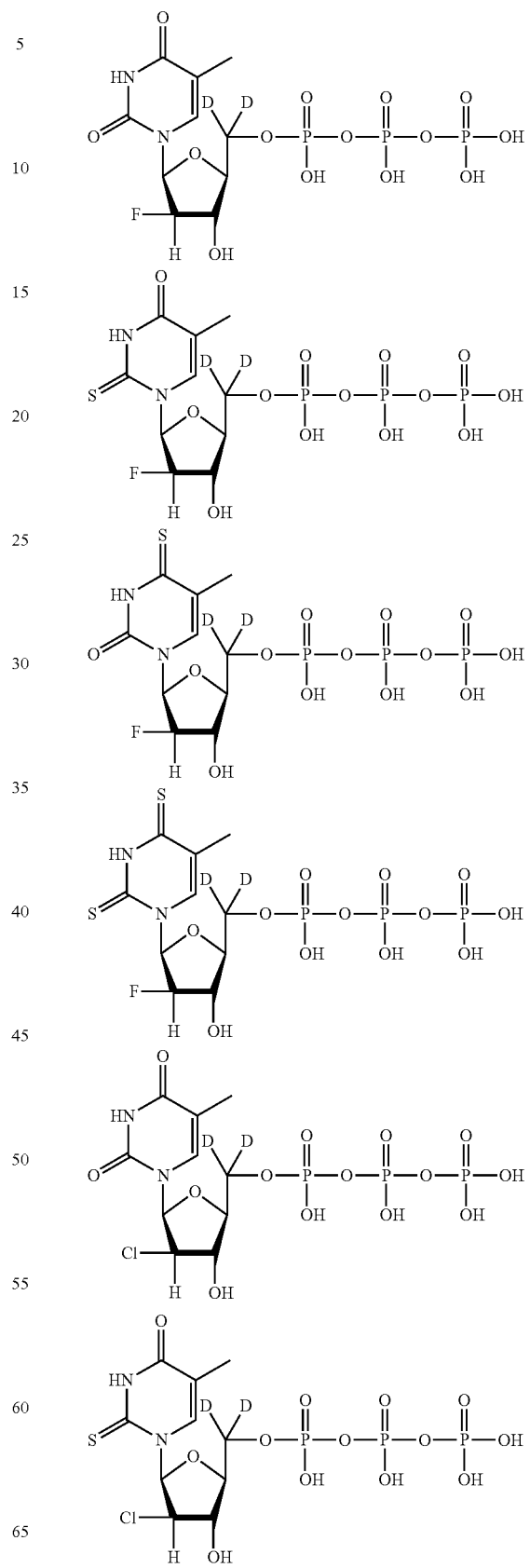

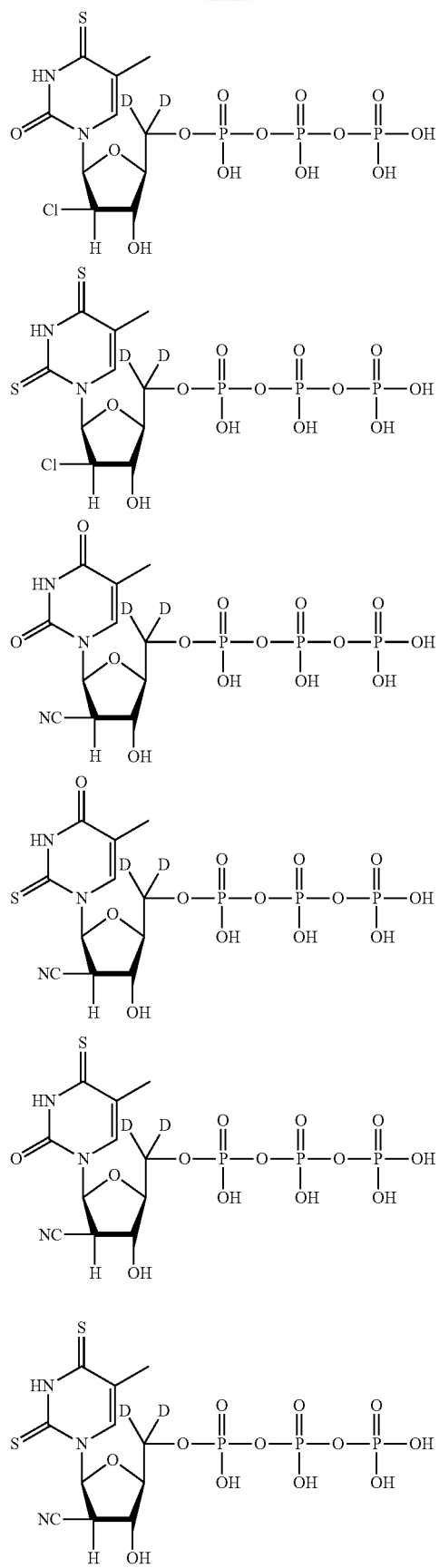
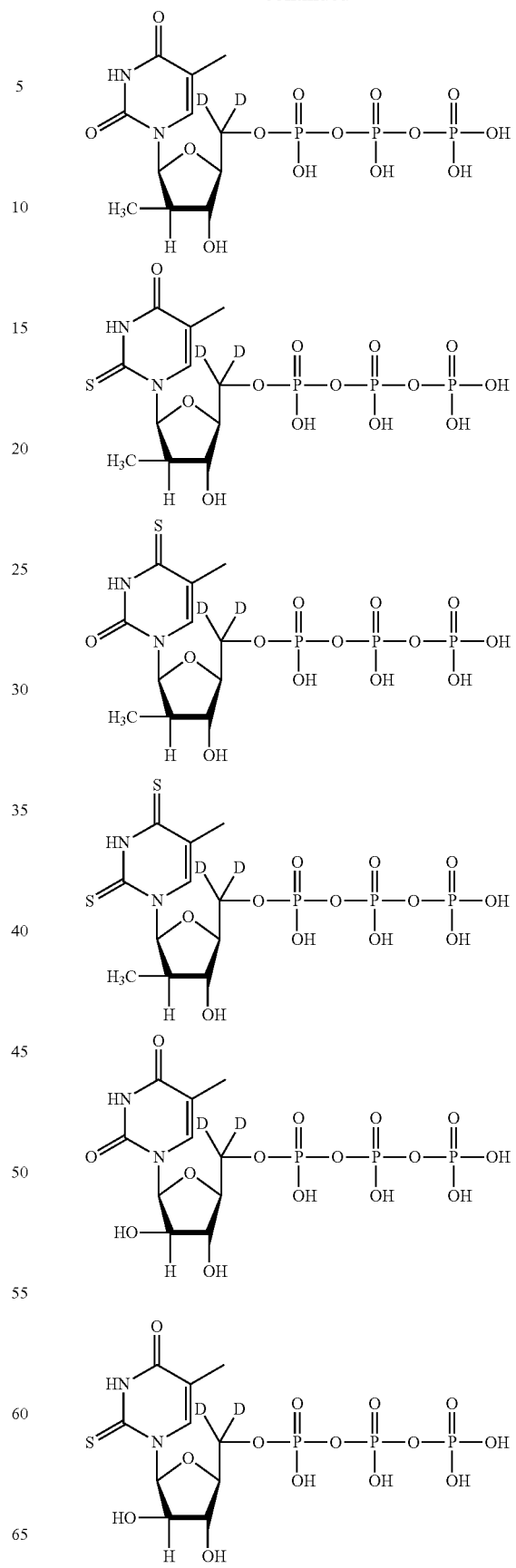

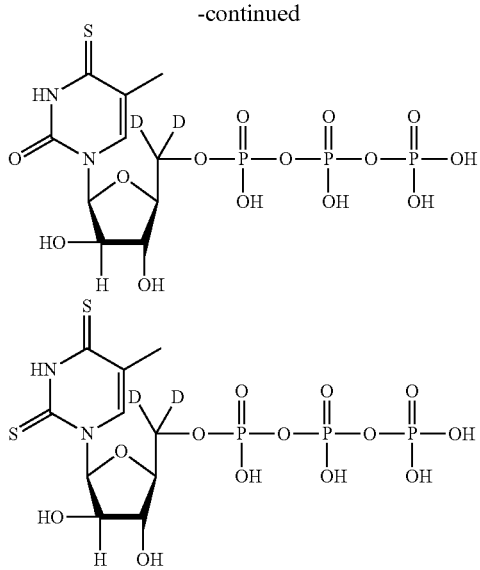

Methods of Use

The compounds provided herein can be used to treat viral infectious diseases. Examples of viral infections include but are not limited to, infections caused by RNA viruses (including negative stranded RNA viruses, positive stranded RNA viruses, double stranded RNA viruses and retroviruses) or DNA viruses. All strains, types, and subtypes of RNA viruses and DNA viruses are contemplated herein.

Viruses are infectious agents that can typically replicate inside the living cells of organisms. Virus particles (virions) usually consist of nucleic acids, a protein coat, and in some cases an envelope of lipids that surrounds the protein coat. The shapes of viruses range from simple helical and icosahedral forms to more complex structures. Virally coded protein subunits will self-assemble to form a capsid, generally requiring the presence of the virus genome. Complex viruses can code for proteins that assist in the construction of their capsid. Proteins associated with nucleic acid are known as nucleoproteins, and the association of viral capsid proteins with viral nucleic acid is called a nucleocapsid.

Viruses are transmitted by a variety of methods including direct or bodily fluid contact, e.g., blood, tears, semen, preseminal fluid, saliva, milk, vaginal secretions, lesions; droplet contact, fecal-oral contact, or as a result of an animal bite or birth. A virus has either DNA or RNA genes and is called a DNA virus or a RNA virus respectively. A viral genome is either single-stranded or double-stranded. Some viruses contain a genome that is partially double-stranded and partially single-stranded. For viruses with RNA or single-stranded DNA, the strands are said to be either positive-sense (called the plus-strand) or negative-sense (called the minus-strand), depending on whether it is complementary to the viral messenger RNA (mRNA). Positive-sense viral RNA is identical to viral mRNA and thus can be immediately translated by the host cell. Negative-sense viral RNA is complementary to mRNA and thus must be converted to positive-sense RNA by an RNA polymerase before translation. DNA nomenclature is similar to RNA nomenclature, in that the coding strand for the viral mRNA is complementary to it (negative), and the non-coding strand is a copy of it (positive).

Antigenic shift, or reassortment, can result in novel strains. Viruses undergo genetic change by several mechanisms. These include a process called genetic drift where individual bases in the DNA or RNA mutate to other bases. Antigenic shift occurs when there is a major change in the genome of the virus. This can be a result of recombination or reassortment. RNA viruses often exist as quasispecies or swarms of viruses of the same species but with slightly different genome nucleoside sequences.

The genetic material within viruses, and the method by which the material is replicated, vary between different types of viruses. The genome replication of most DNA viruses takes place in the nucleus of the cell. If the cell has the appropriate receptor on its surface, these viruses enter the cell by fusion with the cell membrane or by endocytosis. Most DNA viruses are entirely dependent on the host DNA and RNA synthesizing machinery, and RNA processing machinery. Replication usually takes place in the cytoplasm. RNA viruses typically use their own RNA replicase enzymes to create copies of their genomes.

The Baltimore classification of viruses is based on the mechanism of mRNA production. Viruses must generate mRNAs from their genomes to produce proteins and replicate themselves, but different mechanisms are used to achieve this. Viral genomes may be single-stranded (ss) or double-stranded (ds), RNA or DNA, and may or may not use reverse transcriptase (RT). Additionally, ssRNA viruses may be either sense (plus) or antisense (minus). This classification places viruses into seven groups: I, dsDNA viruses (e.g. adenoviruses, herpesviruses, poxviruses); II, ssDNA viruses (plus)sense DNA (e.g. parvoviruses); III, dsRNA viruses (e.g. reoviruses); IV, (plus)ssRNA viruses (plus)sense RNA (e.g. picornaviruses, togaviruses); V, (minus)ssRNA viruses (minus)sense RNA (e.g. orthomyxoviruses, Rhabdoviruses); VI, ssRNA-RT viruses (plus)sense RNA with DNA intermediate in life-cycle (e.g. retroviruses); and VII, dsDNA-RT viruses (e.g. hepadnaviruses).

Hepatitis B virus is a hepadnavirus. The virus particle, (virion) consists of an outer lipid envelope and an icosahedral nucleocapsid core composed of protein. The genome of HBV is made of circular DNA, but the DNA is not fully double-stranded. One end of the strand is linked to the viral DNA polymerase. The virus replicates through an RNA intermediate form by reverse transcription. Replication typically takes place in the liver where it causes inflammation (hepatitis). The virus spreads to the blood where virus-specific proteins and their corresponding antibodies are found in infected people. Blood tests for these proteins and antibodies are used to diagnose the infection.

Hepatitis B virus gains entry into the cell by endocytosis. Because the virus multiplies via RNA made by a host enzyme, the viral genomic DNA has to be transferred to the cell nucleus by host chaperones. The partially double stranded viral DNA is then made fully double stranded and transformed into covalently closed circular DNA (cccDNA) that serves as a template for transcription of viral mRNAs. The virus is divided into four major serotypes (adr, adw, ayr, ayw) based on antigenic epitopes presented on its envelope proteins, and into eight genotypes (A-H) according to overall nucleotide sequence variation of the genome.

The hepatitis B surface antigen (HBsAg) is typically used to screen for the presence of this infection. It is the first detectable viral antigen to appear during infection. However, early in an infection, this antigen may not be present and it may be undetectable later in the infection if it is being cleared by the host. The infectious virion contains an inner "core particle" enclosing viral genome. The icosahedral core particle is made of core protein, alternatively known as hepatitis B core antigen, or HBcAg. IgM antibodies to the hepatitis B core antigen (anti-HBc IgM) may be used as a serological marker. Hepatitis B e antigen (HBeAg) may appear. The presence of HBeAg in the serum of the host is associated with high rates of viral replication. Certain variants of the hepatitis B virus do not produce the 'e' antigen, If the host is able to clear the infection, typically the HBsAg will become undetectable and will be followed by IgG antibodies to the hepatitis B surface antigen and core antigen, (anti-HBs and anti HBc IgG). The time between the removal of the HBsAg and the appearance of anti-HBs is called the window period. A person negative for HBsAg but positive for anti-HBs has either cleared an infection or has been vaccinated previously. Individuals who remain HBsAg positive for at least six months are considered to be hepatitis B carriers. Carriers of the virus may have chronic hepatitis B, which would be reflected by elevated serum alanine aminotransferase levels and inflammation of the liver that may be identified by biopsy. Nucleic acid (PCR) tests have been developed to detect and measure the amount of HBV DNA in clinical specimens.

Acute infection with hepatitis B virus is associated with acute viral hepatitis. Acute viral hepatitis typically begins with symptoms of general ill health, loss of appetite, nausea, vomiting, body aches, mild fever, dark urine, and then progresses to development of jaundice. Chronic infection with hepatitis B virus may be either asymptomatic or may be associated with a chronic inflammation of the liver (chronic hepatitis), possibly leading to cirrhosis. Having chronic hepatitis B infection increases the incidence of hepatocellular carcinoma (liver cancer).

During HBV infection, the host immune response causes both hepatocellular damage and viral clearance. The adaptive immune response, particularly virus-specific cytotoxic T lymphocytes (CTLs), contributes to most of the liver injury associated with HBV infection. By killing infected cells and by producing antiviral cytokines capable of purging HBV from viable hepatocytes, CTLs eliminate the virus. Although liver damage is initiated and mediated by the CTLs, antigen-nonspecific inflammatory cells can worsen CTL-induced immunopathology, and platelets activated at the site of infection may facilitate the accumulation of CTLs in the liver.

Therapeutic agents can stop the virus from replicating, thus minimizing liver damage. In certain embodiments, the disclosure relates to methods of treating a subject diagnosed with HBV by administering a compound disclosed herein disclosed herein. In certain embodiments, the subject is immunocompromised. In certain embodiments, the compound is administered in combination with another antiviral agent such as lamivudine, adefovir, tenofovir, telbivudine, and entecavir, and/or immune system modulators interferon alpha-2a and pegylated interferon alpha-2a (Pegasys). In certain embodiments, the disclosure relates to preventing an HBV infection in an immunocompromised subject at risk of infection by administering a pharmaceutical composition disclosed herein and optionally one or more antiviral agents. In certain embodiments, the subject is at risk of an infection because the sexual partner of the subject is diagnosed with HBV.

Compounds of the present invention can be administered in combination with a second antiviral agent such as abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, sofosbovir, stavudine, telaprevir, telbivudine, tenofovir, tenofovir disoproxil, tipranavir, trifluridine, trizivir, tromantadine, truvada, valaciclovir, valganciclovir, vicriviroc, vidarabine, viramidine zalcitabine, zanamivir, or zidovudine and combinations thereof.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier that releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as a prodrug are known, for example, in Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It has been shown that ester prodrugs are readily degraded in the body to release the corresponding alcohol. See e.g., Imai, Drug Metab Pharmacokinet. (2006) 21(3):173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, cornstarch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaluronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na-CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present invention.

It is appreciated that nucleosides of the present invention have several chiral centers and may exist in and be isolated in optically active and racemic forms. Some compounds may exhibit polymorphism. It is to be understood that the present invention encompasses any racemic, optically active, diastereomeric, polymorphic, or stereoisomeric form, or mixtures thereof, of a compound of the invention, which possess the useful properties described herein. It is well known in the art how to prepare optically active forms (for example, by resolution of the racemic form by recrystallization techniques, by synthesis from optically-active starting materials, by chiral synthesis, or by chromatographic separation using a chiral stationary phase).

Carbons of the nucleoside are chiral, their nonhydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring β-D nucleosides), cis (with both groups "down", which is a nonnaturally occurring β-L configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the nonnaturally occurring configuration.

Likewise, most amino acids are chiral (designated as L or D, wherein the L enantiomer is the naturally occurring configuration) and can exist as separate enantiomers.

Examples of methods to obtain optically active materials are known in the art, and include at least the following. i) physical separation of crystals—a technique whereby macroscopic crystals of the individual enantiomers are manually separated. This technique can be used if crystals of the separate enantiomers exist, i.e., the material is a conglomerate, and the crystals are visually distinct; ii) simultaneous crystallization—a technique whereby the individual enantiomers are separately crystallized from a solution of the racemate, possible only if the latter is a conglomerate in the solid state; iii) enzymatic resolutions—a technique whereby partial or complete separation of a racemate by virtue of differing rates of reaction for the enantiomers with an enzyme; iv) enzymatic asymmetric synthesis—a synthetic technique whereby at least one step of the synthesis uses an enzymatic reaction to obtain an enantiomerically pure or enriched synthetic precursor of the desired enantiomer; v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries; vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer; vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer; viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions; ix) enantiospecific synthesis from non-racemic precursors—a synthetic technique whereby the desired enantiomer is obtained from non-chiral starting materials and where the stereochemical integrity is not or is only minimally compromised over the course of the synthesis; x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions; xi) chiral gas chromatography—a technique whereby the racemate is volatilized and enantiomers are separated by virtue of their differing interactions in the gaseous mobile phase with a column containing a fixed non-racemic chiral adsorbent phase; xii) extraction with chiral solvents—a technique whereby the enantiomers are separated by virtue of preferential dissolution of one enantiomer into a particular chiral solvent; xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through. Chiral chromatography, including simulated moving bed chromatography, is used in one embodiment. A wide variety of chiral stationary phases are commercially available.

Some of the compounds described herein contain olefinic double bonds and unless otherwise specified, are meant to include both E and Z geometric isomers.

In addition, some of the nucleosides described herein, may exist as tautomers, such as, keto-enol tautomers. The individual tautomers as well as mixtures thereof are intended to be encompassed within the compounds of the present invention.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: HBV Assay

HepG2.2.15 cells (100 µL) in RPMI1640 medium with 10% fetal bovine serum was added to all wells of a 96-well plate at a density of $1\times10^4$ cells per well and the plate was incubated at 37° C. in an environment of 5% $CO_2$ for 24 hours. Following incubation, six ten-fold serial dilutions of test compound prepared in RPMI1640 medium with 10% fetal bovine serum were added to individual wells of the plate in triplicate. Six wells in the plate received medium alone as a virus only control. The plate was incubated for 6 days at 37° C. in an environment of 5% $CO_2$. The culture medium was changed on day 3 with medium containing the indicated concentration of each compound. One hundred microliters of supernatant was collected from each well for analysis of viral DNA by qPCR and cytotoxicity was evaluated by XTT staining of the cell culture monolayer on the sixth day.

Ten microliters of cell culture supernatant collected on the sixth day was diluted in qPCR dilution buffer (40 µg/mL sheared salmon sperm DNA) and boiled for 15 minutes. Quantitative real time PCR was performed in 386 well plates using an Applied Biosystems 7900HT Sequence Detection System and the supporting SDS 2.4 software. Five microliters (5 µL) of boiled DNA for each sample and serial 10-fold dilutions of a quantitative DNA standard were subjected to real time Q-PCR using Platinum Quantitative PCR SuperMix-UDG (Invitrogen) and specific DNA oligonucleotide primers (IDT, Coralville, ID) HBV-AD38-qF1 (5'-CCG TCT GTG CCT TCT CAT CTG-3') (SEQ ID NO:1), HBV-AD38-qR1 (5'-AGT CCA AGA GTY CTC TTA TRY AAG ACC TT-3') (SEQ ID NO:2), and HBV-AD38-qP1 (5'-FAM CCG TGT GCA/ZEN/ CTTCGCTTCACCTCTGC-3'BHQ1) (SEQ ID NO:3, underlined portion only) at a final concentration of 0.2 µM for each primer in a total reaction volume of 15 µL. The HBV DNA copy number in each sample was interpolated from the standard curve by the SDS.24 software and the data were imported into an Excel spreadsheet for analysis.

The 50% cytotoxic concentration for the test materials are derived by measuring the reduction of the tetrazolium dye XTT in the treated tissue culture plates. XTT is metabolized by the mitochondrial enzyme NADPH oxidase to a soluble formazan product in metabolically active cells. XTT solution was prepared daily as a stock of 1 mg/mL in PBS. Phenazine methosulfate (PMS) stock solution was prepared at 0.15 mg/mL in PBS and stored in the dark at −20° C. XTT/PMS solution was prepared immediately before use by adding 40 µL of PMS per 1 mL of XTT solution. Fifty microliters of XTT/PMS was added to each well of the plate and the plate incubated for 2-4 hours at 37° C. The 2-4 hour incubation has been empirically determined to be within linear response range for XTT dye reduction with the indicated numbers of cells for each assay. Adhesive plate sealers were used in place of the lids, the sealed plate was inverted several times to mix the soluble formazan product and the plate was read at 450 nm (650 nm reference wavelength) with a Molecular Devices SpectraMax Plus 384 spectrophotometer. Data were collected by Softmax 4.6 software and imported into an Excel spreadsheet for analysis. The data is summarized in Table 1.

TABLE 1
| Structure and I.D. | | HBV Efficacy Assay | | Cytotoxicity (CC$_{50}$ μM) | | |
|---|---|---|---|---|---|---|
| | | EC50 (uM) | HepG2 CC$_{50}$ (μM) | Huh-7 | HepG2 | BxPC3 |
| 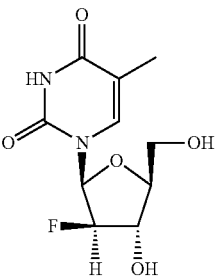 Clevudine | EIDD-02020 | 0.46 | >100 | >400 | >400 | >400 |
| 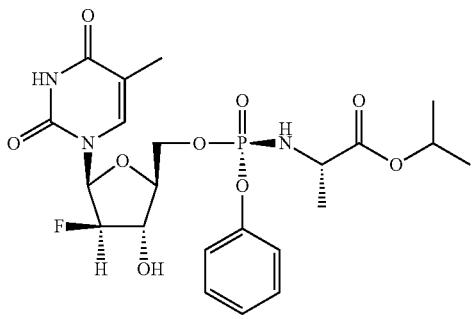 [SMILES: Cc1cn([C@H]2O[C@@H](CO[P@@](=O)(N[C@@H](C)C(=O)OC(C)C)Oc3ccccc3)[C@H](O)[C@H]2F)c(=O)[nH]c1=O] | EIDD-02173 | 1.71 | >100 | >400 | >400 | >400 |
| 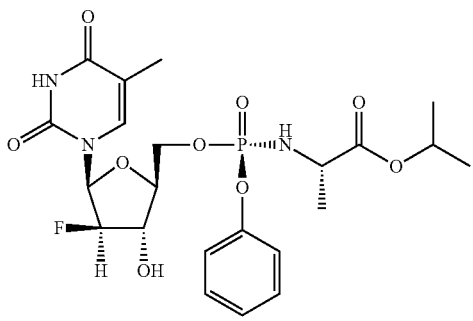 [SMILES: Cc1cn([C@H]2O[C@@H](CO[P@](=O)(N[C@@H](C)C(=O)OC(C)C)Oc3ccccc3)[C@H](O)[C@H]2F)c(=O)[nH]c1=O] | EIDD-02174 | 4.29 | >100 | 290 | >400 | >400 |
| 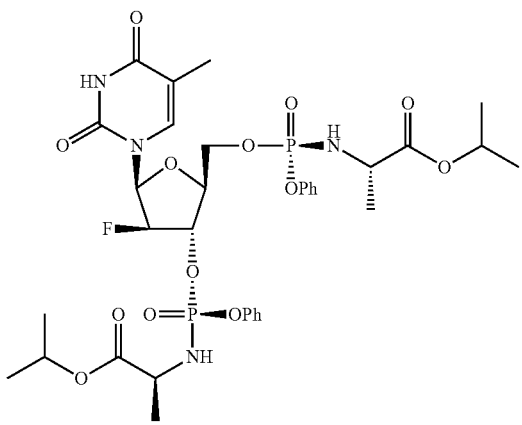 | EIDD-02308 | 2.9 | >100 | | | |

TABLE 1-continued

| Structure | Compound | | | | | |
|---|---|---|---|---|---|---|
| (thymidine 3',5'-bis[phenyl(isopropoxy-L-alaninyl)] phosphate with 3'-fluoro) | EIDD-02309 | 2.39 | 85.1 | | | |
| (2-thio-thymidine, 3'-fluoro) | EIDD-02333-1 | >100 | >100 | | | |
| (2-thio-thymidine 5'-[phenyl(isopropoxy-L-alaninyl)] phosphate, 3'-fluoro) | EIDD-02334-1 | >100 | >100 | | | |
| (2-thio-thymidine 5'-[phenyl(isopropoxy-L-alaninyl)] phosphate, 3'-fluoro) | EIDD-02335-1 | >100 | >100 | | | |
| (Lamivudine) | 3TC | 0.14 | >10 | >400 | >400 | >400 |

TABLE 1-continued

| Structure and I.D. | | Cytotoxicity (CC$_{50}$ μM) | | | | | |
|---|---|---|---|---|---|---|---|
| | | CEM | A204 | IEC-6 | H9c | A549 | Vero |
| Clevudine | EEID-02020 | >400 | >400 | >400 | >400 | >400 | >400 |
| [structure] | EIDD-02173 | 140 | 330 | 307 | 344 | >400 | >400 |
| [structure] | EIDD-02174 | >400 | 374 | 338 | 311 | >400 | >400 |
| [structure] | EIDD-02308 | | | | | | |

TABLE 1-continued
| | |
|---|---|
| 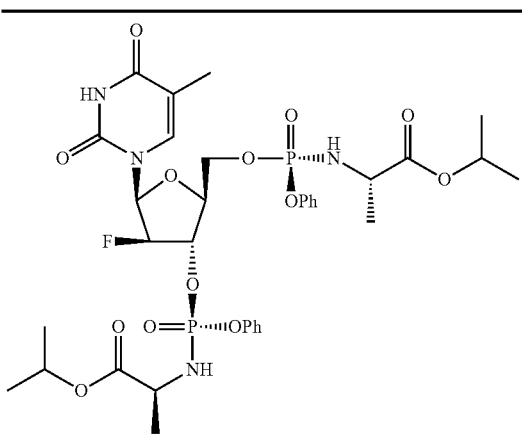 | EIDD-02309 |
| 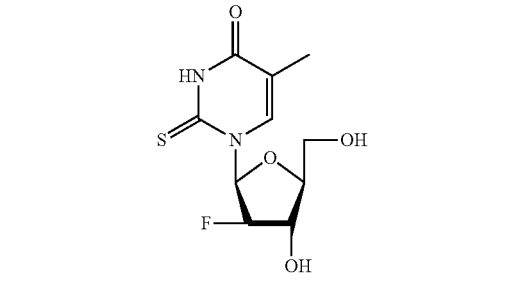 | EIDD-02333-1 |
| 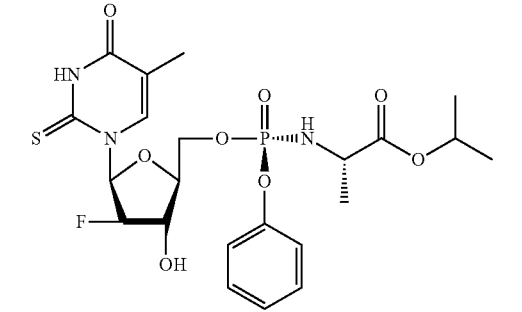 | EIDD-02334-1 |
| 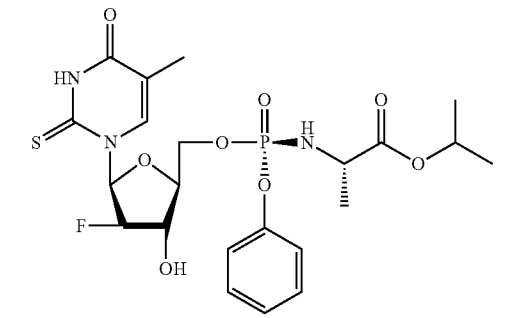 | EIDD-02335-1 |
| 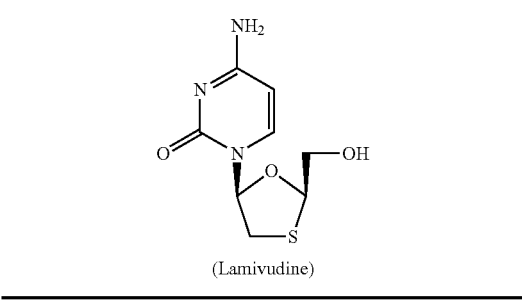<br>(Lamivudine) | 3TC |

Example 2: Preparation of (S)-2-[—(S)-2-(2,3,4,5,6-pentafluoro-phenoxy)-phenoxy-phosphorylamino] propionic acid isopropyl ester

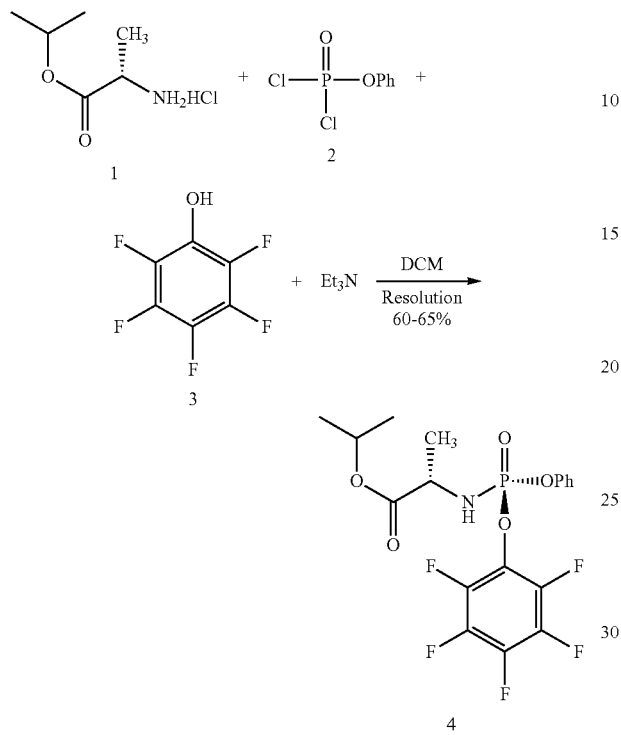

A flask containing (S)-isopropyl 2-aminopropanoate hydrochloride (72.0 g, 430 mmol) was charged with phenyl phosphorodichloridate (64.2 mL, 430 mmol) and dichloromethane (DCM, 1200 mL). The mixture was cooled to −70 to −78° C. with dry-ice acetone bath and then treated with drop wise addition of triethylamine (120 mL, 859 mmol) over a period of 30 minutes. The mixture was stirred at −70 to −78° C. for 30 more minutes and then was allowed to warm to ambient temperature and stirred for 1 h.

The reaction mixture was then cooled to 0-5° C. in ice-bath and added to a solution of 2,3,4,5,6-pentafluorophenol (79 g, 430 mmol) and triethylamine (59.9 mL, 430 mmol) in 100 mL DCM over a period of 30 minutes. The resulting mixture was stirred at −70 to −78° C. for 30 more minutes, then was warmed to ambient temperature and stirred for 2 h.

The solids were filtered off and solid cake was washed with 200 mL ethyl acetate. The filtrate and washes were concentrated by vacuum distillation until a semi-solid residue remained. The semi-solid residue was dissolved in 500 mL ethyl acetate and washed with water and brine. The washes were re-extracted with 50 mL of ethyl acetate. The combined organic layer was dried over anhydrous MgSO$_4$ and concentrated to give crude racemic product 210 g (100% yield). Based on the NMR characterization, the racemic product appears to be a 1:1 mixture of two diastereomers.

Kinetic resolution of the racemic product to produce the desired SS diastereomer was accomplished by the following protocol.

1) The crude racemic mixture was slurried in 500 mL of 20% ethyl acetate/hexanes and was added to a solution of 5 g of pentafluorophenol, 10 mL of triethylamine, and 100 mg of dimethylaminopyridine in 20 mL of 20% ethyl acetate/hexanes. The reaction mixture was warmed to 45-50° C. for 30 minutes, and the slurry was allowed to stir overnight. The white solid was collected by filtration and was washed with 200 mL of 20% ethyl acetate/hexanes and 100 mL of hexanes. The product was dried at 40° C. under vacuum to give a white solid (weight: 98 g). Based on the NMR characterization, the product appears to be substantially the SS diastereomer.

2) The filtrate and washings from the above reaction were combined and concentrated to give a semi solid which was mainly the SS diastereomer as shown by NMR along with other impurities. This residue was dissolved in 150 mL ethyl acetate and washed with 50 mL of 1N HCl, water and 5% K$_2$CO$_3$ solution. The organic layer was dried and concentrated. The white residue was slurred in 100 mL of 20% ethyl acetate/hexanes, and the solid was collected by filtration. The cake was then washed with 20% ethyl acetate/hexanes, hexanes and dried. The weight of the resulting white solid was 22 g. Based on the $^1$H- and $^{31}$P-NMR characterization, the product appears to be substantially the SS diastereomer. Total weight of the product after resolution: 120 g (61.6% yield).

Example 3: Synthesis of 2-chloro-4-nitrophenyl phosphoramidate (5)

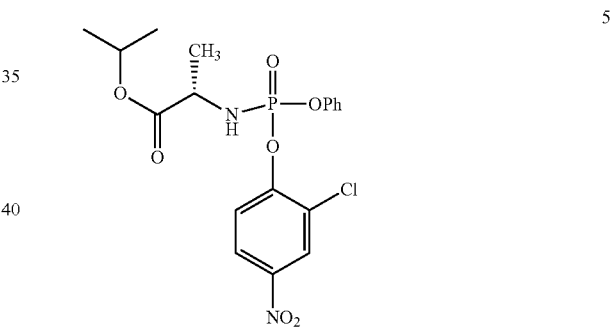

A solution of phenyl dichlorophosphate (60 g, 42.5 mL, 284 mmol) in dichloromethane (300 mL) was cooled to 0° C. and then treated with (S)-isopropyl 2-aminopropanoate hydrochloride (47.7 g, 284 mmol). The mixture was further cooled to −78° C. and treated dropwise with a solution of triethylamine (57.6 g, 79 mL, 569 mmol) in methylene chloride (300 mL) over a 1 h period. The reaction mixture was warmed to 0° C. for 30 min and then treated with a preformed mixture of 2-chloro-4-nitrophenol (46.9 g, 270 mmol) and triethylamine (28.8 g, 39.6 mL, 284 mmol) in dichloromethane (120 mL) over a 20 min period. After 2 h at 0° C., the mixture was filtered through a fritted funnel, and the collected filtrate concentrated to dryness. The crude gum was dissolved MTBE (500 mL) and washed with 0.2 M K$_2$CO$_3$ (2×100 mL) followed by 10% brine (3×75 mL). The organic phase was dried over sodium sulfate, filtered and concentrated to dryness by rotary evaporator to give a diastereomeric mixture (100 g, 93%) as a pale yellow oil.

Example 4: Separation of Compound 5 Diastereomers

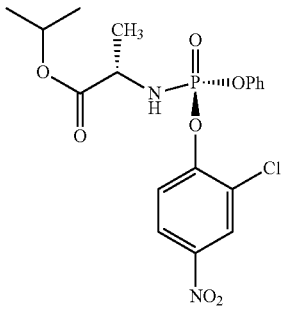

5

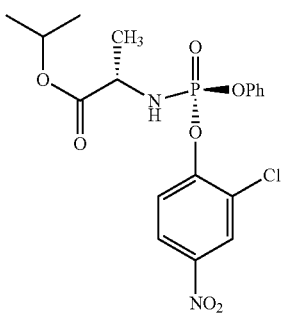

7

The diastereomeric mixture 5 (28 g, 63.2 mmol) was dissolved in 2:3 ethyl acetate:hexanes (100 mL) and cooled to −20° C. After 16 h, the resulting white solid was collected by filtration and dried under high vacuum to give a 16:1 $S_p$:$R_p$-diastereomeric mixture (5.5 g, 19.6%). The mother liquor was concentrated and the resulting residue dissolved in 2:3 ethyl acetate:hexanes (50 mL). After 16 h at −10° C., the resulting white solid was collected and dried under high vacuum to give a 1:6 $S_p$:$R_p$-diastereomeric mixture (4 g, 14%). The 16:1 $S_p$:$R_p$-diastereomeric mixture (5.5 g, 12.4 mmol) was suspended in hot hexanes (50 mL) and treated slowly with ethyl acetate (approximately 10 mL) until complete dissolution. After cooling to 0° C., the resulting white solid was collected by filtration, washed with hexanes, and dried under high vacuum to give the $S_p$-diastereomer of 6 (4.2 g, 76%) as a single isomer.

The 1:6 $S_p$:$R_p$-diastereomeric mixture (4 g, 12.4 mmol) was suspended in hot hexanes (50 mL) and treated slowly with ethyl acetate (approximately 5 mL) until complete dissolution. After cooling to 0° C., the resulting white solid was collected by filtration, washed with hexanes, and dried under high vacuum to give the $R_p$ diastereomer of 7 (3.2 g, 80%) as a single isomer.

Example 5: Synthesis of Compound 8

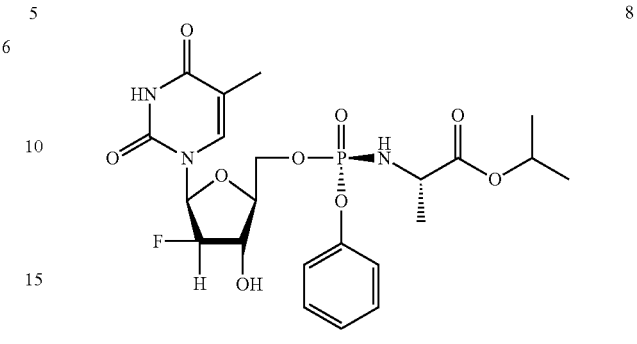

8

To a dry 100 mL flask was added 1-((2S,3S,4S,5S)-3-fluoro-4-hydroxy-5-(hydroxymethyl)tetrahydrofuran-2-yl)-5-methylpyrimidine-2,4(1H,3H)-dione (300 mg, 1.153 mmol) and THF (15 mL). The suspension was cooled in an ice bath under nitrogen. tert-butylmagnesium chloride (2.260 mL, 2.260 mmol) was added via syringe forming a clear solution. The mixture was stirred at ambient temperature for 30 minutes and cooled to 0° C. again. A solution of compound 4 in THF (20 mL) was added via syringe over 10 min. period at 0° C. The resulting yellowish color solution was stirred at room temperature overnight.

The reaction was cooled to 0° C. and quenched with 5 mL of 2N HCl. The reaction was then allowed to warm to room temperature and stir for 30 minutes. Next, 30 mL of toluene was added, and the resulting layers were separated. The organic layer was washed with 1N HCl (1×20 mL), water (20 mL), 5% aq. $K_2CO_3$ soln. (2×30 mL) and brine (30 mL). All of the aqueous layers were re-extracted with toluene (30 mL) and washed with 5% $K_2CO_3$ (1×30 mL) and brine (30 mL). The combined organic layers were dried over anhydrous $MgSO_4$ and concentrated to give oily residue. The product was purified on 15 grams of silica gel eluting with 1% and then with 2.5% MeOH/DCM. Product is obtained in 2.5% MeOH/DCM as single spot product.

Example 6: Preparation of Compound 9

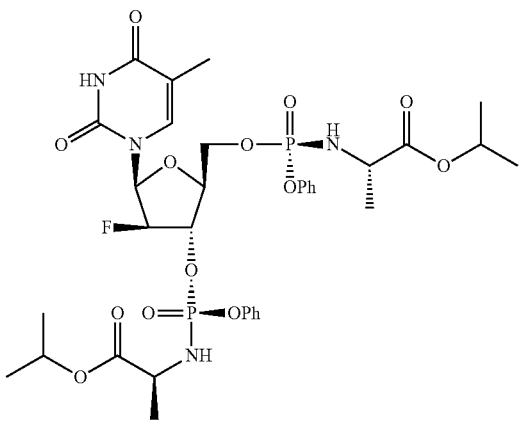

9

Compound was isolated from the reaction mixture of the synthesis of compound 8.

Example 7: Synthesis of Compound 10

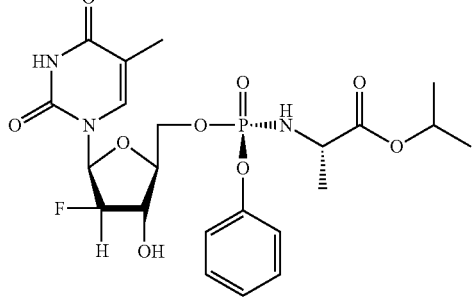

10

To a dry 100 mL flask was added 1-((2S,3S,4S,5S)-3-fluoro-4-hydroxy-5-(hydroxymethyl)tetrahydrofuran-2-yl)-5-methylpyrimidine-2,4(1H,3H)-dione (400 mg, 1.537 mmol) and THF (20 mL). The suspension was cooled in an ice bath under nitrogen. tert-butylmagnesium chloride (1.691 mL, 1.691 mmol) was added drop wise over a period of 10 minutes. The resulting mixture was stirred at 0° C. for 30 minutes and then was allowed to warm to room temperature and stir for 30 minutes. A solution of (2S)-isopropyl 2-(((2-chloro-4-nitrophenoxy)(phenoxy)phosphoryl)amino) propanoate (817 mg, 1.845 mmol) in THF (150 mL) was added at room temperature drop wise over a period of 10-50 minutes. The resulting solution was allowed to stir at ambient temperature overnight.

The reaction was cooled to 0° C. and quenched with 5 mL of 2N HCl. The reaction mixture was then allowed to warm to room temperature and stir for 30 min. Next, 30 mL of toluene was added, and the layers were separated. The organic layer was washed with 1N HCl (1×20 mL), water (20 mL), 5% aq. K$_2$CO$_3$ soln. (2×30 mL) and brine (30 mL). All of the aqueous layers were re-extracted with toluene (30 mL) and washed with 5% K$_2$CO$_3$ (1×30 mL) and brine (30 mL). The combined organic layers were dried over anhydrous MgSO$_4$ and concentrated to give oily residue.

The product was purified on 15 grams of silica gel eluting with 1% and then with 2.5% MeOH/DCM. Product is obtained in 2.5% MeOH/DCM.

Example 8: Preparation of Compound 11

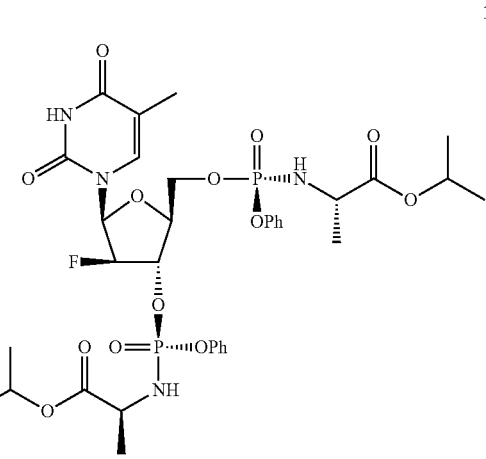

11

Compound was isolated from the reaction mixture of the synthesis of compound 10.

Example 9: Synthesis of Compound 13

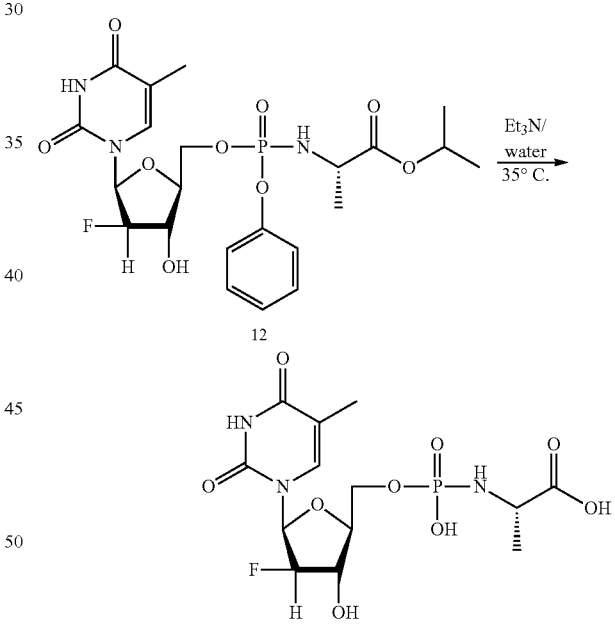

A sealable pressure tube was charged with a stir bar, 12 (0.132 g, 0.25 mmol), triethylamine (12.5 mL), and water (12.5 mL). The tube was sealed and heated at 35° C. overnight with stirring. After 16 h, the reaction vessel was cooled to rt and opened, and the contents were transferred to a round bottom flask. The mixture was concentrated by rotary evaporation to give ~200 mg crude, which was partitioned between water and dichloromethane (30 mL each). The organic layer was discarded, and the aqueous layer was concentrated by rotary evaporation to give ~150 mg crude, which was taken up in MeOH and immobilized on Celite. Automated flash chromatography on a Combiflash (12 g column, iPrOH to 7:2:1 iPrOH:conc. NH$_4$OH:water gradient) gave the product as a wet ammonium salt. The solid was dissolved in water, frozen in a dry ice bath, and lyophilized to give 13 (0.089 g, 81%) as a flocculent white solid, which was determined to be ~94% pure by $^1$H NMR analysis: $^1$H NMR (400 MHz, MeOH-d$_4$) δ 7.66 (t, J=1.4 Hz, 1H), 6.18 (dd, J=15.4 Hz, 4.3 Hz, 1H), 5.00 (ddd, J=52.6 Hz, 4.2 Hz, 3.3 Hz, 1H), 4.42 (ddd, J=19.8 Hz, 4.7 Hz, 3.4 Hz, 1H), 4.05-3.95 (m, 3H), 3.76 (dq, J=8.9 Hz, 7.0 Hz, 1H), 1.92 (d, J=1.2 Hz, 3H), 1.35 (d, J=7.0 Hz, 1H); $^1$H NMR (400 MHz, D$_2$O) δ 7.65 (t, J=1.3 Hz, 1H), 6.25 (dd, J=15.2 Hz, 4.4 Hz, 1H), 5.16 (ddd, J=51.9 Hz, 4.3 Hz, 3.5 Hz, 1H), 4.48 (ddd, J=19.9 Hz, 5.4 Hz, 3.5 Hz, 1H), 4.10-3.93 (m, 3H), 3.62 (dq, J=8.7 Hz, 7.0 Hz, 1H), 1.88 (d, J=1.2 Hz, 3H), 1.28 (d, J=7.1 Hz, 3H); $^1$H NMR (400 MHz, DMSO-d$_6$) δ 7.64 (t, J=1.4 Hz, 1H), 6.13 (dd, J=13.2 Hz, 4.9 Hz, 1H), 5.07 (dt, J=53.3 Hz, 4.6 Hz, 1H), 4.26 (dt, J=20.4 Hz, 4.7 Hz, 1H), 3.92-3.75 (m, 3H), 3.45-3.35 (m, 1H, overlaps with broad water peak), 1.80 (d, J=1.2 Hz, 3H), 1.14 (d, J=7.2 Hz, 3H); $^{13}$C NMR (100 MHz, DMSO-d$_6$) δ 177.1, 163.8, 150.3, 136.5, 109.0, 95.4 (d, J=190.4 Hz), 82.1 (d, J=16.6 Hz), 81.9 (t, J=7.1 Hz), 72.9 (d, J=23.3 Hz), 62.6, 50.8, 19.8 (d, J=6.5 Hz), 12.1; $^{31}$P NMR (162 MHz, DMSO-d$_6$) δ 6.04 (s); ESI-MS: m/z 412.0 ([M+H]$^+$).

Example 10: Synthesis of Compound 15

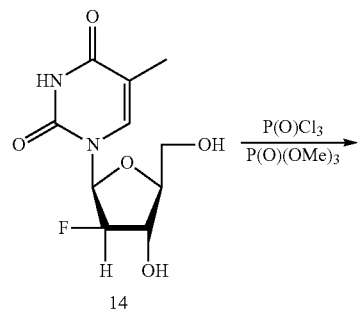

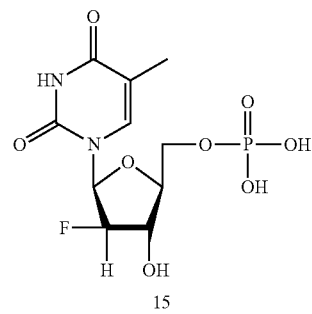

A round bottom flask was charged with Clevudine (14) (0.143 g, 0.55 mmol), and both were dried overnight at 50° C. in a vacuum oven. The flask was removed and cooled to rt under nitrogen, and the solid was dissolved in trimethyl phosphate (1.375 mL) with stirring. The solution was cooled to 0° C., and phosphoryl trichloride (0.126 g, 0.825 mmol) was added dropwise via syringe. The reaction mixture was stirred at 0° C. for 3 h, at which point analysis by TLC showed little reaction. A second aliquot of phosphoryl trichloride (0.422 g, 2.75 mmol) was added dropwise via syringe, and the mixture was stored at −5° C. in the freezer overnight. After 20 h at this temperature, the mixture was poured into water (20 mL), and the aqueous layer was washed with chloroform (2×20 mL). The aqueous layer was then neutralized by addition of concentrated aqueous ammonia to pH=7, again washed with chloroform (1×20 mL), and concentrated by rotary evaporation (bath temperature 25° C.). The resulting crude semisolid was suspended in MeOH and immobilized on Celite. Automated flash chromatography on a Combiflash (12 g column, iPrOH to 7:2:1 iPrOH:conc. NH$_4$OH:water gradient) gave ~200 mg of a wet, white solid. The solid was dissolved in water, frozen in a dry ice bath, and lyophilized to give 15 (0.055 g, 29%) as a flocculent white solid, which was determined to be ~95% pure by $^1$H NMR analysis: $^1$H NMR (400 MHz, D$_2$O) δ 7.69 (t, J=1.5 Hz, 1H), 6.28 (dd, J=15.6 Hz, 4.4 Hz, 1H), 5.18 (ddd, J=51.8 Hz, 4.4 Hz, 3.3 Hz, 1H), 4.51 (ddd, J=19.6 Hz, 5.2 Hz, 3.2 Hz, 1H), 4.16-4.01 (m, 3H), 1.89 (d, 1.2 Hz, 3H); $^1$H NMR (400 MHz, DMSO-d$_6$) δ 7.60 (s, 1H), 6.11 (dd, J=13.8 Hz, 4.6 Hz, 1H), 5.03 (dt, J=53.2 Hz, 4.4 Hz, 1H), 4.29 (dt, J=20.2 Hz, 3.6 Hz, 1H), 3.90 (br m, 3H), 1.79 (d, 1.2 Hz, 3H); $^{13}$C NMR (100 MHz, DMSO-d$_6$) δ 163.8, 150.3, 136.6, 109.0, 95.3 (d, J=190.0 Hz), 82.1 (d, J=16.5 Hz), 81.9 (t, J=6.4 Hz), 72.6 (d, J=23.5 Hz), 62.6, 12.2; $^{31}$P NMR (162 MHz, DMSO-d$_6$) δ 0.01 (s); ESI-MS: m/z 339.0 ([M+H]$^+$).

Example 11: General Procedure for Preparation of 5'-Triphosphates

Nucleoside analogue was dried under high vacuum at 50° C. for 18 h and then dissolved in anhydrous trimethylphosphate (0.3 M). After addition of PROTON-SPONGE™ (1.5 molar equiv), the mixture was cooled to 0° C. and treated dropwise with phosphoryl chloride (1.3 molar equiv) via microsyringe over a 15 min period. The mixture continued stirring at 0° C. for 4 to 6 h while being monitored by TLC (7:2:1 isopropanol:conc. NH$_4$OH:water). Once greater than 85% conversion to the monophosphate, the reaction mixture was treated with a mixture of bis(tri-n-butylammonium pyrophosphate) (3 molar equiv) and tributylamine (6 molar equiv) in anhydrous DMF (1 mL). After 20 min at 0° C. with monitoring by TLC (11:7:2 NH$_4$OH:isopropanol:water), the mixture was treated with 20 mL of a 100 mM solution of triethylammonium bicarbonate (TEAB), stirred for 1 h at rt and then extracted with ether (3×15 mL). The aqueous phase was then purified by anion-exchange chromatography over DEAE SEPHADEX™ A-25 resin (11×200 mm) using a buffer gradient from 50 mM (400 mL) to 600 mM (400 mL) TEAB. Fractions of 10 mL were analyzed by tlc (11:7:2 NH$_4$OH:isopropanol:water). Triphosphate (eluted @ 500 mM TEAB) containing fractions were combined and concentrated by rotary evaporator (bath <25° C.). The resulting solid was reconstituted in DI water (10 mL) and concentrated by lyophilization.

Example 12: Synthesis of Clevudine-5'-Triphosphate (16)

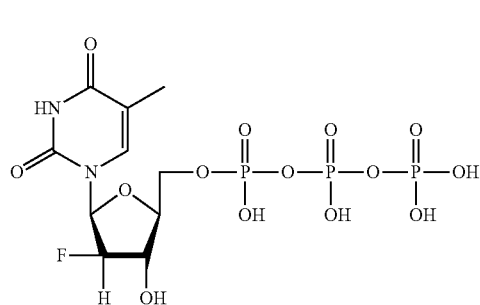

16

Compound 16 was synthesized using the general procedure for 5'-triphosphate synthesis.

Example 13: Synthesis of Compound 17

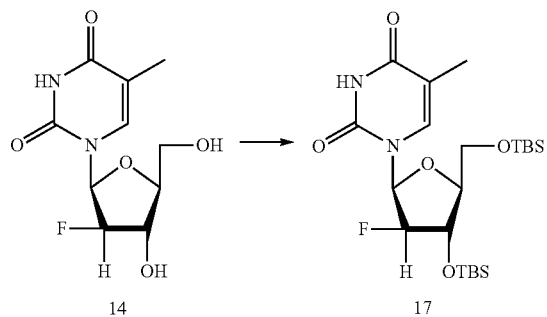

To a suspension of 14 (0.980 g, 3.77 mmol) in anhydrous CH$_2$Cl$_2$ (37.7 mL) was sequentially added imidazole (0.769 g, 11.30 mmol), DMAP (0.046 g, 0.377 mmol) and TBS Triflate (2.162 mL, 9.42 mmol) at 0° C. under argon. The resulting reaction was stirred at 0° C. for 1 hr. The reaction mixture was then warmed up to r.t. and stirred for 24 hrs. The reaction mixture was washed with H$_2$O, brine and dried over Na$_2$SO$_4$. After removal of the solvent, the obtained colorless residue was loaded on an ISCO column (40 g silica gel). Fractions containing product were collected and condensed on rotavap to give a colorless residue, which turned into a white foam under high vacuum to provide 17 (1.8303 g, 99% yield).

Example 14: Synthesis of Compound 18

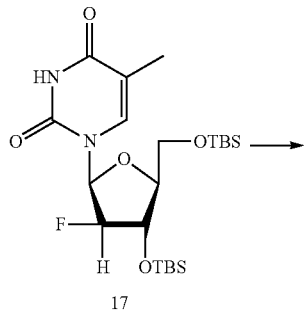

17

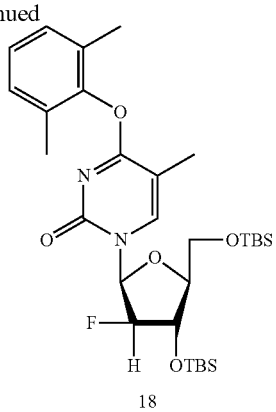

18

To a colorless solution of 17 (1.830 g, 3.74 mmol) in CH$_2$Cl$_2$ (30.0 mL) was sequentially added DMAP (0.915 g, 7.49 mmol) and triethylamine (1.096 mL, 7.86 mmol) at r.t. under argon. After cooling to 0° C., 2,4,6-triisopropylbenzene-1-sulfonyl chloride (2.268 g, 7.49 mmol) was added in one portion. The resulting yellow reaction was warmed up to r.t. and stirred for 22 hrs. TLC showed unreacted starting material, so the reaction was warmed up to 40° C. and stirred for another 24 hrs. The reaction mixture was cooled to 0° C., to which a solution of 2,6-dimethylphenol (1.372 g, 11.23 mmol), DABCO (0.082 mL, 0.749 mmol) and triethylamine (1.566 mL, 11.23 mmol) in CH$_2$Cl$_2$ (7.49 mL) was added. Once the addition was complete, the orange reaction mixture was warmed up to r.t. and stirred for 2 days. TLC showed the complete consumption of the starting nucleoside, therefore the reaction was diluted with CH$_2$Cl$_2$ and washed with NaHCO$_3$, brine and dried over Na$_2$SO$_4$. The organic layer was condensed on rotavap, and the obtained orange residue was loaded on an ISCO column (120 g silica gel, 16×150 mm). All the fractions with the desired product were collected and condensed on rotavap to give a yellow residue (2.07 g, 93% yield), which became a yellow foam under high vacuum.

Example 15: Synthesis of Compound 19

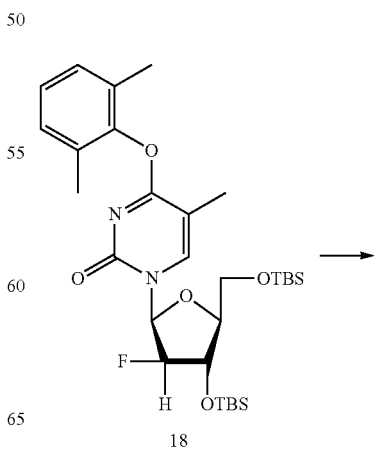

18

-continued

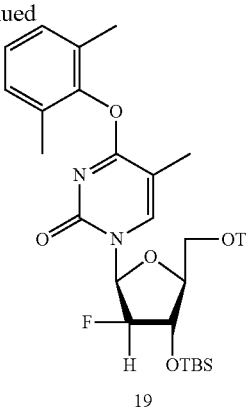

19

A sealed tube was charged with 18 (0.290 g, 0.489 mmol), Lawesson's Reagent (0.247 g, 0.611 mmol) and toluene (9.78 mL). The reaction mixture was heated up to 110° C. and stirred for 2 hrs. The yellow mixture became homogenous upon heating. The solvent was removed on rotavap and $^1$H-NMR confirmed the formation of the product (shift of 1'-H), and the obtained yellow mixture was used in next step without purification.

Example 16: Synthesis of Compound 20

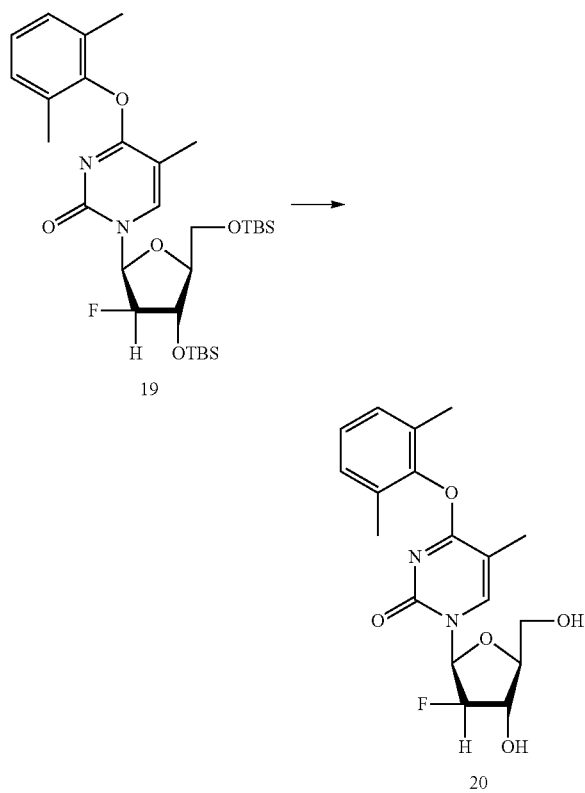

To a solution of 19 (0.298 g, 0.489 mmol) in THF (2.447 mL) was added TBAF (1M in THF) (0.297 g, 1.223 mmol) at 0° C. under argon, and the resulting yellow reaction was stirred at 0° C. for 2 hrs. After removing the solvent on rotavap, the obtained yellow residue was loaded on an ISCO column (40 g silica gel).

Example 17: Synthesis of Compound 21

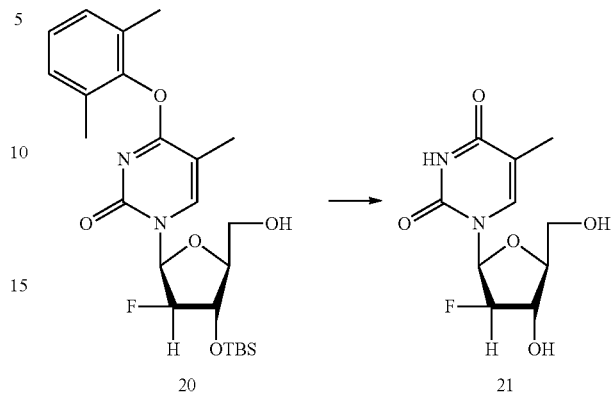

To a stirring suspension of 20 (0.455 g, 1.197 mmol) in anhydrous MeCN (2.394 mL) under argon was added dropwise a pre-made orange solution of 2-nitrobenzaldehyde oxime (0.596 g, 3.59 mmol) and 1,1,3,3-tetramethylguanidine (0.450 mL, 3.59 mmol) in anhydrous MeCN (2.394 mL) at rt. The resulting orange solution became homogenous upon the addition, which was stirred overnight at the same temperature for. TLC showed no starting material and hence the reaction was condensed on rotavap. The obtained reddish orange residue was loaded on an ISCO column (80 g silica gel, 16×150 mm). The fractions containing the desired product were collected and condensed to give a yellow solid, which was washed with methanol to give the final product 21 (0.27 g, 82% yield) as an off-white flaky solid.

Example 18: Synthesis of Compound 22

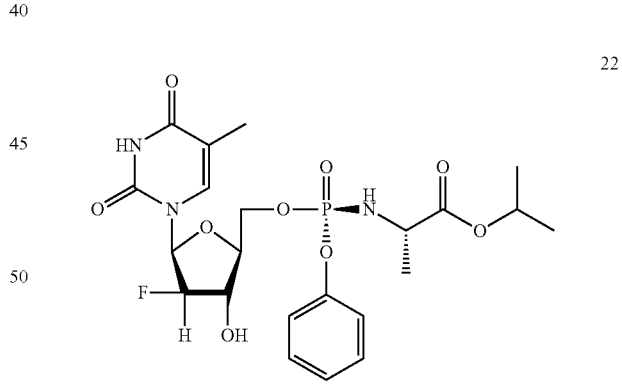

22

To a solution of 21 (0.089 g, 0.322 mmol) in THF (3.22 mL) was added dropwise t-butylmagnesium chloride (1 M in THF) (0.354 mL, 0.354 mmol) via syringe at 0° C. under argon, and the resulting mixture was stirred at the same temperature for 30 min. After the addition of a solution of 4 (0.161 g, 0.354 mmol) in THF (3.22 mL) at 0° C., the reaction mixture was allowed to warm up to r.t. and stirred overnight. The reaction mixture became cloudy upon the addition of the base and homogenous again when warming up to rt after the addition of 4. The reaction mixture was quenched with MeOH at 0° C. After condensing on rotavap, the obtained yellow residue was loaded on an ISCO column (40 g silica gel). The product, 22 (0.0537 g, 30.6% yield), was obtained as an off-white foam.

Example 19: Synthesis of Compound 23

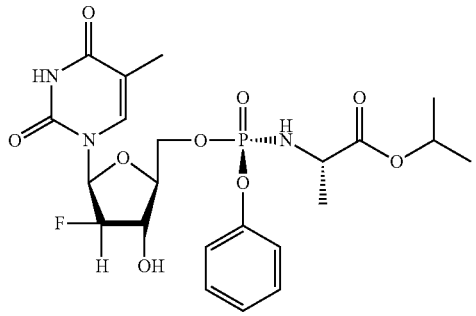

To a solution of 21 (0.081 g, 0.293 mmol) in THF (2.93 mL) was added dropwise t-butylmagnesium chloride (1 M in THF) (0.322 mL, 0.322 mmol) via syringe at 0° C. under argon, and the resulting mixture was stirred at the same temperature for 30 min. After the addition of a solution of (2S)-isopropyl 2-(((2-chloro-4-nitrophenoxy)(phenoxy)phosphoryl)amino)propanoate (0.143 g, 0.322 mmol) in THF (2.93 mL) at 0° C., the reaction was allowed to warm up to r.t. and stirred for another 24 hrs. The reaction became cloudy upon the addition of the base and homogenous again when warming up to rt after the addition of the (2S)-isopropyl 2-(((2-chloro-4-nitrophenoxy)(phenoxy)phosphoryl)amino)propanoate. The reaction was quenched with MeOH at 0° C. After condensing on rotavap, the obtained yellow residue was loaded on an ISCO column (40 g silica gel). The product 23 (0.0583 g, 36.5% yield) was obtained as a brown foam. Example 20. General Nucleobase Coupling Conditions The desired nucleobase (5 equivalents) was transferred to a dry flask under an argon atmosphere and suspended in HMDS (2 mL/mmol nucleobase). Catalytic ammonium sulfate (1-3 mgs) was added to the reaction vessel, and the suspension was allowed to reflux for 1-8 hours. During the course of reaction, the white suspension turned clear. The reaction vessel was allowed to cool to room temperature, and the excess HMDS was removed under reduced pressure. The resulting residue was dissolved in dry DCE (5 mL/mmol carbohydrate) followed by the addition of the desired carbohydrate at room temperature. Finally, neat TMSOTf (5.5 equivalents) was added to the stirring solution. The reaction was quenched with saturated sodium bicarbonate. The organic layer was collected, dried over MgSO$_4$, filtered, and concentrated under reduced pressure. The desired protected nucleoside was purified on silica gel eluting with 9:1 DCM/MeOH.

Example 20: General Nucleobase Coupling Conditions

The desired nucleobase (5 equivalents) was transferred to a dry flask under an argon atmosphere and suspended in HMDS (2 mL/mmol nucleobase). Catalytic ammonium sulfate (1-3 mgs) was added to the reaction vessel, and the suspension was allowed to reflux for 1-8 hours. During the course of reaction, the white suspension turned clear. The reaction vessel was allowed to cool to room temperature, and the excess HMDS was removed under reduced pressure. The resulting residue was dissolved in dry DCE (5 mL/mmol carbohydrate) followed by the addition of the desired carbohydrate at room temperature. Finally, neat TMSOTf (5.5 equivalents) was added to the stirring solution. The reaction was quenched with saturated sodium bicarbonate. The organic layer was collected, dried over MgSO$_4$, filtered, and concentrated under reduced pressure. The desired protected nucleoside was purified on silica gel eluting with 9:1 DCM/MeOH.

Example 21: General Desilylation Conditions

A solution of protected nucleoside dissolved in dry THF (10 ml/mmol of protected nucleoside) was treated with tetrabutylammonium fluoride (TBAF, 1 M solution in THF, 1.1 equivalents), and let to stir at room temperature for 3 hours. The crude mixture was concentrated in vacuo, and the resulting residue was purified on silica gel (0-10% methanol in dichloromethane) to give the desired nucleoside.

Example 22: General Debenzoylation Conditions

A solution of protected nucleoside obtained from base coupling reaction (0.126 g, 0.315 mmol) was added NH$_3$ in MeOH (7 M, 1.573 ml, 11.01 mmol). The reaction was allowed to stir at r.t. or with gentle heating in a sealed tube for 4.5 hrs. The yellow solution was condensed on rotavap and loaded on ISCO column (4 g column, 8% 15% MeOH/CH$_2$Cl$_2$) to give the desired nucleoside.

Example 23: Synthesis of 5'-Deuterated Nucleoside

An appropriately protected nucleoside was suspended in methylene chloride (40 mL, partially soluble). After stirring at rt for 30 min the mixture was treated sequentially with PDC, acetic anhydride and then tert-butanol. The mixture continued to stir at room temperature. TLC (5% methanol in DCM) and LCMS indicated only a small amount of remaining starting material at 4 hours. The mixture was filtered through a pad of silica gel that was loaded into a 150 mL fritted funnel. The silica was eluted with ethyl acetate. The collected filtrate was concentrated by under reduced pressure. The crude dark oil was purified by chromatography over silica gel (25 mm×175 mm) with 2:1 hexanes:ethyl acetate to ethyl acetate gradient. The pure fractions were collected and concentrated to give of a white gum. The material was placed under high vacuum for 2 days and was used in the next step without further purification.

The 5'-protected nucleoside was dissolved in 200 proof ethanol and was then treated with solid sodium borodeuteride. The mixture became homogeneous and was then heated to 80° C. After 12 h, a white/pale yellow precipitate formed. The mixture was allowed to cool to rt. TLC (5% methanol in methylene chloride) indicated complete conversion of starting material. The mixture was cooled to 0° C. with an ice-bath and then slowly quenched with acetic acid (approximately 1 mL). The clear solution was warmed to rt and then partitioned between ethyl acetate (30 mL) and brine (3 mL). The organic phase was concentrated and then purified by chromatography over silica gel (19 mm×180 mm) using a mobile phase of 5% methanol in methylene chloride.

Example 24: Synthesis of bis-POM-5'-Monophosphate Prodrugs

To a 50 mL flask charged with ((hydroxyphosphoryl)bis(oxy))bis(methylene) bis(2,2-dimethylpropanoate) (0.229 g, 0.703 mmol) was added dry THF (4 mL) to give a colorless solution. The flask was evacuated and charged with argon. Next, triethylamine (0.108 ml, 0.773 mmol) was added dropwise. After stirring at room temperature for 30 min, the desired nucleoside analog was added. The reaction mixture was cooled to 0° C. and then N-ethyl-N-isopropylpropan-2-amine (0.245 ml, 1.406 mmol), bis(2-oxooxazolidin-3-yl)phosphinic chloride (0.224 g, 0.879 mmol) and 3-nitro-1H-1,2,4-triazole (0.100 g, 0.879 mmol) were added. The reaction mixture was allowed to stir overnight gradually warming to room temperature. The reaction was then diluted with EtOAc and quenched with sat NaHCO$_3$. The organic layer was separated, dried (Na2SO4), filtered and concentrated in vacuo. The crude material was purified by ISCO column chromatography (12 g column) eluting from 100% DCM to 5% MeOH in DCM to afford the desired product.

Example 25: Synthesis of 2-Substituted-L-Ara-Nucleoside Analogs

In a dry flask under an argon atmosphere was added 1,3,5-tri-O-benzoyl-L-alpha-ribose. The carbohydrate was dissolved in dry DCM, and the reaction flask was cooled to 0° C. The 2-position was activated by adding triflic anhydride, mesyl chloride, or SO$_2$Cl$_2$ followed by imidazole. Next, an appropriate nucleophile was added to the reaction flask while at 0° C. Once the reaction was complete, as determined by TLC, the reaction was quenched with water. The reaction mixture with water was placed in a separatory funnel. The organic layer was collected and washed with brine. The organic layer was dried over magnesium sulfate, filtered, and concentrated under reduced pressure. The product was placed on an ISCO column and purified. The product was then subjected to the general base coupling procedure and general debenzoylation conditions to obtain desired nucleoside analogs.

Example 26: Synthesis of 2-fluoro-L-Ara-Nucleoside Analogs

In a dry flask under an argon atmosphere was added 1,3,5-tri-O-benzoyl-L-alpha-ribose. The carbohydrate was dissolved in dry DCM, and the reaction flask was cooled to 0° C. The 2-position was activated by adding triflic anhydride. Next, tetrabutylammonium fluoride in MeCN was added to the reaction flask while at 0° C. Once the reaction was complete, as determined by TLC, the reaction was quenched with water. The reaction mixture with water was placed in a separatory funnel. The organic layer was collected and washed with brine. The organic layer was dried over magnesium sulfate, filtered, and concentrated under reduced pressure. The product was placed on an ISCO column and purified. The product was then subjected to the general base coupling procedure and general debenzoylation conditions to obtain desired nucleoside analogs.

Example 27: Synthesis of 2-chloro or bromo-L-Ara-Nucleoside Analogs

In a dry flask under an argon atmosphere was added 1,3,5-tri-O-benzoyl-L-alpha-ribose. The carbohydrate was dissolved in dry DCM, and the reaction flask was cooled to 0° C. Next, triphenylphosphine and carbon tetrachloride or carbon tetrabromide was added to the reaction flask while at 0° C. Once the reaction was complete, as determined by TLC, the reaction was quenched with water. The reaction mixture with water was placed in a separatory funnel. The organic layer was collected and washed with brine. The organic layer was dried over magnesium sulfate, filtered, and concentrated under reduced pressure. The product was placed on an ISCO column and purified. The product was then subjected to the general base coupling procedure and general debenzoylation conditions to obtain desired nucleoside analogs.

Example 28: Synthesis of L-Ara-Nucleoside Analogs Substituted with 2-Carbon Substituents In a dry flask under an argon atmosphere was added 1,3,5-tri-O-benzoyl-L-alpha-ribose. The carbohydrate was dissolved in dry DCM, and the reaction flask was cooled to −78° C. Next, DMSO and oxylayl chloride were added to the reaction flask. After stirring for 1 hour, a solution of trimethylamine in DCM was added to the reaction flask. After consumption of starting material, the reaction was quenched with water. The organic layer was separated, washed with brine, dried over magnesium sulfate, filtered, and concentration under reduced pressure. The product was placed on an ISCO column and purified.

The resulting 2-keto intermediate was placed in a dry flask under argon atmosphere and dissolved in dry THF. The reaction flask was then cooled to −78° C. Next, an appropriate organometallic reagent was added. Once starting material was consumed, the reaction mixture was quenched with water. The organic layer was separated, washed with brine, dried over magnesium sulfate, filtered, and concentration under reduced pressure. The product was placed on an ISCO column and purified.

To a stirred solution of protected carbohydrate and 4-DMAP in acetonitrile at rt under nitrogen, was added methyl-2-chloro-2-oxoacetate dropwise via syringe. The mixture was stirred at rt for 2 h, and was then diluted with EtOAc. This organic solution was washed sequentially with sat. aq. NaHCO$_3$, water, and brine (1×120 mL each), dried over MgSO$_4$, filtered, and concentrated by rotary evaporation. The resulting crude was dried under high vacuum overnight to the desired product. The entirety of the crude product mixture was taken on to the next step without further purification.

To a stirred solution of the above product and tributyltin hydride in toluene at reflux under nitrogen, was added solid AIBN all at once. The mixture was heated at reflux for 2 h and then cooled to rt. Volatiles were removed by rotary evaporation, and the crude residue was taken up in a small amount of PhMe. Flash chromatography on the Combiflash gave the desired product, which was then subjected to the general base coupling procedure and general debenzoylation conditions.

Example 29: Procedure for Cell Incubation and Analysis

Huh-7 cells were seeded at 0.5×10$^6$ cells/well in 1 mL of complete media in 12 well tissue culture treated plates.

The cells were allowed to adhere overnight at 37°/5% $CO_2$. A 40 μM stock solution of test article was prepared in 100% DMSO. From the 40 μM stock solution, a 20 μM solution of test article in 25 ml of complete DMEM media was prepared. For compound treatment, the media was aspirated from the wells and 1 mL of the 20 μM solution was added in complete DMEM media to the appropriate wells. A separate plate of cells with "no" addition of the compound was also prepared. The plates were incubated at 37°/5% $CO_2$ for the following time points: 1, 3, 6 and 24 hours. After incubation at the desired time points, the cells were washed 2× with 1 mL of DPBS. The cells were extracted by adding 500 μl of 70% methanol/30% water spiked with the internal standard to each well treated with test article. The non-treated blank plate was extracted with 500 ul of 70% methanol/30% water per well. Samples were centrifuged at 16,000 rpm for 10 minutes at 4° C. Samples were analyzed by LC-MS/MS using an ABSCIEX 5500 QTRAP LC-MS/MS system with a Hypercarb (PGC) column.

Example 30: Procedure for Rat Pharmacokinetic Experiment

Rats were acclimated for ≥2 days after receipt. Rats were weighed the day before dosing to calculate dosing volumes. Rats were dosed p.o. with drug at 50 mg/kg, 10 mg/kg & 5 ml/kg. The rats were sampled at 6 time points: 1, 2, 3, 4, 6 and 24 hrs (3 rats per time point for test drug). The rats were euthanized and their organs were collected (see below). In order to collected blood, rats with euthanized by $CO_2$ at the appropriate time point listed above. Blood was obtained by cardiac puncture (0.3 ml) at each time point. Following blood collection, the organs were removed from the rats (see below). The blood was processed by inverting Li-Heparin tube with blood gently 2 or 3 times to mix well. The tubes were then placed in a rack in ice water until able to centrifuge (≤1 hour). As soon as practical, the blood was centrifuged at ~2000×g for 10 min in a refrigerated centrifuge to obtain plasma. Then, using a 200 μL pipette, the plasma was transferred to a labeled 1.5 ml Eppendorf tube in ice water. The plasma was then frozen in freezer or on dry ice. The samples were stored at −80° C. prior to analysis. Organs were collected from euthanized rats. The organs (lungs, liver, kidney, spleen and heart) were removed, placed in a tube, and immediately frozen in liquid nitrogen. The tubes were then transferred to dry ice. The samples were saved in cryogenic tissue vials. Samples were analyzed by LC-MS/MS using an ABSCIEX 5500 QTRAP LC-MS/MS system with a Hypercarb (PGC) column.

What is claimed is:

1. A compound having a structure of the following formula:

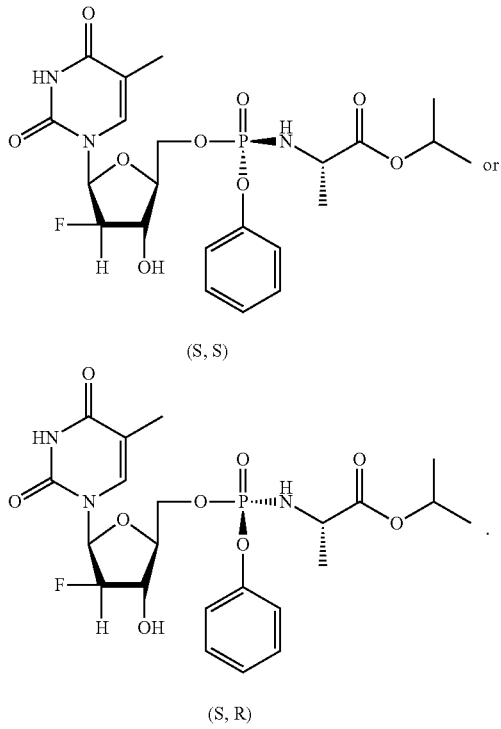

(S, S)

(S, R)

or

2. A pharmaceutical composition for the treatment or prevention of a viral infection comprising a compound or its pharmaceutically acceptable salt, of claim 1, or its pharmaceutically acceptable salt, and a pharmaceutically acceptable carrier.

3. The pharmaceutical composition of claim 2, wherein the viral infection is caused by an infectious agent comprising a DNA virus.

4. The pharmaceutical composition of claim 2 wherein the DNA virus comprises hepadnaviruses.

5. A liposomal composition comprising a liposome and a compound of claim 1, or its pharmaceutically acceptable salt, and a pharmaceutically acceptable carrier.

6. A method of treating or preventing infections caused by DNA viruses comprising administering to a host in need an effective amount of a compound of claim 1, or a pharmaceutically acceptable salt thereof.

7. The method of claim 6, wherein the DNA virus comprises hepadnaviruses.

8. The method of claim 6, wherein at least one second antiviral agent selected from abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, sofosbovir, stavudine, telaprevir, telbivudine, tenofovir, tenofovir disoproxil, tipranavir, trifluridine, trizivir, tromantadine, truvada, valaciclovir, valganciclovir, vicriviroc, vidarabine, viramidine zalcitabine, zanamivir, zidovudine, and combinations thereof is administered with the compound.

* * * * *